US009290788B2

(12) United States Patent
Brisset et al.

(10) Patent No.: US 9,290,788 B2
(45) Date of Patent: Mar. 22, 2016

(54) DEVICE FOR DETERMINING OR STUDYING THE STATE OF STIMULATION OF THE NATURAL DEFENCES OF PLANTS OR PORTIONS OF PLANTS

(75) Inventors: Marie-Noëlle Brisset, Angers (FR); Thomas Duge De Bernonville, Saint-Saturnin sur Loire (FR)

(73) Assignee: Institut National De La Recherche Agronomique, Paris (FR)

( * ) Notice: Subject to any disclaimer, the term of this patent is extended or adjusted under 35 U.S.C. 154(b) by 0 days.

(21) Appl. No.: 13/805,332

(22) PCT Filed: Jun. 24, 2011

(86) PCT No.: PCT/FR2011/051470
§ 371 (c)(1),
(2), (4) Date: Dec. 18, 2012

(87) PCT Pub. No.: WO2011/161388
PCT Pub. Date: Dec. 29, 2011

(65) Prior Publication Data
US 2013/0090261 A1    Apr. 11, 2013

(30) Foreign Application Priority Data

Jun. 24, 2010 (FR) ..................... 10 55042

(51) Int. Cl.
*C12Q 1/68* (2006.01)
*C12Q 1/02* (2006.01)

(52) U.S. Cl.
CPC .............. *C12Q 1/025* (2013.01); *C12Q 1/6876* (2013.01); *C12Q 1/6895* (2013.01); *C12Q 2600/158* (2013.01)

(58) Field of Classification Search
None
See application file for complete search history.

(56) References Cited

U.S. PATENT DOCUMENTS

2002/0144307 A1   10/2002   Simmons et al.
2007/0124839 A1    5/2007   Bartsch et al.
2010/0267566 A1   10/2010   Schulz et al.

FOREIGN PATENT DOCUMENTS

| EP | 1038965 | 9/2000 | |
| WO | WO 2007/062737 | 6/2007 | |
| WO | WO 2009/041805 | 4/2009 | |
| WO | WO 2009/041805 A1 * | 4/2009 | ............... C12Q 1/68 |

OTHER PUBLICATIONS

Norelli et al (2009) "Rapid transcriptional response of apple to fire blight disease revealed by cDNA suppression subtractive hybridization analysis" Tree Genetics & Genomes 5:27-40.*

Nolan et al. (2006) "Quantification of mRNA using real-time RT-PCR" Nature Protocols 1(3):1559-82.*
Lowe et al. (1990) "A computer program for selection of oligonucleotide primers for polymerase chain reactions" Nucleic Acids Research 18(7):1757-1761.*
Buck et al. (1999) "Design Strategies and Performance of Custom DNA Sequencing Primers" Biotechniques 27(3):528-536.*
Rozen et al. (1999) "Primer3 on the WWW for General Users and for Biologist Programmers" Methods in Molecular Biology 132:365-386.*
Bonasera J. M. et al. (Oct. 2006) "PR genes of apple: identification and expression in response to elicitors and inoculation with Erwinia amylovora" BMC Plant Biology. Biomed Central. London. GB. vol. 6. No. 1. p. 23.
Brisset et al. (2000) Acibenzolar-S-methyl Induces the Accumulation of Defense-related Enzymes in Apple and Protects from Fire Blight Eur. J. Plant Pathol. 106, 529-536.
Brisset et al. (Apr. 2005) The potential of natural plant defense inducers in the protection of apple and pear trees (Inducteurs de defenses naturelles des plantes) Pytoma 581:20-24, Abstract only.
Czechowski et al. (Mar. 2004) Real-time RT-PCR profiling of over 1400 Arabidopsis transcription factors: unprecedented sensitivity reveals novel root-and shoot-specific genes. Plant J. 38, 366-379.
Czechowski et al. (Sep. 2005) Genome-wide identification and testing of superior reference genes for transcript normalization in Arabidopsis, Plant Physiol. 139, 5-17.
De Vos Martin et al: (Sep. 2005) "Signal signature and transcriptome changes of Arabidopsis during pathogen and insect attack" Molecular Plant-Microbe Interactions. vol. 18. No. 9. pp. 923-937.
Livak and Schmittgen, (2001) "Analysis of Relative Gene Expression Data Using Real-Time Quantitative PCR and the 2-$\Delta\Delta CT$ Method" Methods 25:402-408, 2001.
Prime-A-Plant Group et al: (Oct. 2001) "*Priming: getting ready for battle*". Molecular Plant-Microbe Interactions•MPMI Oct. 2006 vo 1. 19. No. 10.1. pp. 1062-1071.
Vandesompele et al. (Jun. 2002) "Accurate normalization of real-time quantitative RT-PCR data by geometric averaging of multiple internal control genes" Genome Biol. 3(7): research 0034.1-0034.11.

(Continued)

*Primary Examiner* — Tracy Vivlemore
*Assistant Examiner* — Karen S Weiler
(74) *Attorney, Agent, or Firm* — Lathrop & Gage LLP

(57) ABSTRACT

The present invention relates to a device for determining or studying the state of stimulation of the natural defenses of plants or plant portions, which plants advantageously belong to the Rosaceae family. The corresponding device includes means for determining the expression level, in a sample of plants or plant portions, of at least one target gene in each of the following groups (a) to (i):
(a) PR-1, PR-2, PR-4 PR-5, PR-8, PR-14, PR-15; (b) PAL, CHS, DFR, ANS, PPO; (c) HMGR, FPPS, Far; (d) CSL; (e) APOX, GST, POX; (f) CalS, Pect, CAD; (g EDS1, WRKY; (h) LOX2, JAR; and (i) ACCO, EIN3. Said device preferably consists of a kit which contains a determination means in the form of pairs of primers, for implementing a quantitative PCR technique.

7 Claims, 2 Drawing Sheets

(56) References Cited

OTHER PUBLICATIONS

Figure 1:
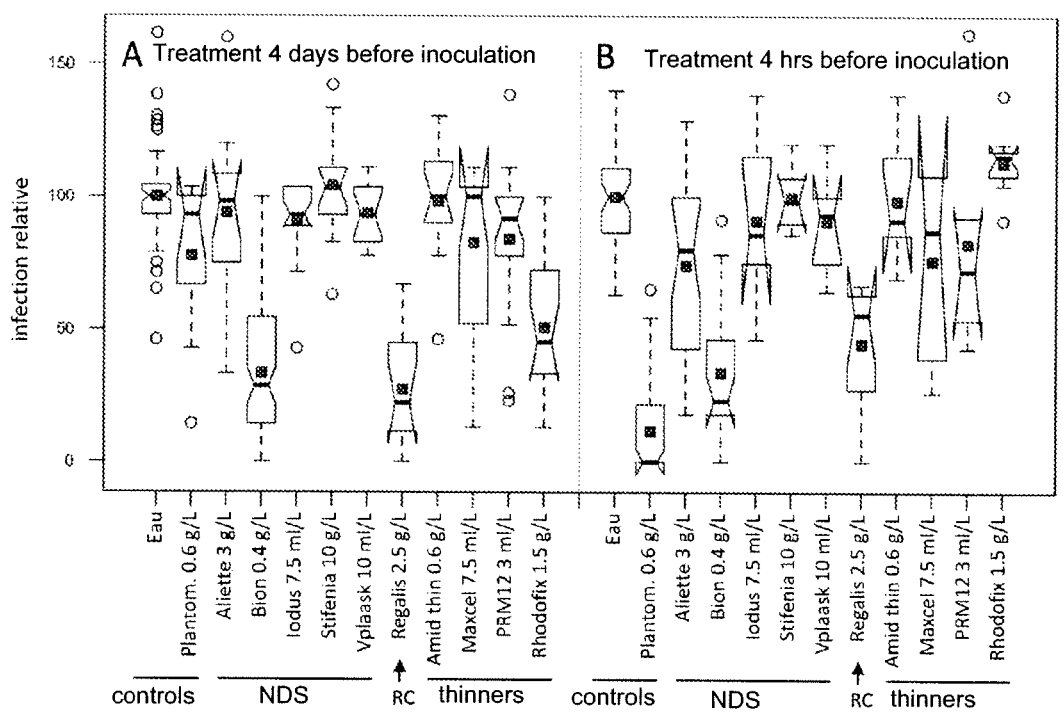

Venisse et al., (2002) Modulation of Defense Responses of *Malus* spp. During Compatible and Incompatible Interactions with Erwinia amylovora Molecular Plant-Microbe Interactions 15, 1204-1212.

Ziadi, S. et al. (Oct. 2001) Characterization in apple leaves of two subclasses of PR-10 transcripts inducible by acibenzolar-S-methyl, a functional analogue of salicylic acid, Physiol.Mol. Plant Pathology 59:33-43.

International Search Report (English Translation) issued in PCT/FR2011/051470 on Dec. 29, 2011.

Written Opinion of the International Search Authority issued in PCT/FR2011/051470 on Dec. 24, 2011.

International Preliminary Report on Patentability issued in PCT/FR2011/051470 on Dec. 28, 2011.

* cited by examiner

Note: eau is water

DEVICE FOR DETERMINING OR STUDYING THE STATE OF STIMULATION OF THE NATURAL DEFENCES OF PLANTS OR PORTIONS OF PLANTS

CROSS-REFERENCE TO RELATED APPLICATIONS

This application is a U.S. National Stage application of international application PCT/FR2011/051470, filed in French on Jun. 24, 2011, which designates the United States, and which claims the benefit of FR1055042, filed in French on Jun. 24, 2010. Each of these applications is incorporated by reference herein in its entirety.

FIELD OF THE INVENTION

The present invention relates to the field of devices for determining and/or studying the state of stimulation of the natural defenses of plants.

This invention specifically relates to a device including means for determining the expression level or profile of a specific combination of endogenous target genes in plants or portions of plants, so as to identify the presence, level and/or intensity of stimulation of the natural defenses of said plants or portions of plants.

PRIOR ART

Plants are exposed to many stresses, said stresses including events consisting of so-called "abiotic" stresses (dryness, extreme temperature, ultraviolet radiation, etc.) and so-called "biotic" stresses (viruses, bacteria, fungi, pests, etc.).

Plants are known to possess a plurality of endogenous mechanisms capable of providing an effective defense against a wide range of such stresses.

In the case of biotic stresses, three levels of defense mechanisms may develop from a space-time standpoint, starting with the point of infection or infestation, and may contribute to halting the spread of the disease.

At the site of penetration of the pathogen, the cells in contact with the pathogenic agent can self-destruct and thus slow down the progression thereof; this first defense phenomenon is known as a hypersensitivity reaction (HR).

Warning signals can be transmitted from the site of infection to the neighboring cells, thereby creating a localized area of acquired resistance, wherein many defense compounds are accumulated; this second level of defense ensures localized acquired resistance (LAR).

Signals can likewise be transmitted to the entire plant, which induces a third level of defense: systemic acquired resistance (SAR).

Well-characterized physiological phenomena or paths of the defense mechanisms, which are inducible by pathogenic agents, and which are involved in the LAR and SAR defense levels, are, for example:
(i) the production of anti-microbial compounds, such pathogenesis-related proteins (commonly referred to as "PR" proteins or "PRP") and phytoalexins,
(ii) the strengthening of cell walls (deposition of callosis, lignification, cross-linking of proteins), and
(iii) the production of certain plant hormones, in particular salicylic acid (A), jasmonic acid (JA) and ethylene (ET), said hormones playing an important part in signaling stress-induced defense mechanisms.

In addition to these stress-induced reactions, the induction of SAR gives the plant the ability to resist subsequent stresses, including those at locations distant from the first site of infection or infestation in said plant.

It may happen that the defense mechanisms are not activated completely, but rather that the tissues are only "sensitized'. A faster and stronger expression of the defense mechanisms is only triggered after the plant has been exposed to subsequent stress. This phenomenon is commonly referred to as "priming" or "potentiation".

This in-depth knowledge of the defense mechanisms of plants has enabled the development and use of phytosanitary products, which no longer act directly on the cause of the stress, but have the property of acting indirectly by activating and stimulating the natural defense mechanisms.

Such products having a stimulating effect on the natural defenses (also referred to as "natural defense stimulators" or by the acronym "NDS") can be classified into two primary families:
(i) so-called "direct stimulator" compounds, which, once applied to the plant, bring about a complete activation of the defense mechanisms, whether pathogens are present or not, and
(ii) so-called "potentiating" compounds, which, after application to the plant, only trigger the aforesaid "potentiation" phenomenon (the defense reactions activating only after attack by a pathogenic agent or stress).

The majority of these NDS products are still known by the name of "elicitors" (or "eliciting") or else "resistance inducers".

Numerous studies have been conducted on these defense mechanisms, and the products having a natural defense stimulating effect, from model species, and in particular from *Arabidopsis thaliana*.

However, at the current time, it must be indicated that there is no specific regulatory framework governing the conditions for marketing and using NDS products.

Thus, in order to benefit from marketing authorization (MA), such NDS products may enter (i) as is, in the category of phytopharmaceutical inputs, or (ii) mixed with fertilizing molecules, in the category of fertilizing inputs.

Very few MAs for phytopharmaceutical inputs have been issued to date for NDS products.

As concerns specifically knowledge about the effects of these inputs on plants, stimulation of the natural defenses is generally studied only at a cellular scale, e.g., on cell suspensions or detached organs.

As far as the applicant knows, a natural defense stimulating effect on entire plants has generally not been proven at the molecular level.

Conversely, a large variety of products are known that have been officially approved as phytopharmaceutical inputs or as fertilizing inputs, and which might be likely to also exert a stimulating effect on the natural defenses of plants, even though such an additional effect has not been proven or identified.

Some products might likewise have an inhibiting effect on the natural defenses of plants.

The situation stated above with regard to plants in general, is true in particular for the plants of the Rosaceae family, which includes various fruit species.

Consequently, there is a need for professionals to have a device or multipurpose tool at their disposal, which would make it possible to simply and quickly identify the state of stimulation of the natural defenses of plants or portions of plants, in particular those of the Rosaceae family.

This device or multipurpose tool would likewise advantageously have the purpose of enabling the substances to be screened for their properties of stimulating the natural defenses of plants, including plants belong to the Rosaceae family.

Such a device or tool should, in particular, offer the possibility of discriminating between (i) NDS products that actually activate the plant defenses, and (ii) products that are devoid of such an effect.

This device or tool would thus enable new NDS products to be screened and to carry out various studies on the NDSs, e.g., studies aiming to determine the mechanism or mechanisms of action and/or the molecular pathways involved in the effect of stimulating the defenses of a plant via a particular NDS product, via a particular combination of NDS products, or else via a combination of one or more NDS products with one or more other inputs likely to have an antagonistic effect on stimulating the defenses.

SUMMARY OF THE INVENTION

The present invention relates to a device for determining or studying the state of stimulation of the natural defenses of plants or portions of plants, which device includes means for determining the expression level of a combination of target genes in a sample of plants or portions of plants, said determination means including:
(a) a means of determining the expression level of at least one target gene chosen from among the following target genes: PR-1, PR-2, PR-4 PR-5, PR-8, PR-14, PR-15;
(b) a means of determining the expression level of at least one target gene chosen from among the following target genes: PAL, CHS, DFR, ANS, PPO;
(c) a means of determining the expression level of at least one target gene chosen from among the following target genes: HMGR, FPPS, Far;
(d) a means of determining the expression level of the target gene CSL;
(e) a means of determining the expression level of at least one target gene chosen from among the following genes: APOX, GST, POX;
(f) a means of determining the expression level of at least one target gene chosen from among the following target genes: CalS, Pect, CAD;
(g) a means of determining the expression level of at least one target gene chosen from among the following target genes: EDS1, WRKY;
(h) a means of determining the expression level of at least one target gene chosen from among the following target genes: LOX2, JAR;
(i) a means of determining the expression level of at least one target gene chosen from among the following target genes: ACCO, EIN3.

In some embodiments, said device includes means of determining the expression level of the combination of the following target genes: PR-1, PR-2, PR-4, PR-5, PR-8, PR-14, PR-15, PAL, CHS, DFR ANS, PPO, HMGR, FPPS, Far, CSL, APOX, GST, POX, CalS, Pect, CAD, EDS1, WRKY, LOX2, JAR, ACCO, EIN3.

In some embodiments, said means of determining the expression level of a target gene are chosen from among (i) the fragments of nucleic acid capable of hybridizing in a specific manner with the mRNAs expressed by said target gene or with the corresponding cDNAs, or with fragments of said mRNAs or said cDNAs, and/or with said cDNAs, or fragments of said expression products.

In some embodiments, the nucleic acid fragments capable of hybridizing specifically with the mRNAs expressed by said target gene or with the corresponding cDNAs consist of primers, said primers preferably being chosen from among the following sequences: SEQ ID Nos. 32 to 87.

The present invention likewise relates to a method for identifying an expression profile of a combination of target genes making it possible to determine, or at least evaluate, a stimulation state of the natural defenses of plants or portions of plants, which method includes the following steps:
(i) determining the expression profile of a combination of target genes by means of the aforesaid device, for a set of plants or portions of plants, of which the stimulation state of the natural defenses thereof is known, and then
(ii) determining an expression profile for said combination of target genes corresponding to a specific stimulation state of the natural defenses of said plants or portions of plants, using the data derived from step (i).

The invention also relates to a method for determining or evaluating the stimulation state of the natural defenses of a plant or a plant portion, which includes the following steps:
(i) taking a sample from said plant or said plant portion,
(ii) determining the expression profile of a combination of target genes in said sample taken in step (i), by means of the aforesaid device,
(iii) comparing the expression profile obtained in step (ii) with a reference expression profile,
(iv) determining or evaluating the stimulation state of the natural defenses of said plant or said plant portion from said expression profile obtained during step (ii).

The present invention also relates to a method for selecting a substance having the property of modulating the stimulation state of the natural defenses of a plant or plant portion, which includes the following steps:
(i) placing said plant or said plant portion in contact with the substance being tested,
(ii) determining the expression profile of a combination of target genes in a sample taken from said plant or said plant portion subsequent to step (i), by means of the aforesaid device,
(iii) comparing the expression profile obtained in step (ii) with a reference expression profile, in order to determine or evaluate the stimulation state of the natural defenses in said sample,
(iv) positively selecting said substance if the comparison in step (iii) shows that said substance tested in step (i) modulates the stimulation state of the natural defenses of said plant or said plant portion.

The present invention also relates to a method for selecting a plant having a natural defense stimulation state capable of giving same improved resistance to at least one biotic and/or abiotic stress of interest, which includes the following steps:
(i) applying said stress or stresses to a plant or plant portion,
(ii) determining the expression profile of a combination of target genes in a sample taken from the plant or said plant portion, by means of the aforesaid device,
(iii) comparing the expression profile obtained in step (ii) with a reference expression profile, in order to determine or evaluate the stimulation state of the natural defenses in said sample,
(iv) positively selecting said plant or said plant portion if the comparison of step (iii) shows that said plant or said plant portion possesses a natural defense stimulation state capable of giving same improved resistance to at least one biotic and/or abiotic stress of interest.

DETAILED DESCRIPTION OF THE INVENTION

The inventors have identified a specific set of target genes, the expression level or profile of which comprises a simple and effective means for determining and/or studying the stimulation state of the natural defenses of plants, and advantageously plants of the Rosaceae family.

The inventors have indeed demonstrated that analysis of a specific combination of target genes enables determination of the stimulation state of the natural defenses of plants that are (i) exposed to an NDS product, (ii) exposed to a biotic stress source or event, (iii) exposed to an abiotic stress source or event, or even (iv) to a combination of two or three of the aforesaid exposures.

These results enabled the inventors to develop a device, advantageously a device including means for determining, advantageously in vitro, the expression level or profile of a specific combination of target genes (advantageously by targeted transcriptomic analysis or targeted proteomic analysis), in a sample derived from a plant, including a sample derived from a plant portion, including a plant of the Rosaceae family.

The inventors have shown that in vitro determination of the expression level or profile of this specific combination of target genes enables the study and/or determination of the stimulation state of the natural defenses of the plant from which said sample was derived.

The present invention thus relates to a novel device or a novel research tool, advantageously a molecular biology device, for characterizing a biological sample, by determining the expression level of a specific combination of target genes.

The present invention specifically relates to a device for determining and/or studying the natural defense stimulation state of plants, which device includes means for determining the expression level or profile of a combination of target genes in a sample from a plant or plant portion, said determination means including:
(a) a means of determining the expression level of at least one target gene chosen from among the following target genes: PR-1, PR-2, PR-4 PR-5, PR-8, PR-14, PR-15;
(b) a means of determining the expression level of at least one target gene chosen from among the following target genes: PAL, CHS, DFR, ANS, PPO;
(c) a means of determining the expression level of at least one target gene chosen from among the following target genes: HMGR, FPPS, Far;
(d) a means of determining the expression level of the target gene CSL;
(e) a means of determining the expression level of at least one target gene chosen from among the following genes: APOX, GST, POX;
(f) a means of determining the expression level of at least one target gene chosen from among the following target genes: CalS, Pect, CAD;
(g) a means of determining the expression level of at least one target gene chosen from among the following target genes: EDS1, WRKY;
(h) a means of determining the expression level of at least one target gene chosen from among the following target genes: LOX2, JAR;
(i) a means of determining the expression level of at least one target gene chosen from among the following target genes: ACCO, EIN3.

Despite the limited and specific number of target genes analyzed, the inventors have shown that the device according to the invention comprises a particularly versatile and powerful tool, enabling the study and/or determination of the natural defense stimulation state of plants (i) exposed to one or more compounds or one or more natural defense-stimulating compositions and/or (ii) exposed to a large variety of stresses, which include both biotic stresses and abiotic stresses, and/or (iii) exposed to a combination of the aforesaid exposures (i) and (ii).

The device according to the invention has the advantage of producing simple, rapid and actually interpretable results concerning the natural defense stimulation state of a plant.

The device according to the invention makes it possible, in particular, to study and/or identify candidate compounds likely to consist of natural defense stimulators for plants, and capable of inducing a reaction mechanism in the plants against assault by harmful organisms and/or a defense reaction mechanism against natural abiotic stresses.

According to a preferred embodiment, the device according to the invention includes means of determining the expression level of the following genes:
(i) for group (a), a means of determining the expression level of at least one of the following genes: PR-1, PR-2, PR-4 or PR-8, a means of determining the expression level of the gene PR-5, a means of determining the expression level of the gene PR-14 and a means of determining the expression level of the gene PR-15, and/or
(ii) for group (b), a means of determining the expression level of the gene PAL, a means of determining the expression level of at least one of the following genes: CHS, DFR or ANS, and a means of determining the expression level of the gene PPO, and/or
(iii) for group (c), a means of determining the expression level of at least one of the following genes: HMGR and Far, and a means of determining the expression level of the gene FPPS and/or
(iv) for group (e), a means of determining the expression level of the gene APOX and a means of determining the expression level of at least one of the following genes: GST and POX.

According to a more preferable embodiment, this device includes means for determining the expression level of the combination of the following target genes: PR-1, PR-2, PR-4, PR-5, PR-8, PR-14, PR-15, PAL, CHS, DFR ANS, PPO, HMGR, FPPS, Far, CSL, APOX, GST, POX, CalS, Pect, CAD, EDS1, WRKY, LOX2, JAR, ACCO, EIN3.

The means of determining the expression level of a target gene are advantageously chosen from among (i) fragments of nucleic acid capable of hybridizing in a specific manner with the mRNAs expressed by said target gene or with the corresponding cDNAs, or with fragments of said mRNAs or said cDNAs, and/or (ii) antibodies binding specifically to the expression products of said target gene, said mRNAs or said cDNAs, or fragments of said expression products.

In the above embodiments (i), the aforesaid nucleic acid fragments advantageously are composed of nucleotide primers hybridizing specifically with the mRNAs, cDNAs, or fragments thereof, each derived from the target genes of interest.

In some embodiments, the corresponding nucleotide primers are advantageously suitable for determining the expression level of the target genes by means of a quantitative PCR method.

The nucleotide primers are advantageously chosen from among the following sequences: SEQ ID Nos. 32 to 87. The use of these primers in the arrangement according to the invention is shown in the examples.

According to a particular embodiment, the nucleic acid fragments or said antibodies are immobilized on a substrate.

In the embodiments of the device wherein the means of determining the expression level of a target gene consist of nucleic acids, said device thus advantageously consists of a DNA chip, also capable of being denoted by the name of "low quantitative density chip" or "qPFD" (due to the limited number of target genes).

In the above embodiments (ii), the antibodies are chosen from among polyclonal and monoclonal antibodies, including recombinant monoclonal antibodies.

The present invention likewise relates to methods implementing the device according to the invention, which will be presented in detail in the description, namely:
- a method for identifying an expression profile for a combination of target genes (also denoted as "signature" or "expression signature") making it possible to determine, or at least evaluate, a natural defense stimulation state of plants;
- a method for determining or evaluating the natural defense stimulation state of plants or a portion of such plants;
- a method for selecting a substance having the property of modulating the natural defense stimulation state of a plant or plant portion;
- a method for selecting a plant or plant portion having a natural defense stimulation state likely to give improved resistance to at least one biotic stress and/or abiotic stress of interest.

Each of these devices is particularly suitable for being used on plants or plant portions belonging to the Rosaceae family.

As disclosed subsequently herein below, the present invention therefore provides a novel device or tool for determining and/or studying the natural defense stimulation state of plants, which, to accomplish this, uses the determination of the expression profile and/or the detection of the expression profile and/or the quantification of the expression profile of a combination of target genes in a sample of a plant or plant portion.

The inventors have thus identified a set of target genes contained in the plant genome, which comprise biological markers capable of serving as indicators in studying and/or determining the presence and/or the level and/or the intensity of the natural defense stimulation state of a plant or plant portion.

The inventors have shown that the device according to the invention, using a limited and specific number of markers, makes it possible to determine and/or study the effect of a compound or a composition of interest and/or a biotic stress and/or an abiotic stress on the natural defense stimulation state of plants or portions of plants treated.

It turns out that this device according to the invention is particularly advantageous in studying plants or portions of plants of the genus Rosaceae or Roses, as is shown in the examples.

After having defined certain terms, the present description discloses the target genes specifically selected for studying and/or determining the natural defense stimulation state of the plants or portions of plants, and then describes the device according to the invention along with the means for measuring and/or determining the expression level or profile of said respective target genes.

Such a device has many uses, which will likewise be developed below, in particular: (i) the selection and study of compounds or compositions that are capable of modifying the natural defense stimulation state of plants or portions of plants and/or (ii) the selection of plants or portions of plants having or capable of having a particular natural defense stimulation state, e.g., following application of a compound or composition of interest and/or a biotic stress and/or an abiotic stress.

DEFINITION[S]

A "plant" is understood to mean any multicellular organism belonging to the subkingdom of Tracheobionta, including pteridophytes and spermaphytes. The term "spermaphytes" is understood to mean an organism belonging to the gymnosperms or more preferably to the angiosperms. Understood to be included among the angiosperms are monocotyledons or else dicotyledons, and more preferably eudicotyledons. The term "dicotyledons" is understood to include the following subclasses: Asteridae, Caryophyllidae, Dilleniidae, Hamamelidae, Mamamelididae, Magnoliidae or Rosidae. The term "Rosidea" is understood to include the following orders: Apiales, Celastrales, Cornales, Euphorbiales, Fabales, Geraniales, Haloragales, Finales, Myrtales, Podostemales, Polygalales, Proteales, Rafflesiales, Rhamnales, Rhizophorales, Roasles, Santales, Sapindales. In the Rosidea order, a plant from the family of Rosaceae is chosen more preferably, including apple trees.

A "sample" is understood to mean a biological sample containing the biological material enabling detection of the expression of the combination of target genes.

The biological material can include, in particular, proteins and/or nucleic acids such as deoxyribonucleic acids (DNAs) or ribonucleic acids (RNAs), in particular. This biological material includes specific material from the target genes, in particular, such as the mRNAs transcribed by the target genes or the proteins derived from these mRNAs, but can likewise include non-specific material from the target genes, in particular such as the mRNAs transcribed by genes other than the target genes or the proteins derived from these mRNAs. According one embodiment of the invention, the biological material includes RNAs, and more preferably complete RNAs; the complete RNAs include the transfer RNAs, the messenger RNAs (mRNAs), such as the mRNAs transcribed by the target genes but likewise transcribed by any other gene, and the ribosomal RNAs.

The biological samples include tissue fragments taken from the plant, as well as the products resulting from the extraction or purification of the nucleic acids (DNAs, mRNAs) or proteins contained in said tissue fragments, as well as certain transformation products from the substances contained in said tissue fragments or in said transformation products, e.g., cDNA type nucleic acids obtained by reverse transcription of the mRNA type nucleic acids.

A "plant portion" is understood to mean the fragment of a plant containing at least one plant cell, e.g., a plant organ (such as a leaf, bud, flower, root, fruit, seed or a portion thereof) or a plant tissue (such as a meristem).

The term "environmental stresses" is understood to denote all of the factors external to a plant, which are capable of affecting the normal metabolism of said plant and of inducing an adaptation and/or defense reaction therein. Environmental stresses can be due to living beings (a matter of biotic stress), or other factors (then a matter of abiotic stress).

Biotic stresses encompass, in particular, all of the microbial pathogens, such as fungal, bacterial and viral pathogens or pests, and the infections or infestations for which they are responsible.

Abiotic stresses encompass all of the stresses of a physical or chemical nature, and in particular oxidative or climatic stresses; this involves, in particular, water stress, such as the lack of water, or thermal stress, such as cold or heat. Oxidative stresses encompass all stresses resulting in an increase in the concentration of oxidizing agents in a plant or plant portion.

A "natural defense stimulation state" is understood to mean the development of a set of biological modifications that give said plant (i) immediate resistance, in particular LAR or SAR, and/or (ii) a potentiation-type pre-sensitivity owing to which said plant becomes capable of reacting more effectively to a subsequent biotic or abiotic stress.

A "natural defense stimulation state" likewise refers to the activated or non-activated status of the various molecular pathways involved in the natural defense mechanisms.

A "natural defense stimulation state" is also understood to mean stress resistance, i.e., various levels of tolerance to stress, namely an ability of plants to confront biotic and/or abiotic stresses. Stress resistance can be classified according to various levels: —sensitivity, average tolerance to one or more biotic or abiotic attacks, and—high tolerance or complete resistance to one or more biotic or abiotic attacks.

A "natural defense stimulation state" is understood in particular to means the ability of a plant to resist diseases, i.e., various levels of resistance and/or tolerance of a plant to diseases, including sensitivity, average resistance and high resistance or complete resistance to one or more pathogens. This may correspond to a modification of the symptoms induced by pathogens of the disease (such as the frequency and/or size of the lesions, etc.), as well as the extent of colonization of the tissues by the pathogen or the percentage of infection relative to those observed in susceptible test plants cultivated with identical diseases. Resistance to the disease can likewise be shown by a higher growth and/or yield of the resistant plants in comparison with susceptible plants, when they are cultivated under exposure to the disease.

The expressions "activated natural defense stimulation state", "induced natural defense stimulation state", "improved stress resistance", "increased resistance to the disease" and 'strengthened defense reaction" refer in particular to any significant increase in the stress resistance or disease resistance of a plant or plant tissues, relative to an appropriate control such as a plant not subjected to an NDS product or this same stress or this same disease.

An "activated natural defense stimulation state" or "induced natural defense stimulation state" also refers to any activation/induction of the molecular pathways involved in the natural defense mechanisms in a plant or plant portion subjected to an NDS product or a stress, relative to an appropriate control such as a plant not subjected to this same NDS product or this same stress.

The expression 'determination and/or study of the natural defense stimulation state" is understood to mean both (i) the determination and/or study of the existence or absence of such natural defense stimulation, and (ii) the determination and/or study of the level and/or intensity of said natural defense stimulation.

The expressions "expression level of a combination of target genes" or "expression profile of a combination of target genes" are understood to mean any detectable, measurable and/or quantifiable biological parameter or marker in the plant or plant portion studied, which corresponds directly or indirectly to the expression level of each of the genes selected.

The terms "expression level" includes the absence and/or presence and or a value representative of the quantity of messenger RNAs ("mRNAs") transcribed from the genomic DNA corresponding to the selected target genes.

The expression "expression level" also includes the absence and/or presence and/or the value representative of the quantity of proteins encoded by the selected target genes.

An "overexpression" or "activation" of a gene is understood to mean a quantitative expression level of the marker for said gene, which is multiplied by at least 3 relative to a reference quantitative level, more preferably at least 4×, 5×, 10×, 20×, 30× or more.

An "underexpression" or "inactivation" or "repression" of a gene is understood to mean a quantitative expression level of the marker for said gene, which is divided by at least 3 relative to a reference quantitative level, preferably at least 4×, 5×, 10×, 20×, 30× or more, or even non-detectable.

A "constant" expression level of a gene corresponds to a quantitative expression level of the marker of said gene, which falls within a range defined by dividing said quantitative level by 3 and multiplying same by 3 relative to the reference quantitative level.

The expression level of the markers can be "relative", i.e., the variation in the expression level of one or more genes is compared to the expression level of other samples, after "normalization" of the expression levels using control genes, for example.

The expression modulation multiple for each of the target genes, when overexpressed or underexpressed, can be measured, for example, by using quantitative PCR type determination, advantageously in real time, as shown in the examples.

The results can be obtained according to the ΔΔCt (Delta Delta CT) method, which provides the relative expressions of the defense genes in a given sample relative to the sampled referred to as a "calibrator" (e.g., a sample of an untreated plant or plant portion, or else, for example, a sample of a treated plant or plant portion), said expressions [being] normalized by the geometric mean of the reference genes of these samples (Vandesompele et al., Genome Biol. 3(7): research 0034.1-0034.11, 2002; Livak and Schmittgen, Methods 25:402-408, 2001).

The expression level of the markers can likewise be "absolute", i.e., the expression levels of the markers refer to the absolute quantity of said markers (mRNAs or proteins) in a sample.

According to the invention, an "expression profile" or an "expression signature" consists of a representation of all of the expression values for each of the tested target genes, for the tested combination of target genes.

Combination of Target Genes Used in the Device According to the Invention

The device according to the invention includes means for determining and/or studying the expression level of an established combination of target genes, or otherwise known as "a set of target genes".

This combination according to the invention consists of the following nine groups of target genes (a) to (i):

(a) at least one target gene chosen from among the genes encoding PR-proteins: PR-1, PR-2, PR-4, PR-5, PR-8, PR-14, PR-15;

(b) at least one target gene chosen from among the genes encoding enzymes of the phenylpropanoid pathway: PAL, CHS, DFR, ANS, PPO;

(c) at least one target gene chosen from among the genes encoding enzymes of the isoprenoid pathway: HMGR, FPPS, Far.

(d) a CSL target gene, encoding for a cysteine catabolism enzyme;

(e) at least one target gene chosen from among the genes encoding for antioxidant enzymes: APOX, GST, POX;

(f) at least one target gene chosen from among the genes encoding enzymes involved in wall modifications: CalS, Pect, CAD;

(g) at least one target gene chosen from among the genes involved in the salicylic acid signaling pathway: EDS1, WRKY;

(h) at least one target gene chosen from among the genes involved in the jasmonic acid signaling pathway: LOX2, JAR;

(i) at least one gene chosen from among the target genes involved in the ethylene signaling pathway: ACCO, EIN3.

In practice, overexpression in a tested sample of at least one of the target genes, and more preferably a combination of said target genes in at least two of said groups (a) to (i), relative to an untreated sample, enables identification of the plants or plant portions having an activated or induced natural defense stimulation state.

These selected target genes are presented in greater detail in Table 1 below.

TABLE 1 list of the target genes according to the invention

| SEQ ID NO. | NAME OF THE GENE | Apple Unigene (NCBI) | Function of the gene | Apple cDNA Accession No. (NCBI) |
|---|---|---|---|---|
| 1 | PR-1 | Mdo.3966 | Pathogenesis-related protein 1 PR-protein | AF507974 |
| 2 | PR-2 | Mdo.2984 | Pathogenesis-related protein 2 (glucanases) PR-protein | AF494404 |
| 3 | PR-4 | Mdo.2382 | Pathogenesis-related protein 4 (hevein-like) PR-protein | CN877594 |
| 4 | PR-5 | Mdo.999 | Pathogenesis-related protein 5 (thaumatin-like, osmotin) PR-protein | DR998561 |
| 5 | PR-8 | Mdo.3935 | Pathogenesis-related protein 8 (class III chitinase) PR-protein | DQ318214 |
| 6 | PR-14 | Mdo.12217 | Pathogenesis-related protein 14 (lipid transfer protein) PR-protein | CV656658 |
| 7 | PR-15 | — | Pathogenesis-related protein 15 (oxalate oxidase) PR-protein | GO500607 |
| 8 | PAL | Mdo.2983 | Phenylalanine ammonia-lyase Phenylpropanoid pathway | AF494403 |
| 9 | CHS | Mdo.6113 | Chalcone synthase Phenylpropanoid pathway | AF494401 |
| 10 | DFR | Mdo.13736 | Dihydroflavonol reductase Phenylpropanoid pathway | AF494390 |
| 11 | ANS | Mdo.2932 | Anthocyanidin synthase Phenylpropanoid pathway | DQ15695 |
| 12 | PPO | Mdo.2905 | Polyphenol oxidase Phenylpropanoid pathway | L29450 |
| 13 | HMGR | Mdo.2960 | Hydroxymethyl glutarate-CoA reductase Isoprenoid pathway | AY043490 |
| 14 | FPPS | Mdo.2964 | Farnesyl pyrophosphate synthase Isoprenoid pathway | AY083165 |
| 15 | Far | Mdo.3011 | (E,E)-alpha-farnesene synthase Isoprenoid pathway | EB111255 |
| 16 | CSL | Mdo.12560 | C-S-lyase Cysteine catabolism | AY347795 |
| 17 | APOX | Mdo.1891 | Ascorbate peroxidase Antioxidant system | CN928974 |
| 18 | GST | Mdo.12372 | Glutathion S-trasnferase Antioxidant system | FE969955 |
| 19 | POX | Mdo.11566 | Peroxidase Antioxidant system | CN913385 |
| 20 | CalS | Mdo.12945 | Callose synthase Wall modification | CN496203 |
| 21 | Pect | Mdo.15511 | Pectin methyl esterase Wall modification | CV628630 |
| 22 | CAD | Mdo.2625 | Cinnamyl alcohol dehydrogenese Wall modification | AF053084 |

TABLE 1-continued list of the target genes according to the invention

| SEQ ID NO. | NAME OF THE GENE | Apple Unigene (NCBI) | Function of the gene | Apple cDNA Accession No. (NCBI) |
|---|---|---|---|---|
| 23 | EDS1 | Mdo.2759 | Disease resistance protein EDS1 Salicylic acid signaling | CN949066 |
| 24 | WRKY | — | WRKY transcription factor 30 Salicylic acid signaling | AY347836 |
| 25 | LOX2 | Mdo.10456 | Lipoxygenase AtLOX2 Jasmonic acid signaling | CN941066 |
| 26 | JAR | Mdo.2326 | Jasmonate resistant 1 Jasmonic acid signaling | CN879199 |
| 27 | ACCO | Mdo.3241 | 1-aminocyclopropene-1-carboxylate oxidase Ethylene signaling | AB086888 |
| 28 | EIN3 | Mdo.12601 | EIN3-BINDING F BOX PROTEIN 1 Ethylene signaling | CV082047 |
| 29 | TuA | Mdo.3499 | Tubulin alpha-1 chain Reference gene | CO065788 |
| 30 | Actin | Mdo.701 | Actin 7 Reference gene | CV151413 |
| 31 | GAPDH | Mdo.1683 | Glyceraldehyde-3-phospate dehydrogenase Reference gene | CN494000 |

Among these genes, genes can be identified the function of which is known but which have never been connected to natural defense mechanisms in Roses, e.g., the CSL gene.

The TuA, Actin and GAPDH genes comprise marker genes the expression level of which is separate from the natural defense stimulation state. These genes are cited herein for exemplary purposes only. Such "reporter" genes enable correction of the specific expression level for each of the target genes.

In the present description, the names used to denote each of the target genes correspond to a recognized international naming system, which are found, in particular, in gene sequence and protein sequence databases, e.g., the UniGene databases proposed by the National Center for Biotechnology Information (NCBI, Bethesda, Md., USA). In this case, reference is preferably made to the UniGene database *Malus domestica*.

The target genes in question are also defined, respectively, by editable sequences using the UniGene accession numbers specified in Table 1.

The target genes according to the invention likewise denote the "variants" or "unigenes" or alleles that correspond to these sequences.

These variants have at least 70%, 80%, 90%, 94%, 95%, 96%, 97%, 98%, 99% or more nucleotide identity with the aforesaid sequences, preferably by aligning sequences over the entire length thereof and by comparing the base identity after alignment.

Such variants can be identified by various methods of the prior art, such as nucleic acid hybridization techniques (e.g., Southern blot, Northern blot, etc.), protein-based methods (e.g., Western blot), PCR technique-based methods, sequencing, bioinformatic analysis (e.g., using a FASTA or BLAST type computer program, using default parameters).

The variants are preferably functional variants, i.e., they encode for proteins having the same biological functions, or at least similar biological functions, in relation to the proteins derived from the aforesaid sequences.

The variants likewise include the sequences or homologous or orthologous genes preferably found in the genera or varieties of Roses, other than *Malus domestica*.

More generally speaking, the variants likewise advantageously include the sequences or homologous or orthologous genes found in any other plant, preferably in any organism belonging to the subkingdom Tracheobionita, more preferably belonging to the spermaphytes, more preferably to the angiosperms, more preferably to the dicotyledons, and more preferably to Rosidea.

The term "orthologous" or "homologous" for a sequence, gene or protein, refers here to the homologous sequence, gene or protein, which is found in another species and has the same function as the sequence, gene or protein of interest, but which (generally) has diverged in sequence from the moment when the species comprising said genes diverged (the genes evolved from a common ancestor via speciation). Such orthologous sequences or genes can thus be identified in other plant species via a sequence comparison technique (e.g., based on sequence identity percentages over the entire sequence or on specific domains) and/or functional analysis.

Such orthologous sequences, for example, have been identified in other genera of the Rose family.

Table 2A below specifies the accession number in the GenBank database, as proposed by the National Center for Biotechnology Information (NCBI, Bethesda, Md., USA), for each of the orthologous sequences identified.

TABLE 2A

Orthologous sequences for the target genes according to the invention

| No. | Name of the gene | Orthologous in *Fragaria* | Orthologous in *Prunus* | Orthologous in *Pyrus* | Orthologous in *Rosa* |
|---|---|---|---|---|---|
| 1 | PR-1 | DV440399 | DN556381 GE653251 | AF195235 | EC586767 |
| 2 | PR-2 | EX682264 | DN554095 | AJ504892 | EC587362 |
| 3 | PR-4 | EX657003 | CB823353 | — | — |
| 4 | PR-5 | DY668082 EX674853 | GE653177 | FK939207 | BI977710 |
| 5 | PR-8 | DY672350 | CV051978 CV052812 | AJ504863 | BI977412 |
| 6 | PR-14 | DY673738 | AM290861 | AF195216 | EC589716 |
| 7 | PR-15 | DY673400 | GR410635 | — | EC586210 |
| 8 | PAL | CO817421 EX684393 | CV046544 | — | — |
| 9 | CHS | AI795452 DY667960 | CB820023 FE969272 | FK939234 | CF349759 |
| 10 | DFR | DY672493 EX661062 | CV046853 CB819555 | DB999982 | — |
| 11 | ANS | CX661854 | BU039495 | FK939239 | BI977949 |
| 12 | PPO | DY667415 EX674603 | CV045870 | AJ504916 | — |
| 13 | HMGR | DY669718 EX659154 | AM290185 FC861452 | — | BQ106200 |
| 14 | FPPS | DY669331 EX660570 | DY644308 | — | BQ104581 |
| 15 | Far | DY675841 | DY646265 | — | CF349900 |
| 16 | CSL | CO817796 | AJ533335 BU047350 | — | — |
| 17 | APOX | CX661243 CX661894 | CV045878 GE653243 | GR957944 | EC586214 BI978785 |
| 18 | GST | DV438230 DV438954 | CB820780 | DB999954 | EC587514 |
| 19 | POX | DY676157 DY670759 | DW341091 GR410510 | DC993457 | EC586635 |
| 20 | CalS | EX687641 | DY633833 | DC993380 | BQ104579 |
| 21 | Pect | DY666714 | BU044880 | — | BQ104257 |
| 22 | CAD | CX662236 | EE488909 | DV440820 | CF349542 |
| 23 | EDS1 | DY673255 | DY652698 FC866180 | — | CF349463 |
| 24 | WRKY | EX687984 | AJ873733 | — | — |
| 25 | LOX2 | DY674691 | BU046906 | — | CF349741 |
| 26 | JAR | DY667416 | FC864077 | — | — |
| 27 | ACCO | CX662198 EX670124 | AJ833064 | DB999960 | EC588379 |
| 28 | EIN3 | DY666956 | EE488205 | — | — |

TABLE 2A-continued

Orthologous sequences for the target genes according to the invention

| No. | Name of the gene | Orthologous in *Fragaria* | Orthologous in *Prunus* | Orthologous in *Pyrus* | Orthologous in *Rosa* |
|---|---|---|---|---|---|
| 29 | TuA | DY671340 DY674254 | BU042671 | — | BQ106089 BQ105408 |
| 30 | Actin | DY668010 EX688327 | DY650839 CV044868 | — | BQ104395 BI977396 |
| 31 | GAPDH | DY667270 DY667095 | DW357797 DW350728 | — | BI978153 BQ104075 |

In the same way, the device according to the invention can be used for studying plants of the *Vitaceae* (vine) family, in particular the species of the genus *Vitis*, and in particular *Vitis vinifera*.

For informational purposes, orthologous sequences corresponding to the target genes, for example, have been identified in *Vitis vinifera*.

Table 2B below specifies the accession number in the GenBank database proposed by the National Center for Biotechnology Information (NCBI, Bethesda, Md., USA) or in the database proposed by Génoscope (Evry, France), for each of the orthologous sequences identified.

TABLE 2B

| Name of the gene | Orthologous in *Vitis vinifera* (Vine) | |
|---|---|---|
| | EST (NCBI) Accession No. | Gene accession No. (Genoscope) |
| PR-1 | EE253686.1 | GSVIVT01037005001 |
| PR-2 | GO652966.1 | GSVIVT01033538001 |
| PR-4 | FG984977.1 | GSVIVT01036279001 |
| PR-5 | EC925003.1 | GSVIVT01019840001 |
| PR-8 | EC965083.1 | GIDVvT00013094001 |
| PR-14 | DT021081.1 | GIDVvT00010281001 |
| PR-15 | EC968706.1 | GSVIVT01031082001 |
| PAL | CN006882.1 | GSVIVT01025703001 |
| ANS | CF209704.1 | GSVIVT01019892001 |
| CHS | EV241635.1 | GSVIVT01032968001 |
| DFR | EE082741.1 | GSVIVT01009743001 |
| PPO | CF215866.1 | GIDVvT00029382001 |
| HMGR | EC937417.1 | GSVIVT01013435001 |
| FPPS | EC962139.1 | GSVIVT01014738001 |
| Far | DT009302.1 | GSVIVT01000402001 |
| AIII | FC061753.1 | GSVIVT01001413001 |
| APOX | CF211522.1 | GSVIVT01015626001 |
| GST | EE099033.1 | GSVIVT01027961001 |
| POX | DT007525.1 | GSVIVT01009107001 |
| CAD | CF511159.1 | GSVIVT01025239001 |
| CalS | EE095949.1 | GSVIVT01025362001 |
| Pect | EE076956.1 | GSVIVT01011699001 |
| EDS1 | | GSVIVT01007860001 |
| WRKY | | GSVIVT01028718001 |
| LOX2 | EE107237.1 | GSVIVT01025339001 |
| JAR | EC983478.1 | GSVIVT01027057001 |
| ACCO | CF511696.1 | GSVIVT01006065001 |
| EIN3 | CF214803.1 | GSVIVT01015548001 |

The target genes according to the invention are likewise defined by the sequences SEQ ID No. 1 to 28, which correspond to the respective cDNAs thereof, or by the variants of said sequences according to the above definition.

The corresponding sequences are likewise available in the GenBank (NCBI) databases, by way of the accession numbers specified in Table 1.

For the notion of a "variant", reference may be made to the definitions established above.

The target genes according to the invention are also denoted by the proteins that they encode, respectively.

The peptide sequences corresponding to the target genes are specified, for example, in the UniGene *Malus domestica* databases, and can be obtained by way of the accession numbers specified in Table 1.

According to a preferred embodiment, the device according to the invention comprises means for determining and/or studying the expression level of at least two genes in the aforesaid groups (a), (b), (c), (e), (f), (g), (h) and (i).

This preferred embodiment offers the following advantages, in particular:

if the target genes of a single group are co-regulated (this is especially the case of signaling pathway genes that are often activated temporarily), they may have a sequential expression, and the fact of choosing a single one of them increases the risk of coming to the conclusion that there is an absence of modulation of this pathway (if the samplings are not carried out at the correct time for a given gene);

if the target genes of a single group are not co-regulated (this is particularly the case of PR proteins, as well as enzymes of the phenylpropanoide pathway, for the PPO gene on the one hand, PAL on the other hand, and finally the CHS, DFR and ANS group), it then becomes arbitrary to choose only one of them;

it enables the expressions of several target genes to be followed in each group, the redundancy of information regarding the expression level of more than one target gene belonging to a given group further increases the reliability of the results.

Specifically, among the above target genes, the device according to the invention advantageously enables the study and/or analysis of the expression of at least one of the following combinations of genes:

for group (a), at least one of the following genes: PR-1, PR-2, PR-4 or PR-8, combined with at least one of the following genes: PR-5, PR-14 or PR-15;

for group (b), the gene PAL and at least one of the following genes: CHS, DFR or ANS, and the gene PPO, for group (c), at least one of the following genes: HMGR and/or Far, and the gene FPPS, for group (e), the gene APOX and at least one of the following genes: GST and/or POX.

According to a preferred embodiment, the combination of target genes studied in the device according to the invention is as follows: PR-1, PR-2, PR-4, PR-5, PR-8, PR-14, PR-15, PAL, CHS, DFR, ANS, PPO, HMGR, FPPS, Far, CSL, APOX, GST, POX, CalS, Pect, CAD EDS1, WRKY, LOX2, JAR, ACCO and EIN2.

Device According to the Invention, and Means for Determining and/or Studying the Expression Level of a Combination of Target Genes According to the Invention General Features of the Device According to the Invention The present invention includes the device or tool, advantageously in the form of a package or "kit" for determining and/or studying the natural defense stimulation state in a sample of plants or plant portions, in particular from Rosaceae seedlings and also in particular from apple seedlings.

Such detection and quantification devices are based on the preparation of a reaction mixture intended to contain the biological markers of interest and the appropriate specific reagents, under suitable conditions and for a time period sufficient to enable the marker and the specific reagent thereof to interact and to bond, and to thus form a complex that can be removed and/or detected in said reaction mixture.

To achieve this, the device according to the invention contains suitable means for detecting any detectable, measurable and/or quantifiable biological marker in the plant or plant portion studied, which corresponds directly or indirectly to the expression level of each of the selected genes.

According to a preferred embodiment, nucleic acids (e.g., mRNAs or cDNAs) or polypeptides comprise the expression markers for each of the target genes of interest.

The detection method of the device in accordance with the invention is then advantageously based on the detection of mRNAs, cDNAs and/or marker proteins in the sample.

The detection means thus advantageously include reagents or ligands or agents or compounds or compositions including, or consisting of a set of specific reagents, each of which is capable of bonding specifically with a biological marker of interest, advantageously of the nucleic acid or protein type, which is representative of the expression level of one of the target genes.

The reagents suitable for bonding with nucleic acid type markers, in particular an mRNA or a cDNA, include the nucleic acids of complementary sequences.

For example, reagents suitable for detecting/quantifying nucleic acid markers can include (i) oligonucleotides (marked or unmarked) attached to a substrate, (ii) marked oligonucleotides not attached to a substrate, (iii) a pair of primers for a PCR technique or the like.

Reagents suitable for detecting/quantifying marker proteins include antibodies, antibody derivatives, antibody fragments or the like.

The package or kit according to the invention also contains any appropriate additional compound useful for implementing the invention.

For example, the device can contain fluids or media for hybridizing complementary nucleic acids or for binding an antibody with a protein.

Generally speaking, the devices in question, for example, include a plurality of specific reagents that are capable of detecting the expression of the target genes according to the invention, which can be associated with control samples, microtitration plates, Eppendorf tubes, an instruction manual, etc.

The elements constituting the device according to the invention are presented in greater detail below.

Means for Determining the Expression Level of the Target Genes in the Device According to the Invention The device according to the invention therefore comprises means for quantifying and/or determining the expression of the aforesaid target genes.

Thus, any means for detecting and/or quantifying a nucleic acid or protein in a biological sample can be used here.

In this case, the means for determining the expression level or profile of each target gene are advantageously chosen from among:

(i) the nucleic acid fragments selected from among those capable of specifically hybridizing with the mRNAs expressed by each of the target genes or with the corresponding cDNAs, or with fragments of said mRNAs or said cDNAs, and/or (ii) the antibodies selected from among those capable of bonding specifically with the expression products of each of the target genes, of said mRNAs or said cDNAs, or with the fragments of said expression products, i.e., in particular a protein or polypeptide.

In practice, quantification of the expression level of each target gene includes the following steps:

(a) preparation of a sample of nucleic acids (mRNAs and/or cDNAs) or proteins, from a plant or plant portion, and (b) hybridizing the mRNAs/cDNAs and/or the proteins of the sample prepared, with determination means including one or more reference reagents (polynucleotides of the probe or primer type, or antibodies in particular) contained in the device according to the invention.

The sample of nucleic acids and/or proteins can be obtained from a portion of the plant (e.g., a leaf, roots, etc.), or from the entire plant (e.g., seeds or seedlings), or from a plurality of plants or plant portions, such as a batch of plants or leaves.

In this way, during a first phase, plant portions are sampled, and optionally placed in common, prior to the steps of isolating the sample from nucleic acids or proteins, or the detection steps.

The sample of nucleic acids or proteins is preferably extracted from the cells, e.g., by using standard methods for extracting nucleic acids or proteins.

Raw extracts or samples of raw tissues, e.g., like homogenized plant tissues, can also be used as a sample of nucleic acids or proteins, wherein the transcribed markers or protein markers are detected and/or quantified.

Using the sample prepared, the device according to the invention enables the expression level to be quantified in terms of mRNAs (or corresponding cDNAs) or in terms of specific proteins corresponding to the aforesaid target genes.

According to a preferred embodiment, the device according to the invention is suitable for studying the expression of target genes on the basis of nucleic type markers.

In this case, the device can be made in the form of a DNA chip, also denoted by the names gene chip or biochip, or by the terms "DNA chip", "DNA microarray" or "biochip".

The sample of nucleic acids is preferably an mRNA or complete RNA or cDNA sample.

The cDNAs can be optionally amplified using any method based on chain polymerization reactions, prior to hybridization with the reference polynucleotide(s); alternatively, these cDNAs are not amplified.

For evaluating the transcription level of the target genes in question, the determination means, for example, can be based on (i) quantitative PCR-type amplification methods, preferably the quantitative RT-PCR method, or (ii) nucleic acid hybridization methods, e.g., in the form of DNA chips or "microarray hybridization".

Quantitative PCR (qPCR or QPCR) can be carried out using conventional equipment and techniques, which are well-known to a person skilled in the art, as described, for example, in S. A. Bustin (Ed.), et al., A-Z of Quantitative PCR, IUL Biotechnology Series, No. 5, 2005.

One possible method is reverse transcription with quantitative PCR or RT-qPCR (see Czechowski et al., 2004, Plant J. 38, 366-379; Czechowski et al., 2005, Plant Physiol. 139, 5-17; Vandesompele et al., 2002, Genome Biol. 3(7): research 0034.11).

This measurement technique enables detection of a relative or absolute expression level of the mRNA of the target genes in the sample.

Such a device using a qPCR technique is described in greater detail herein below, and a practical application is presented in the examples.

Alternatively, the determination is conventionally obtained by placing the sample of nucleic acids in contact with a substrate onto which are attached a plurality of polynucleotides comprising sequences (e.g., at least 7, 10, 15, 20, 25, 30, 40, 50, 100, 500 or more nucleotide residues or bases) complementary to the sequence of each of the nucleic acid or polynucleotide markers.

These attached polynucleotides comprise a sequence having a hybridization specificity under specific conditions for forming a hybridization complex with the nucleic marker of a target gene.

According to the present invention, the specific marker of the target gene can be (i) a nucleotide sequence contained in a messenger RNA derived from the target gene (reference is then made to a specific mRNA of the target gene), (ii) a nucleotide sequence contained in a complementary DNA obtained by reverse transcription of said messenger RNA (reference is then made to a specific cDNA of the target gene), or else (iii) a nucleotide sequence contained in a complementary RNA obtained by transcription of said cDNA as described previously (reference is then made to a specific cRNA of the target gene).

If the various polynucleotide markers attached can be separately detected on a single substrate (e.g., by using various chromophores or fluorophores, or attached at various selected positions of said substrate), the expression levels of a plurality of markers can be studied simultaneously on said single substrate.

Appropriate methods for detecting and quantifying by means of polynucleotide-bonded chips are described in the prior art and, for example, can be found in: Applications of DNA Microarrays in Biology. R. G. Stoughton (2005), Annu. Rev. Biochem. 74:53-82, or in David Bowtell and Joseph Sambrook, DNA Microarrays: A Molecular Cloning Manual, Cold Spring Harbor Laboratory Press, 2003, ISBN 0-870969-625-7.

In order to construct such a DNA-bonded chip, nucleic acid molecules are attached to a solid substrate at known locations or "addresses".

The bonded nucleic acid molecules are complementary to the nucleotide sequences of the invention, and in particular to the sequences SED ID No. 1 to 28, and the location of each nucleic acid on the chip is known.

These chips having bonded polynucleotides can, for example, be made by using (i) presynthesized probe deposition methods, (ii) in situ synthesis or (iii) photolithography.

The methods for generating marked polynucleotides and for hybridizing with these DNA chips are well-known in the prior art (see, for example, US 2002/0144307, and Ausubel et al., EDS (1994) Current Protocols in Molecular Biology, Current Protocols (Greene Publishing Associates, Inc., and John Wiley & Sons, Inc., New York, 1994 Supplement)).

In the device according to the invention, the hybridization between two nucleic acids is advantageously implemented under stringent hybridization conditions.

According to a complementary or alternative embodiment, the device according to the invention is suitable for studying the expression of target genes on the basis of protein-type markers.

In this case, the determination means, for example, can be based on techniques using: (i) antibodies (radio-labeled, labeled with a chromophore, a fluorophore or a polymer chain or enzyme), (ii) antibody derivatives (e.g., an antibody paired with a substrate or a protein or a ligand of a pair of ligand proteins (e.g., biotin-streptavidin), or (iii) antibody fragments (e.g., a single-chain antibody, a chain of isolated antibodies, etc.) which bond specifically with a marker protein or a fragment thereof, or optionally a marker protein that has undergone all or part of these normal post-translational modifications.

The expression level, obtained by implementing the device according to the invention, can be expressed by an arbitrary unit, which reflects the quantity of messenger RNA transcribed for each gene of interest, such as the intensity of a radioactive or fluorescent signal emitted by the cDNA material generated by PCR analysis of the messenger RNA content of the sampled studied, including real-time PCR analysis techniques of the messenger RNA contained in the sample.

Alternatively, this expression level can be expressed as an arbitrary unit, which reflects the quantity of marker proteins detected in the sample studied, such as the intensity of a radioactive or fluorescent signal emitted by a specific marked antibody of the protein of interest.

Also alternatively, the value obtained may consist of a concentration of proteins of interest, which can be measured by various protein detection methods known in the prior art, such as ELISA, MALDI-TOF (for "Matrix-Assisted Laser Desorption Ionization Time-of-Flight") SALDI-TOF (for "Surface-Assisted Laser Desorption Ionization Time-of-Flight") or Western Blot.

Alternatively still, this gene expression value can be expressed as a relative arbitrary unit, corrected by the expression level of one or more so-called "reporter" reference genes), which are not modified in the sample by the natural defense stimulation state.

In the latter case, the expression value for each target gene can be expressed as the difference (deltaCT) between (i) the quantity of an mRNA or a protein comprising a biological marker and (ii) the quantity of an mRNA or a non-marker protein present in the sample, which, for example, was chosen from among the genes corresponding to tubulin, actin, GAPDH or ubiquitin.

In this regard, reference can again be made to the following documents: Livak et al. (2001, Methods 25:402-408) or Vandesompele et al. (2002, Genome Biol. 3(7): research 0034.1-0034.11).

Two preferred devices are detailed below, without, however, constituting a limitation in the techniques capable of being used for the device according to the invention.

Biological Quantification of Marker Transcripts Via Amplification of Nucleic Acids The device according to the invention advantageously includes means for determining the expression level of the aforesaid combination of target genes, by amplifying transcribed nucleic acids (mRNAs or cDNAs) as part of a so-called quantitative PCR technique.

The chain polymerization reaction (PCR or "Polymerase Chain Reaction") is a highly effective method for such quantification of nucleic acids constituting biological markers.

In order to implement such amplifications of nucleic acids for the purpose of quantifying the biological markers of interest, the determination means according to the invention include a set of primer pairs, each primer pair being capable of specifically bonding with and amplifying a target mRNA or target cDNA.

According to this technique, the complete RNAs are extracted and purified and the messenger RNAs contained in the extract are advantageously converted, in a first phase, to complementary DNAs (cDNAs), using reverse transcriptase.

A pair of primers capable of hybridizing specifically with each of the marker nucleic acids can be designed using any appropriate method known in the prior art.

The two primers are chosen from the sense and antisense strands, respectively, so as to enable amplification of a DNA fragment.

Degenerate or specific pairs of primers for amplifying the nucleic acids of SEQ ID Nos. 1 to 28 (or a portion or variant of said sequences) can be synthesized from said sequences, or variants of said sequences.

The sense and antisense primers advantageously include at least 15 nucleotides and have an identity of at least 80%, preferably 90%, and more preferably 95%, and yet more preferably 100% with the sequence of the target genes, or with the complementary sequence thereof, or with the aforesaid cDNAs. Examples of such primers specific to each of the sequences SEQ ID Nos. 1 to 28 are denoted by the sequences SEQ ID Nos. 32 to 87 (Table 3 in the Example part).

In addition, examples of specific primers of the reference genes SEQ ID no. 29 to 31 are noted by the sequences SEQ ID Nos. 88 to 93 (Table 3).

The determination means also comprise polymerases, preferably the Taq polymerase, but this can be any other enzyme having a polymerase activity and usable under PCR operational conditions.

During the course of the amplification reaction, the reaction product is detected, which is also denoted by the name of amplimere or amplicon.

The quantity of mRNAs transcribed for each target gene is measured by means enabling implementation of the so-called quantitative PCR or QPCR method. Quantitative PCR enables quantification of an intimal quantity of DNA, cDNA or RNA in the sample prepared.

To achieve this, said method is based on the detection of a fluorescent reporter compound the signal intensity of which increases when the product of the PCR accumulates with each amplification cycle.

The determination means thus comprise fluorescent reporter compounds, i.e., compounds which bond to the double-stranded DNA (e.g., in the case of a SYBR Green I technique) or specific probes (e.g., in the case of a TaqMan® technique, a HybProbes (FRET) technique or hybridization of 2 probes, a Molecular Beacons technique, and a Scorpion or Scorpion primer technique).

In order to implement this PCR technique within the scope of the present invention, reference can be made to the overall reviews concerning PCR techniques and to the instructions of manufacturers and distributors of reagents and thermocyclers, and in particular to the fact sheet entitled "Quantitation of DNA/RNA Using Real-Time PCR Detection" published by Perkin Elmer Applied Biosystems (1999) and to PCR Protocols (Academic Press, New York 1989).

Use can also be made of the information presented in the following documents: Livak et al. (2001, Methods 25:402-408) and Vandesompele et al. (2002, Genome Biol. 3(7): research 0034.1-0034.11).

One of the advantages of the QPCR detection method is that the analysis of the PCR products is carried out directly during the PCR cycles, by reading the fluorescence obtained during the cycles. It is therefore not necessary to work with the PCR products, which constitutes a risk of contamination with regard to subsequent analyses. This detection advantageously occurs in full PCR exponential phase, and not at the final moment; this detection principle is therefore more sensitive and specific.

Furthermore, quantification of the number of initial targets in the reaction is very low and reproducible. Detection of the PCR product occurs during the PCR cycles.

A particular embodiment for quantifying such biological markers, on the basis of a device implementing a quantification technique using amplification, is disclosed in the following examples.

Biological Quantification of Marker Proteins

According to another embodiment of the invention, the means for determining the expression levels of the target genes include means for measuring the quantity of marker proteins, or fragments of marker proteins present in the sample prepared.

To achieve this, the corresponding determination means advantageously include a combination or set of antibodies, each antibody being specifically directed against a protein or a protein fragment, comprising a marker representative of the expression of one of the aforesaid target genes according to the invention.

The antibodies in question can be polyclonal or preferably monoclonal.

Antibodies can be used intact, or as fragments or derivatives of such antibodies (e.g., Fab or F(ab')$_2$).

A variant technique can be used to determine and/or quantify a protein-type biological marker, by way of a given antibody.

For example, such techniques include, but non-limitatively, radioimmunoassays (or RIAs), immunoradiometric assays (or IRMAs), enzymoimmunoassays (or EIAs), enzyme-labeled immunosorbent assays (or ELISAs), fluoroimmunoassays or FIAs, or immunofluorometric assays or IFMAs, luminoimmuno assays or LIAs or immunoluminometric assays or IFLAs, or Western blot tests.

In order to obtain antibodies and implement the ELISA and radioisotope techniques in particular, reference may be made to the manual "Antibodies, A Laboratory Manual" (Cold Spring Harbor Press (1988)).

A person skilled in the art would be entirely capable of adapting the known protein/antibody detection and/or quantification methods for use with the device according to the invention.

Plant or Plant Portion Studied by Means of the Device According to the Invention The device according to the invention proves to be particularly advantageous for studying plants, or plant portions belonging to the Rosaceae or Rose family.

This device will be particularly advantageous in studying plants or plant portions chosen from among one of the following sub-families: Amygdaloideae (peach tree family), Maloideae (apple tree family), Rosoideae (rose family) and Spiraeoideae (spirea family).

More specifically, the device according to the invention will be advantageous for studying plants or plant portions chosen from among the following genera: *Acaena, Adenostoma, Agrimonia, Alchemilla, Amelanchier, Aphanes, Ammonia, Aria, Aruncus, Bencomia, Brachycaulos, Cercocarpus, Chaenomeles, Chamaebatia, Chamaebatiaria, Chamaemeles, Chamaemespitus, Chamaerhodos, Cliffortia, Coleogyne, Coluria, Cormus, Cotoneaster, Cowania, Crataegus, Cydonia, Datibarda, Dichotomanthes, Docynia, Docyniopsis, Dryas, Duchesnea, Eriobotrya, Eriolobus, Exochorda, Fallugia, Filipendula, Fragaria, Geum, Gillenia, Guamatela, Hagenia, Hesperomeles, Heteromeles, Holodiscus, Horkelia, Horkelielia, Ivesia, Kageneckia, Kelseya, Kernia, Leucosidea, Lindleya, Luetkea, Lyonothamnus, Maddenia, Malacomeles, Malus, Margyricarpus, Mespilus, Neilia, Neviusia, Nuttalia, Oemieria, Orthurus, Osteomeles, Pentactina, Peraphyllum, Petrophytum, Photinia, Physocarpus, Polylepis, Potanina, Potentilla, Poterium, Prinsepia, Prunus, Pseudocydonia, Purshia, Pyracantha, Pyrus, Quillaja, Rhaphiolepis, Rhodotypos, Rosa, Rubus, Sanguisorba, Sarcopoterium, Sibbaldia, Sibiraea, Sorbaria, Sorbus, Spenceria, Spiraea, Spiraeanthus, Stephanandra, Taihangia, Tetraglochin, Torminalis, Vauquelinia, Waldsteinia, Xerospiraea.*

The device according to the invention is preferably suitable for studying plants or plant portions belonging to one of the following species: *Prunus armeniaca, Prunus dulcis, Prunus avium, Cydonia oblongs, Rosa canina, Fragaria, Rubus idaeus, Rubus fruticosus agg, Mespilus germanica, Prunus persica, Rubus chamaemorus, Pyrus communis, Malus domestica, Prunus domestics.*

More preferably, the device is intended for studying the apple or *Malus domestica*.

In this case, the present device can be used for all apple varieties, and in particular the following varieties: Golden Delicious, MM106 and Evereste.

Method Using the Device According to the Invention

Generally speaking, the device according to the invention can be used for studying the natural defense stimulation state of a plant or plant portion (or a plurality of plants or plant portions).

In practice, the expression profile of a plurality of samples of nucleic acids and/or proteins, derived from a plurality of plants and/or plant portions, is determined by means of one or a series of devices according to the invention. This step enables account to be taken of possible variations in the expression of the genes between the plants and/or plant portions, and to thus obtain reliable results.

In parallel, control samples are advantageously studied and analyzed using the devices according to the invention.

For example, the control samples (or reference samples) can be obtained from plants or plant portions the natural defense stimulation state of which is known.

Thus, the control samples can be derived from plants or plant portions that are untreated or unstressed, or that have been previously subjected to a natural defense-stimulating compound and/or a stress.

Next, in order to determine the natural defense stimulations state of plants of interest (having an unknown natural defense stimulation state), the samples obtained from these plants or plant portions will be compared with samples derived from plants or plant portions the natural defense stimulation state of which is known.

In this way, several samples can be analyzed by means of the device according to the invention, such as samples of nucleic acids and/or proteins derived (i) from plants or plant portions the natural defense stimulations state of which is known, (ii) from plants or plant portions the natural defense stimulation state of which is unknown, (iii) from plants or plant portions previously subjected to at least one biotic and/or abiotic stress, or (iv) from plants or plant portions previously subjected to at least one product for verifying or researching a natural defense-stimulating effect.

The device according to the invention can thus be implemented in a set of methods, some of which are presented in detail herein below.

Method for Identifying an Expression Profile of a Combination of Target Genes

A first use of the device according to the invention is for identifying the expression profiles of the aforesaid combination of target genes, also denoted as "signatures", which would enable the natural defense stimulation state of plants to be determined or at least evaluated.

The method for identifying an expression profile for a combination of target genes includes the following steps:
(i) determining the expression profile of a combination of target genes by means of the device according to the invention, for a set of plants, or plant portions, advantageously belonging to the Rosaceae family, the natural defense stimulation state of which is known, and then
(ii) determining an expression profile of interest for said combination of target genes, which corresponds to a specific natural defense stimulation state for said plants or plant portions, using data derived from step (i).

At least one quantitative expression value for each of the biological markers used is obtained by means of the device according to the invention and during step (i).

The obtainment of a plurality of quantitative values for each biological marker used enables a more accurate projection of the natural defense stimulation state.

These quantifications are implemented with respect to the samples of plants or plant portions the natural defense stimulation state of which is known, which samples are advantageously chosen from among:

the samples of plants or plant portions not subjected to a stress and/or a natural defense-stimulating product; or the samples of plants or plant portions subjected to a stress; or the samples of plants or plant portions subjected to a natural defense-stimulating product.

For example, to obtain samples representative of a biotic stress, hydrogen peroxide can be sprayed onto the plants or plant portions.

To obtain negative controls, water purified by reverse osmosis can be sprayed on the plants or plant portions.

To obtain samples representative of fire blight protection, Bion® can be applied to the plants or plant portions.

Step (ii) consists in comparing the quantitative values obtained in step (i) for each biological marker.

In this way, the reference expression values for each of the target genes can be determined.

Said values together comprise "a reference profile" that is suitable for distinguishing and/or identifying and/or determining a modification in the natural defense stimulation state.

Each reference profile determined for said combination of biological markers is thus correlated to a natural defense stimulation state.

According to an advantageous embodiment, for the combination of biological markers according to the invention, the reference profiles can be predetermined by carrying out a method comprising the following steps:

a) providing at least one collection of samples of plants or plant portions, the natural defense stimulation state of which is determined;

b) quantifying, by means of the device according to the invention, the expression level of said biological markers for each sample provided in step a), whereby a series of quantitative values for the biological markers of said sample collection is obtained;

c) determining, from said series of quantification values obtained at the completion of step b), a correlation between a specific expression profile for said biological markers and a specific natural defense stimulation state.

Certain advantageous expression profiles obtained by means of the device according to the invention are presented in the examples.

Method for Determining or Evaluating the Natural Defense Stimulation State

The device according to the invention likewise has the advantage of being capable of being implemented as part of a method for analyzing the natural defense stimulation state of a plant or plant portion.

The method for determining or evaluating the natural defense stimulation state of a plant includes the following steps:

(i) taking a sample from the plant or from said plant portion, advantageously belonging to the Rosaceae family, which has optionally undergone any treatment of interest (e.g., a stress or natural defense-stimulating treatment), (ii) determining the expression profile of a combination of target genes in said sample taken in step (i), by means of the device according to the invention, (iii) comparing the expression profile obtained in step (ii) with a reference expression profile, (iv) determining or evaluating the natural defense stimulation state of said plant or said plant portion, using said expression profile obtained in step (ii).

The expression profile obtained in step (ii), by means of the device according to the invention, is compared to a reference expression profile, which corresponds to the values observed for samples of plants or plant portions advantageously chosen from among:

the samples of plants or plant portions subjected to stress or a natural defense stimulator; or the samples of plants or plant portions not subjected to stress (e.g., *E. amylovora*); or the samples of plants or plant portions subjected to a natural defense stimulator (e.g., Bion®).

In particular, the overexpression of at least one target gene, and more preferably a combination of target genes in a studied sample, in comparison with samples of plants or plant portions not subjected to stress or a natural defense stimulator, enables identification of the plants or plant portions having an activated or induced natural defense stimulation state.

In the same way, the constant expression of at least one target gene, and more preferably a combination of target genes in a studied sample, in comparison with samples of plants or plant portions subjected to stress or a natural defense stimulator, enables identification of the plants or plant portions having an activated or induced natural defense stimulation state.

Method for Selecting a Substance Having the Property of Modulating the Natural Defense Stimulation State There is a need for new natural defense-stimulating agents, and for reliable and easy methods for screening a large number of biological or chemical compounds for the use thereof as natural defense stimulating agents.

There is likewise a need to verify the biological activity of compounds or compositions presented as natural defense stimulators.

The device according to the invention comprises a particularly advantageous tool for identifying such biological or chemical compounds, or such compositions containing said biological or chemical compounds, which are capable of stimulating the natural defenses of a plant or plant portion belonging, advantageously, to the Rosaceae family.

The tool according to the invention in particular makes it possible to screen any biological or chemical active compound or active composition used in the field of agriculture, preferably arboriculture and more preferably in the field of *Maloideae*.

The identification of such a supplementary effect would make it possible to avoid redundant treatments (in particular by applying two compounds activating the same defense mechanisms) and to limit the negative interactions (some NDS products have antagonistic effects with regard to the molecular pathways that they regulate).

The method for implementing the device according to the invention advantageously includes the following steps:

(i) placing one or more biological or chemical compounds, or compositions including one or more biological or chemical compounds in contact with a plant or plant portion (advantageously belonging to the Rosaceae family.

(ii) determining the expression profile of the combination of target genes in a sample taken from said treated plant or said treated plant portion subsequent to step (i), by means of the device according to the invention, (iii) comparing the expression profile obtained in step (ii) with a reference expression profile, in order to determine or evaluate the natural defense stimulation state in said sample, (iv) positively selecting said substance if the comparison in step (iii) shows that said substance tested in step (i) modulates the natural defense stimulation state of said plant or plant portion.

In step (i), any biological or chemical compound or any compound including one or more biological or chemical compounds can be placed in contact with the plants or plant portions.

At least two different compounds and/or compositions can be placed in contact, simultaneously or consecutively, with the plants or plant portions.

Each compound or composition is preferably placed in physical contact with one or more individual plants.

This contact can likewise be carried out by various means, such as spraying, brushing, applying solutions or solids in or on the ground, in the gaseous phase surrounding the plants or plant portions, by immersion, etc.

The compounds or compositions tested can be solid, liquid, semi-solid or gaseous.

The compounds or compositions tested can be artificially synthesized or natural, such as proteins, protein fragments, volatile organic compounds, plants or animals or extracts of micro-organisms, metabolites, sugars, fats and oils, micro-organisms such as viruses, bacteria, fungi, etc.

The biological compound or composition also includes, or consists of one or more micro-organisms or one or more plant extracts.

The expression profile obtained in step (ii) by means of the device according to the invention is compared according to a previously described method, i.e., for example with a reference expression profile which corresponds to the values observed for samples of plants or portions of plants advantageously chosen from among:

the samples of plants or plant portions not subjected to a stress or natural defense stimulator; or the samples of plants or plant portions subjected to a stress (e.g., *E. amylovora*); or the samples of plants or plant portions subjected to a natural defense stimulator (e.g., Bion®).

In particular the overexpression of at least one target gene, and more preferably a combination of target genes in a studied sample, in comparison with samples of plants or plant portions not subjected to a stress or natural defense stimulator, enables identification of the plants or plant portions having a natural defense stimulation state due to the action of the tested compound or tested composition.

For example, the overexpression of the combination of target genes PR-1, PR-2, PR-4, PR-5, PR-8, PR-14, HMGR, Far, CSL, POX, Pect, EDS1 and WRKY enables selection of a substance having the property of generating a natural defense stimulation state of a plant or plant portion belonging to the Rosaceae family, which ensures protection against biotic stresses.

This expression profile preferably enables selection of a substance having the property of generating a natural defense stimulation state of a plant or plant portion belonging to the Rosaceae family, which ensures protection against *Erwinia amylovora*.

In particular, for each of the aforesaid target genes, this overexpression consists of a relative overexpression level (advantageously in relation to a water treatment), which is greater than 3 (or $\log_2$(relative expression)>1.58).

In the same way, the constant expression of at least one target gene, and more preferably a combination of target genes in a studied sample, in comparison with samples of plants or plant portions subjected to a natural defense stimulator, enables identification of plants or plant portions having a natural defense stimulation state due to the action of the tested compound or tested composition.

The treated plant or plant portion can optionally be simultaneously subjected to an abiotic stress (environmental), so as to study the effect of stressful cultivating conditions on the effectiveness of the natural defense stimulators.

The tool according to the invention can make it possible to select and distinguish between direct-stimulating compounds and potentiating compounds.

To achieve this, for example, the change in the expression profile of the genes following application of a biotic stress can be studied, with or without prior application of a compound or composition of interest.

The overexpression of a combination of target genes in a sample after application of biotic stress, in comparison with samples of plants or plant portions not subjected to such a biotic stress, enables identification of the potentiating compounds (or at least those capable of having such a potentiating effect).

Method for Selecting a Plant or Plant Portion

The present invention likewise relates to the identification and selection of plants advantageously belonging to the Rosaceae family, and having a particular natural defense stimulation state, whether said state is obtained:

(a) naturally (by crossing or using natural variations) or artificially (by inducing variations, e.g., by transgenesis of the plants or plant portions, or by mutagenesis by using one or more mutagen genes); and/or (b) following the application of a natural defense-stimulating compound or composition; and/or (c) following the application of one or more biotic and/or abiotic stress(es).

As a matter of fact, the device according to the invention comprises an advantageous tool for selecting a plant preferably belonging to the Rosaceae family, having a natural defense stimulation state capable of giving same improved resistance to at least one biotic and/or abiotic stress of interest.

A method for selecting a plant or plant portion having an improved natural defense stimulation state (and therefore strengthened resistance to biotic and/or abiotic stresses), can include the following steps:

(i) applying the stress or stresses and/or the natural defense stimulators to a plant or plant portion advantageously belonging to the Rosaceae family, (ii) determining the expression profile for a combination of target genes in a sample taken from said plant or said plant portion, by means of the device according to the invention, (iii) comparing the expression profile obtained in step (ii) with a reference expression profile, in order to determine or evaluate the natural defense stimulation state in said sample, (iv) positively selecting said plant if the comparison of step (iii) shows that said plant or plant portion has a natural defense stimulation state capable of giving same improved resistance to at least one biotic and/or abiotic stress of interest.

The plant or plant portion selected in step (iv) advantageously comprises a particular natural defense stimulation state, in the presence of natural defense-stimulating agents and/or biotic stresses and/or abiotic stresses.

The expression profile obtained in step (ii), by means of the device according to the invention, is compared according to a previously described method, i.e., for example with a reference expression profile which corresponds to the values observed for samples of plants or plant portions advantageously chosen from among:

samples of plants or plant portions not subjected to a stress or natural defense stimulator;

samples of plants or plant portions subjected to a natural defense stimulator; or samples of plants or plant portions subjected to a stress.

The overexpression of at least one target gene, and more preferably a combination of target genes in a studied sample, in comparison with samples of plants or plant portions subjected to a stress or natural defense stimulator, enables identification of the plants or plant portions having a natural defense stimulation state capable of having improved resistance to at least one biotic stress and/or abiotic stress of interest.

The device according to the invention thus enables the genotypes to be screen for their reactivity to NDS products.

SEQUENCES

SEQ ID Nos. 1 to 31: sequences of the cDNAs derived from the target genes and reference genes;

SEQ ID Nos. 32 to 93: sequences of PCR primers for amplifying the sequences SEQ ID Nos. 1 to 31.

FIGURES

FIG. 1: Protection effectiveness of 10 NDS candidates against *E. amylovora* on apple seedlings. Water and Phantomycin (Plantom.) are used as negative and positive controls, respectively.

RC: growth regulator; Eclairciss: thinners; Representation in box plots, the latter indicating the confidence intervals of the medians (P=0.05); At least six biological repetitions of 10 seedlings of 2 separate experiments.

Figure 2:
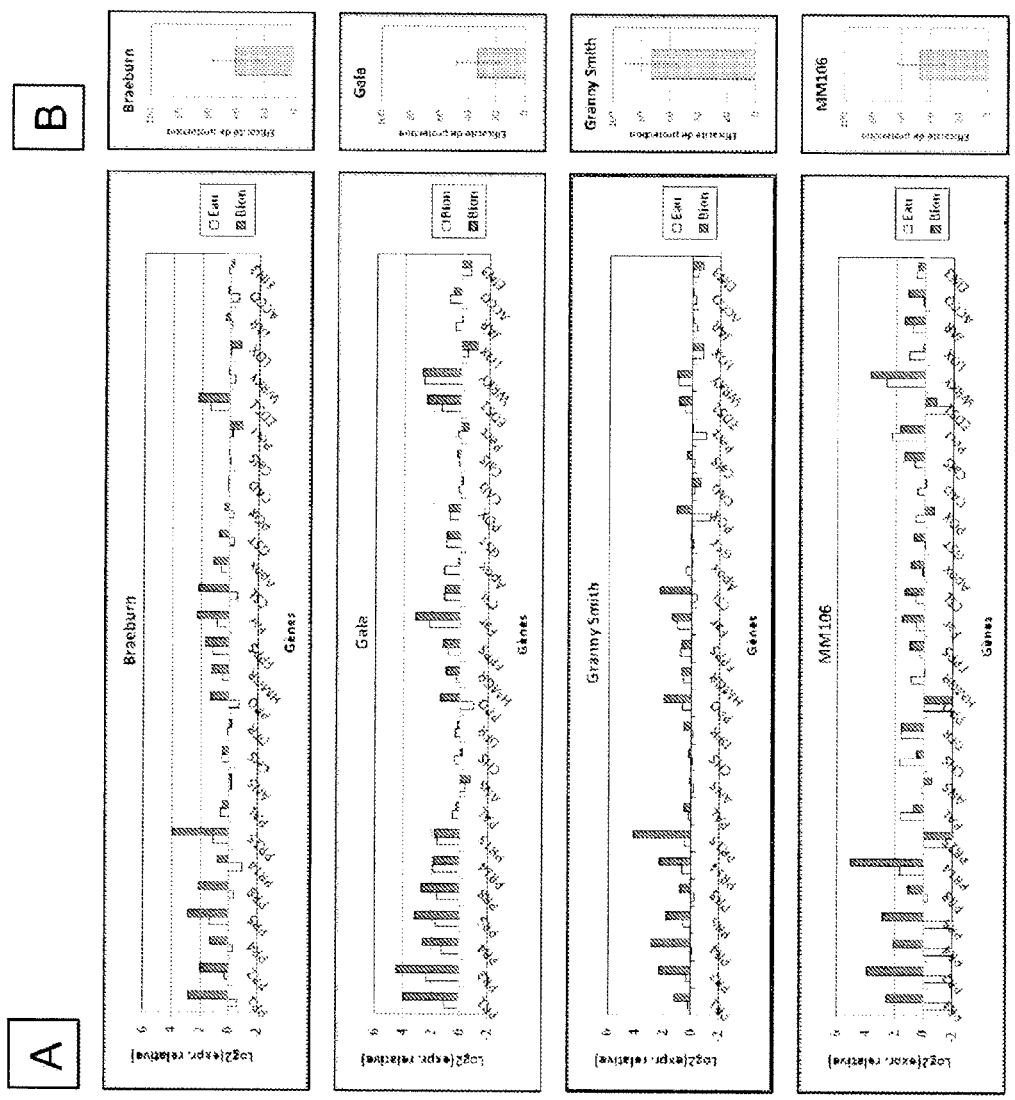

FIG. 2: A) Modulation of the expression of the 28 genes of the tool in leaves of 4 varieties of apple (grafted maiden trees) 3 days after treatment with Bion or water. Differences in expression relative to a sample taken on J0 from untreated plants of each genotype. One biological repetition. B) Average protection effectiveness against fire blight carried out in parallel (n=12).

EXAMPLE

Material

Device According to the Invention

Ready-to-use 96-well microtitration plate containing the primer pairs SEQ ID Nos. 32 to 93 for (i) the 28 target genes SEQ ID Nos. 1 to 28 and (ii) the 3 reference genes SEQ ID Nos. 29 to 31, (distributed in three wells for each pair) in dehydrated form (evaporation for one night at 60° C.) and in sufficient quantity to reach the optimum final concentrations detailed in Table 3 below.

TABLE 3

Primers and optimum concentrations for the PCR technique

| Name of the gene | Primers | SEQ ID | Size of amplicon (bp) | Optimum concentration (nm) |
| --- | --- | --- | --- | --- |
| PR-1 | PR1-di | 32 | 167 | 200 |
| | PR1-re | 33 | | |
| PR-2 | PR2-di | 34 | 152 | 400 |
| | PR2-re | 35 | | |
| PR-4 | PR4-di | 36 | 123 | 200 |
| | PR4-re | 37 | | |
| PR-5 | PR5-di | 38 | 100 | 600 |
| | PR5-re | 39 | | |
| PR-8 | PR5-di | 40 | 173 | 200 |
| | PR5-re | 41 | | |
| PR-14 | PR14-di | 42 | 192 | 200 |
| | PR14-re | 43 | | |
| PR-15 | PR15-di | 44 | 132 | 200 |
| | PR15-re | 45 | | |
| PAL | PAL-di | 46 | 133 | 200 |
| | PAL-re | 47 | | |
| CHS | CHS-di | 48 | 234 | 100 |
| | CHS-re | 49 | | |
| DFR | DFR-di | 50 | 239 | 200 |
| | DFR-re | 51 | | |
| ANS | ANS-di | 52 | 298 | 200 |
| | ANS-re | 53 | | |
| PPO | PPO-di | 54 | 124 | 200 |
| | PPO-re | 55 | | |
| HMGR | HMGR-di | 56 | 206 | 400 |
| | HMGR-re | 57 | | |
| FPPS | FPPS-di | 58 | 255 | 200 |
| | FPPS-re | 59 | | |
| Far | Far-di | 60 | 161 | 200 |
| | Far-re | 61 | | |
| CSL | CSL-di | 62 | 134 | 200 |
| | CSL-re | 63 | | |
| APOX | APX-di | 64 | 185 | 200 |
| | APX-re | 65 | | |
| GST | GST-di | 66 | 185 | 200 |
| | GST-re | 67 | | |
| POX | POX-di | 68 | 197 | 100 |
| | POX-re | 69 | | |
| CalS | CalS-di | 70 | 176 | 200 |
| | CalS-re | 71 | | |
| Pect | Pect-di | 72 | 173 | 300 |
| | Pect-re | 73 | | |
| CAD | CAD-di | 74 | 85 | 200 |
| | CAD-re | 75 | | |
| EDS1 | EDS1-di | 76 | 269 | 200 |
| | EDS1-re | 77 | | |
| WRKY | WRKY-di | 78 | 171 | 200 |
| | WRKY-re | 79 | | |
| LOX2 | LOX2-di | 80 | 199 | 100 |
| | LOX2-re | 81 | | |
| JAR | JAR-di | 82 | 118 | 200 |
| | JAR-re | 83 | | |
| ACCO | ACCO-di | 84 | 193 | 200 |
| | ACCO-re | 85 | | |
| EIN3 | EIN3-di | 86 | 212 | 400 |
| | EIN3-re | 87 | | |
| TuA | TuA-di | 88 | 118 | 300 |
| | TuA-re | 89 | | |
| Actin | Actin-di | 90 | 140 | 100 |
| | Actin-re | 91 | | |
| GAPDH | GAPDH-di | 92 | 103 | 300 |
| | GAPDH-re | 93 | | |

Test 1—Relative Expression of the Defense Genes in Apple Tree Leaves Subjected to Various Treatments Protocol:

The expression of 28 target genes was monitored (i) in apple tree seedling leaves (obtained by open pollination of the Golden Delicious variety, see Brisset et al., Eur. J. Plant Pathol. 106, 529-536, 2000) subjected to NDS treatments and to various abiotic stresses, as well as (ii) in leaves of grafted maiden trees of two genotypes of apple, Evereste and MM106

(see Venisse et al., Molecular Plant-Microbe Interactions 15, 1204-1212, 2002, after infection by *Erwinia amylovora*, a fire blight agent.

The protocol implemented includes the following steps 1 to 7:

1) Treatment of the plants by spraying, sprinkling or infiltration of the product (or osmosis-purified water for the negative controls).

The various treatments were applied in the following way:
Baba (a.i. 95% DL-β-amino-n-butyric acid, Sigma ref. A-2004) applied by sprinkling a 10-mM solution (5 ml per 150-ml pot),
Bion® (a.i. 50% acibenzolar-S-methyl, Sygenta) applied by spraying until run-off of a 0.4 g/l solution,
Rhodofix® (a.i. 1% α-naphthylacetic acid, Nufarm SAS) applied by spraying until run-off of a 1.5 g/l solution,
Régalis® (a.i. 10% prohexadione-calcium, BASF Agro, BASF Agro) applied by spraying until run-off of a 2.5 g/l solution,
PRM® 12 RP (a.i. 11.3% ethephon, Bayer CropScience) applied by spraying until run-off of a 3 ml/l solution,
MeJA (a.i. 95% methyl jasmonate, Aldrich ref. 39,270-7) applied by sprinkling a 10-mM solution (5 ml per 150-ml pot),
Dehydration carried out by stopping the sprinkling,
PEG (a.i. polyethylene glycol 6000, Merck ref. 807491) applied by imbibition until the potting soil has been saturated (2 times 3 min) using a 36% solution,
Paraquat (a.i. paraquat dichloride x-hydrate PESTANAL®, Fluka ref. 36541) applied by spraying a 100-µM solution until run-off,
$H_2O_2$ (a.i. 30% hydrogen peroxide) applied by spraying a 10 ml/l solution,
*E. amylovora* applied by infiltration of a suspension of the strain CFBP1430 adjusted to $10^7$ cfu/ml.

2) Optional spraying of hydrogen peroxide 24 hours after step 1), in order to mimic the attack of a pathogen (which enables the direct stimulators and potentiators to be differentiated).

3) Tissue sampling at 24 hours, 48 hours and 72 hours after treatment.

4) Immediate freezing of the tissues in liquid nitrogen and preservation at −80° C.

5) Extraction of RNA, reverse transcription, verification of the absence of genomic DNA according to Venisse et al. (Molecular Plant-Microbe Interactions 15, 1204-1212, 2002).

6) Amplification via quantitative PCR for each extract, by preparing the following mix: 5 µg of cDNA, X µl of qPCR mix according to the supplier's instructions, and q.s.f. 2,500 µl ultrapure water, by distributing it in the amount of 25 µl per well of the ready-to-use 96-well plate, and by carrying out the amplification according to a 40-cycle qPCR program.

7) Processing of the results according to the ΔΔCt method, which provides the relative expressions of the defense genes in a given sample relative to an untreated sample called a "calibrator", said expressions being normalized by the geometric mean of the reference genes of these samples (Vandesompele et al., Genome Biol. 3(7); research 0034.1-0034.11, 2002; Livak and Schmittgen, Methods 25:402-408, 2001).

The expression results of the 28 target genes are detailed in Tables 4, 5 and 6 below, and consist of a matrix of the relative expressions in relation to "water" controls (sampled at the same time), which are transformed into log base 2 (J=day, h=hour).

These results are distributed over three tables, solely for the sake of presentation.

Results:
a) The Bion, Rhodofix and Régalis products show a rather similar activation of the following gene combination: PR-1, PR-2, PR-4, PR-5, PR-8, PR-14, HMGR, Far, CSL, POX, Pect, EDS1 and WRKY, with relative overexpression values (relative to water), which frequently are well above 3 (or $\log_2$(relative expression)>1.58, Tables 4 to 6).

These three products further ensure a significant and reproducible protection against fire blight.

It is interesting to note that, among these 3 products, only Bion (an analogue of salicylic acid) is approved as an NDS (on species other than the apple).

The inventors have already shown the protection effectiveness thereof against fire blight, but likewise against scab and mealy apple aphid, a protection correlated with the accumulation of some defense proteins (Brisset et al., 2000 and 2005).

Rhodofix (an analogue of auxin) is a thinner used in apple orchards in order to lighten the fruit load. According to the present tests, this product might likewise have defense-stimulating effects that have never been described.

As for Régalis (inhibitor of gibberillins via inhibition of dioxygenases), it is likewise used in apple orchards as a shoot growth reducer. The inventors have already demonstrated the protective capacity thereof with regard to fire blight, which could be linked to growth reduction (Brisset et al., 2005). The gene expression analyses show that it likewise has the ability to induce defenses, in particular those of the PR protein type, which, once again, has never been described.

b) The two products MeJA and Prm 12 show a rather similar activation of a combination of defense genes: PR-14, PAL, CHS, DFR, CSL, Pect, ACCO and EIN3, with relative overexpression levels in relation to water, which are often greater than 3 (or $\log_2$(relative expression)>1.58, Tables 4 to 6).

As concerns protection, these two products show a highly variable effectiveness, according to the tests, but, under the best circumstances, never reach the effectiveness of the Bion, Rhodofix and Régalis products.

It should be noted that PRM 12 (analogue of ethylene) is likewise a thinner used in apple orchards. In light of the present results, Rhodofix should be preferred over PRM 12, for the dual function thereof as a thinner and defense stimulator.

c) The Baba applied under our experimental conditions (sprinkling) shows little effect on the modulations of genes and no protective effect against fire blight.

Therefore, it represents a negative control in our experiments. It likewise validates the use of $H_2O_2$ in the operating procedure. As a matter of fact, Baba is known as a potentiator and not a direct stimulator, the action thereof on the defenses only being revealed after pathogen-induced stress.

In our operating procedure, the action of the latter is simulated by applying $H_2O_2$. The results indeed show that this additional treatment triggers the expression of some genes (POX, Pect, for example), which are not activated by the Baba treatment alone.

On the other hand, this phenomenon is not clearly observed for the other stimulators, which therefore rather appear to be direct stimulators.

d) Seen as a whole, the results obtained with the 6 NDS-type products appear to indicate that the overexpression of the genes PR-1, PR-2, PR-4, PR-5, PR-8, PR-14, HMGR, Far, CSL, POX, Pect, EDS1 and WRKY (advantageously with relative expression levels of greater than 3 relative to water) enable significant protection against fire blight under controlled conditions.

On the other hand, the overexpression of the genes PR-14, PAL, CHS, DFR, CSL, Pect, ACCO and EIN3 (with relative expression levels in relation to water, which are advantageously greater than 3) does not enable this protection to be ensured.

e) The abiotic stresses were applied with a view to answering two questions: i) is it possible to have artefacts on the expression of defense genes if the NDS-type product experiments occur under more constraining environmental conditions for plants (i.e., to observe activation of the genes due to stressful conditions and not to the NDSs), and ii) do stressful environmental conditions prevent the plants from reaction with the NDSs (which would then have an impact on the success of the orchard treatments).

The current results provide a partial answer to the first question. The water stresses (dehydration), osmotic and slightly oxidizing stresses (PEG) ($H_2O_2$—likewise serving as a control for the potentiation tests) only slightly modulate the target gene expressions. Only a strong oxidizing stress (paraquat=herbicide causing the production of a superoxide ion) strongly activates some genes, however, overall, the activations are weaker than those obtained when using Bion, for example.

f) The responses of the genes to an infection with *E. amylovora* show that this bacteria as a whole modulates the same target genes as the Bion, Rhodofix or Régalis treatments, but often with a lower amplitude, in particular for the PR protein genes.

Since bacteria greatly suppresses the genes of the jasmonic acid and phenylpropanoid pathways, it might have been expected that products causing the opposite effect, of the MeJA or PRM 12 type, might be effective from a protection standpoint, which is not the case under our experimental conditions.

On the contrary, the overall results show that the products that ensure significant protection activate the same combination of genes as the bacteria itself (genes PR-1, PR-2, PR-4, PR-5, PR-8, PR-14, HMGR, Far, CSL, POX, Pect, EDS1 and WRKY).

TABLE 4

Relative expression of the defense genes in apple tree leaves subjected to various treatments (Potential NDSs, abiotic stresses, infection with *E. amylovora*)

| A Traitements | | B Délaide préièvement | PR-1 | PR-2 | PR-4 | PR-5 | PR-8 | PR-14 | PR-15 | PAL | ANS |
|---|---|---|---|---|---|---|---|---|---|---|---|
| Baba | −$H_2O_2$ | J2 | 1.85 | 3.04 | 3.00 | 2.75 | 0.02 | −0.29 | 1.84 | 0.42 | 1.28 |
| | | J2 | −0.70 | 0.24 | −0.71 | 0.92 | 0.10 | −2.34 | −0.53 | 0.27 | 1.53 |
| | | J3 | 0.01 | 0.20 | −2.45 | −0.26 | −0.37 | −3.35 | 0.04 | 0.20 | −1.09 |
| | | J3 | 2.08 | −1.69 | −0.57 | 0.86 | −0.52 | 3.90 | 1.82 | 0.29 | −0.10 |
| | +$H_2O_2$ | J2 | 5.93 | 8.90 | 6.58 | 2.84 | 3.33 | 6.56 | 0.84 | 0.29 | 1.41 |
| | | J2 | 0.08 | −0.98 | 0.16 | −0.40 | 0.39 | −2.63 | 0.71 | 0.55 | 2.12 |
| | | J3 | 2.71 | 4.26 | −2.18 | 1.91 | 1.39 | −0.53 | 1.46 | −0.84 | 0.19 |
| | | J3 | 1.77 | −2.32 | −0.88 | 1.34 | −1.00 | 1.17 | 2.06 | −0.12 | 1.25 |
| Bion | −$H_2O_2$ | J2 | 8.37 | 6.89 | 8.61 | 5.77 | 6.07 | 3.31 | 1.88 | −0.14 | 1.51 |
| | | J2 | 3.20 | 9.64 | 7.17 | 1.02 | 3.50 | 3.75 | 1.61 | 1.11 | 0.21 |
| | | J3 | 5.99 | 7.99 | 5.43 | 4.46 | 2.23 | 4.09 | −1.98 | −1.29 | −1.56 |
| | | J3 | 2.14 | 1.61 | 8.07 | 3.88 | 1.62 | 0.49 | 4.96 | −0.15 | 0.14 |
| | +$H_2O_2$ | J2 | 8.53 | 11.96 | 10.25 | 6.52 | 5.57 | 2.22 | 4.09 | −0.25 | −0.15 |
| | | J2 | 3.87 | 6.36 | 5.10 | 2.43 | 3.25 | 2.95 | 1.72 | 1.91 | 1.50 |
| | | J3 | 7.66 | 13.12 | 6.37 | 4.11 | 2.74 | 5.01 | 1.33 | −2.25 | −4.05 |
| | | J3 | 5.35 | 7.07 | 8.03 | 5.68 | 3.62 | 4.52 | 3.60 | 0.83 | 0.14 |
| Rhodofix | −$H_2O_2$ | J2 | 2.61 | 9.34 | 6.87 | 1.75 | 3.16 | 5.43 | 0.98 | 1.78 | 2.40 |
| | | J3 | 5.99 | 7.56 | 9.06 | 3.15 | 3.56 | 6.59 | 2.93 | 0.32 | 0.77 |
| | +$H_2O_2$ | J2 | 3.87 | 6.85 | 7.42 | 2.72 | 3.19 | 4.49 | 4.83 | 1.15 | 1.49 |
| | | J3 | 6.47 | 6.19 | 8.82 | 3.13 | 3.74 | 4.29 | 3.15 | 0.14 | 1.29 |
| Régalis | −$H_2O_2$ | J2 | 4.76 | 3.80 | 3.25 | 2.42 | 4.07 | 7.55 | 2.77 | 0.22 | 1.31 |
| | | J2 | 2.08 | 5.91 | 3.45 | −0.84 | 2.29 | 3.31 | 1.12 | 1.36 | 0.77 |
| | | J3 | 3.62 | 4.38 | 3.09 | 0.96 | 1.36 | 0.79 | −0.08 | 0.64 | −0.05 |
| | | J3 | 4.11 | 3.84 | 3.80 | 1.22 | 1.91 | 6.20 | 1.37 | 0.58 | 2.70 |
| | +$H_2O_2$ | J2 | 4.02 | 11.09 | 8.82 | 4.24 | 4.07 | 5.07 | 0.63 | 0.81 | 2.37 |
| | | J2 | 1.85 | 1.57 | 6.39 | −1.92 | 2.72 | 4.80 | 6.12 | 2.69 | 1.92 |
| | | J3 | 4.00 | 8.88 | 2.56 | 1.46 | 1.00 | 4.66 | 3.73 | −0.51 | −1.58 |
| | | J3 | 1.99 | 0.07 | 2.72 | 1.66 | −0.39 | 2.50 | 0.54 | 0.12 | 0.06 |
| PRM12 | −$H_2O_2$ | J2 | 0.34 | 2.00 | 0.96 | 0.61 | 0.37 | 0.16 | 0.30 | 0.41 | 0.19 |
| | | J3 | 1.13 | −1.11 | 5.13 | −0.73 | 2.56 | 5.92 | 5.40 | 4.10 | 4.49 |
| | +$H_2O_2$ | J2 | 2.41 | 1.94 | 0.14 | −0.17 | 0.91 | 1.90 | 2.46 | 1.38 | 3.45 |
| | | J3 | 1.89 | −2.70 | 0.21 | 1.64 | −0.30 | 5.05 | 3.13 | −0.33 | 2.86 |
| MeJA | −$H_2O_2$ | J2 | 1.56 | 4.03 | 2.68 | −0.59 | 1.85 | 3.45 | −0.19 | 3.17 | 2.31 |
| | | J3 | 2.35 | 3.69 | 2.63 | 1.49 | 1.00 | 5.09 | 1.21 | 1.66 | 1.58 |
| | +$H_2O_2$ | J2 | 0.40 | 3.89 | 1.25 | −2.09 | 1.41 | −0.64 | 3.20 | 3.36 | 3.29 |
| | | J3 | 2.84 | 0.68 | 2.84 | −1.22 | 1.51 | 3.68 | 2.77 | 2.01 | 1.44 |
| C Deshydratation | | J2 | −2.01 | −1.80 | −4.15 | 0.57 | 0.39 | −2.11 | 1.82 | −2.26 | 0.60 |
| | | J4 | −0.91 | −1.65 | −4.21 | 0.00 | 0.00 | −0.56 | 0.00 | −0.12 | 0.00 |
| | | J7 | 1.12 | −1.28 | −4.36 | 1.20 | 0.70 | 2.71 | 3.01 | −1.54 | −1.25 |
| | | J10 | 0.47 | −1.06 | −3.33 | 2.49 | 2.15 | 3.09 | 2.66 | −2.12 | −1.24 |
| PEG | | J1 | 2.56 | 4.72 | 3.01 | 0.00 | 0.00 | 1.46 | 0.00 | 0.41 | 0.00 |
| | | J2 | 4.07 | 0.29 | 1.00 | −3.97 | −1.15 | 6.49 | −0.87 | 0.20 | 1.02 |
| | | J2 | −2.07 | −2.05 | −5.05 | 1.44 | 0.15 | 3.82 | 1.10 | −4.43 | −1.85 |
| | | J3 | 1.07 | 0.69 | 3.92 | −11.1 | 1.75 | 5.87 | −6.54 | 0.68 | 3.82 |
| | | J4 | 1.32 | −1.24 | 1.64 | −0.20 | 1.60 | 5.33 | 1.83 | −0.64 | 0.02 |
| | | J7 | 0.92 | −2.37 | 0.03 | −1.07 | 1.52 | 8.06 | 1.51 | −2.10 | 0.21 |
| | | J10 | 0.16 | −1.62 | 2.30 | −1.38 | 1.63 | 5.71 | 1.61 | −2.72 | −1.37 |

TABLE 4-continued

Relative expression of the defense genes in apple tree leaves subjected to various treatments (Potential NDSs, abiotic stresses, infection with *E. amylovora*)

| A Traitements | B Délaide préièvement | PR-1 | PR-2 | PR-4 | PR-5 | PR-8 | PR-14 | PR-15 | PAL | ANS |
|---|---|---|---|---|---|---|---|---|---|---|
| Paraquat | J1 | 0.55 | 4.09 | 7.10 | 0.00 | 0.00 | 2.61 | 0.00 | 1.99 | 0.00 |
| | J2 | 3.00 | 5.88 | 6.93 | −3.05 | 5.12 | 6.04 | 4.77 | 2.56 | −2.09 |
| | J3 | 0.54 | 2.53 | 6.63 | −8.56 | 5.36 | 1.28 | −0.34 | 0.66 | −0.78 |
| H₂O₂ | J2 | 2.44 | 4.75 | 2.53 | 3.02 | 0.83 | −1.92 | −0.20 | 1.91 | −0.58 |
| | J2 | −2.09 | 3.92 | 4.27 | −0.64 | 0.79 | −1.17 | 1.35 | 0.91 | 0.82 |
| | J3 | 0.66 | 2.36 | −2.25 | 0.41 | 0.38 | 0.70 | −0.82 | −0.87 | −2.02 |
| | J3 | 4.31 | 3.38 | 6.36 | 4.37 | 2.00 | 3.18 | 1.32 | −0.06 | 0.17 |
| *E. amylovora* | 6 h | 4.82 | 7.68 | 6.71 | 1.45 | 5.90 | 4.20 | 6.54 | 1.49 | −2.33 |
| | 6 h | 1.56 | 1.28 | 4.30 | 5.49 | 6.86 | 3.90 | 4.82 | 0.87 | 0.61 |
| | 24 h | 5.24 | 3.14 | 5.19 | 1.98 | 5.04 | 3.90 | 9.64 | 0.44 | −0.82 |
| | 24 h | 4.18 | −0.65 | 2.91 | −0.65 | 3.82 | 2.00 | 9.00 | −0.63 | −2.17 |

Key to Table 4
A) Treatments
B) Sampling time
C) Dehydration
[Translator's Note: Convert all commas to decimal points as concerns numerical entries.]

TABLE 5

Relative expression of the defense genes in apple tree leaves subjected to various treatments (potential NDSs, abiotic stresses, infection by *E. amylovora*)

| A Traitements | | B Délaide préièvement | CHS | DFR | PPO | HMGR | FPPS | Far | CSL | APOX | GST |
|---|---|---|---|---|---|---|---|---|---|---|---|
| Baba | −H₂O₂ | J2 | 0.27 | 0.64 | −0.06 | 1.22 | −0.02 | 0.85 | −0.37 | 0.02 | −0.05 |
| | | J2 | 0.29 | 0.93 | −1.07 | −0.67 | −0.41 | −0.28 | 0.38 | 2.14 | −0.34 |
| | | J3 | 0.19 | −0.02 | 0.54 | 1.95 | 0.46 | 0.81 | 0.55 | −1.18 | 0.51 |
| | | J3 | 0.31 | 0.72 | 1.24 | −0.52 | 0.56 | −1.03 | 1.34 | 0.11 | −0.14 |
| | +H₂O₂ | J2 | −0.50 | −0.28 | −2.03 | 2.50 | 0.60 | 1.91 | 1.50 | 1.49 | 0.14 |
| | | J2 | 1.18 | 1.17 | −1.09 | −1.67 | −0.79 | −1.50 | 0.36 | 1.76 | −0.71 |
| | | J3 | −0.47 | 0.42 | −0.67 | 1.98 | 1.46 | 1.25 | −0.34 | 1.20 | 0.88 |
| | | J3 | 0.12 | 0.73 | 1.87 | −0.09 | −0.08 | −0.31 | 0.56 | 2.41 | 0.27 |
| Bion | −H₂O₂ | J2 | −0.36 | −0.09 | 1.78 | 3.27 | −1.44 | 4.65 | 4.37 | 1.49 | 0.64 |
| | | J2 | 1.50 | 2.12 | 5.84 | 2.30 | 1.01 | 2.22 | 4.44 | 0.11 | 1.81 |
| | | J3 | −1.36 | −0.49 | 1.65 | 4.30 | 1.59 | 3.82 | 4.71 | −0.34 | 1.24 |
| | | J3 | −0.95 | −0.13 | 4.27 | 1.21 | 0.74 | 2.13 | 4.05 | 1.09 | 0.36 |
| | +H₂O₂ | J2 | −0.87 | −1.18 | −0.39 | 5.25 | 1.78 | 4.75 | 5.08 | 1.98 | 0.93 |
| | | J2 | 1.57 | 1.44 | 2.22 | 1.04 | 0.26 | 3.69 | 2.97 | −0.06 | 0.68 |
| | | J3 | −1.81 | 0.16 | 2.35 | 6.40 | 2.38 | 3.03 | 6.33 | −0.37 | 2.08 |
| | | J3 | 0.03 | 1.38 | 3.84 | 2.82 | 1.75 | 2.30 | 3.97 | 2.74 | 1.14 |
| Rhodofix | −H₂O₂ | J2 | 1.79 | 2.28 | 1.63 | 0.93 | −0.45 | 1.98 | 2.99 | −1.09 | 1.76 |
| | | J3 | 0.60 | 1.89 | 3.86 | 1.57 | 0.54 | 2.53 | 4.13 | −1.04 | 1.59 |
| | +H₂O₂ | J2 | 1.71 | 1.74 | 1.84 | 0.13 | −0.21 | 1.64 | 2.93 | 0.34 | 1.58 |
| | | J3 | 0.50 | 1.68 | 3.01 | 1.52 | 0.55 | 1.71 | 4.55 | −0.20 | 1.18 |
| Régalis | −H₂O₂ | J2 | 0.16 | 0.63 | −0.16 | 1.72 | 0.11 | 2.12 | 0.35 | 1.25 | 1.09 |
| | | J2 | 1.83 | 2.13 | 0.41 | −0.04 | −0.22 | 0.76 | 1.87 | 0.39 | 1.56 |
| | | J3 | 0.22 | 0.67 | 0.57 | 2.90 | 1.42 | 1.79 | 1.90 | −0.73 | 2.28 |
| | | J3 | 0.83 | 2.32 | 1.15 | 0.31 | 0.14 | −0.20 | 2.15 | −1.34 | 1.52 |
| | +H₂O₂ | J2 | 0.14 | 0.67 | −1.85 | 3.50 | 1.10 | 2.43 | 1.63 | 1.63 | 1.48 |
| | | J2 | 2.88 | 3.35 | 4.53 | −0.92 | −0.22 | 0.59 | 3.11 | 0.79 | 2.14 |
| | | J3 | 0.85 | 2.57 | −0.43 | 3.49 | 2.97 | 2.62 | 2.12 | −0.69 | 1.77 |
| | | J3 | 0.18 | 0.51 | 1.47 | −0.29 | 0.09 | −0.42 | 1.18 | −3.31 | −0.46 |
| PRM12 | −H₂O₂ | J2 | 0.08 | 0.23 | 1.59 | 0.23 | −0.46 | −3.18 | 0.59 | 0.53 | 0.48 |
| | | J3 | 3.78 | 4.60 | 5.67 | 1.41 | 0.62 | 0.57 | 4.12 | 1.15 | 1.88 |
| | +H₂O₂ | J2 | 1.96 | 1.98 | −0.58 | −1.17 | −1.18 | −1.85 | 1.90 | 1.01 | 0.44 |
| | | J3 | 0.23 | 1.10 | 0.63 | 0.09 | 0.30 | −1.62 | 1.42 | −1.91 | 0.68 |
| MeJA | −H₂O₂ | J2 | 2.97 | 2.92 | 1.28 | 1.49 | 0.00 | 2.34 | 2.29 | −3.00 | 1.00 |
| | | J3 | 1.22 | 1.55 | 0.78 | 1.16 | 0.13 | 1.51 | 1.81 | 0.95 | −0.15 |
| | +H₂O₂ | J2 | 3.73 | 3.43 | 0.80 | −0.38 | −0.07 | 0.74 | 2.26 | 1.87 | 0.47 |
| | | J3 | 1.47 | 1.36 | 1.23 | 0.60 | 0.43 | 0.39 | 1.46 | 2.11 | 0.87 |
| C Deshydratation | | J2 | 0.73 | 1.83 | −1.22 | 0.38 | −1.48 | 2.62 | −0.41 | −1.40 | −2.02 |
| | | J4 | 2.34 | 2.06 | −0.69 | 1.55 | −2.61 | 0.92 | −0.86 | 0.00 | −3.05 |
| | | J7 | 1.45 | 2.08 | −0.74 | 1.05 | −2.70 | 2.51 | −0.10 | 0.54 | −1.37 |
| | | J10 | 1.08 | 1.87 | −0.14 | 1.28 | −3.63 | 1.64 | 0.50 | 1.90 | −1.55 |
| PEG | | J1 | 0.93 | 0.87 | 0.37 | −1.18 | −0.12 | 3.26 | 1.24 | 0.00 | 0.20 |
| | | J2 | 0.05 | 1.12 | 0.35 | −0.87 | 0.29 | 0.96 | 1.18 | 2.38 | −0.01 |
| | | J2 | −0.67 | 0.78 | 1.76 | 1.66 | −2.51 | 1.06 | −0.15 | −1.37 | −0.73 |
| | | J3 | 0.64 | 2.42 | −1.57 | 0.20 | −0.79 | 1.45 | 2.23 | 1.31 | −0.39 |

TABLE 5-continued

Relative expression of the defense genes in apple tree leaves subjected to various treatments (potential NDSs, abiotic stresses, infection by E. amylovora)

| A Traitements | B Délaide préièvement | CHS | DFR | PPO | HMGR | FPPS | Far | CSL | APOX | GST |
|---|---|---|---|---|---|---|---|---|---|---|
| | J4 | 1.96 | 1.80 | 1.17 | 1.33 | −3.95 | −1.20 | 1.20 | −0.35 | −0.71 |
| | J7 | 1.74 | 1.83 | −2.02 | −0.07 | −4.15 | 0.18 | 0.75 | 0.68 | −0.79 |
| | J10 | 1.09 | 1.00 | 1.22 | 0.45 | −4.63 | 2.01 | 1.65 | 1.06 | 0.82 |
| Paraquat | J1 | −1.56 | −0.74 | 0.67 | 2.85 | 1.02 | 2.76 | 2.29 | 0.00 | 1.99 |
| | J2 | −1.49 | −1.14 | 6.27 | 1.20 | 0.15 | 2.30 | 4.42 | 2.01 | 1.83 |
| | J3 | −2.04 | −2.09 | 4.63 | −0.24 | −1.83 | 1.85 | 5.43 | 1.48 | 0.80 |
| H₂O₂ | J2 | 0.35 | 0.50 | −1.99 | 2.70 | 1.94 | 2.37 | 0.53 | 0.41 | 0.81 |
| | J2 | 1.33 | 0.80 | −0.71 | −0.07 | −1.18 | −0.97 | −0.02 | 0.38 | −0.02 |
| | J3 | −0.51 | −0.73 | −1.75 | 3.13 | 1.96 | 0.51 | −0.38 | −1.38 | 0.33 |
| | J3 | −0.09 | 0.57 | 1.24 | 1.37 | 0.85 | 2.02 | 1.64 | 0.77 | 0.40 |
| E. amylovora | 6 h | −2.67 | −1.16 | 6.27 | 4.71 | 5.12 | 6.13 | 4.94 | −2.33 | 4.10 |
| | 6 h | −4.28 | 4.32 | 6.18 | 2.88 | 2.64 | 4.46 | 3.90 | 0.61 | 2.53 |
| | 24 h | 1.32 | −0.16 | 7.60 | 3.71 | 2.52 | 3.58 | 5.20 | −0.82 | 3.24 |
| | 24 h | −2.85 | −1.79 | 8.04 | 2.68 | 1.78 | 5.68 | 3.70 | 2.17 | 3.43 |

Key to Table 5
A) Treatments
B) Sampling time
C) Dehydration
[Translator's Note: Convert all commas to decimal points as concerns numerical entries.]

TABLE 6

Relative expression of the defense genes in apple tree leaves subjected to various treatments (potential NDSs, abiotic stresses, infection by E. amylovora)

| A Traitements | | B Délaide préièvement | POX | CAD | CalS | Pect | EDS1 | WRKY | LOX2 | JAR | ACCO | EIN3 |
|---|---|---|---|---|---|---|---|---|---|---|---|---|
| Baba | −H₂O₂ | J2 | 0.44 | −0.45 | 0.19 | −0.04 | 0.41 | −1.51 | 0.37 | −0.80 | 0.10 | −0.09 |
| | | J2 | 1.57 | 0.26 | 0.66 | −1.38 | 0.08 | −0.34 | −0.61 | 0.56 | −0.26 | 3.15 |
| | | J3 | −1.16 | 0.71 | 0.00 | −0.73 | 0.16 | −1.33 | −0.69 | −0.29 | 0.00 | −0.65 |
| | | J3 | 0.95 | −0.30 | 0.35 | 1.66 | −1.70 | 2.55 | 0.09 | 0.29 | 0.43 | 0.41 |
| | +H₂O₂ | J2 | 2.20 | −0.87 | 0.75 | 2.04 | 1.13 | 0.34 | 0.10 | −0.44 | 1.14 | 0.60 |
| | | J2 | 2.28 | −0.16 | 0.44 | −1.76 | −0.69 | −1.71 | −0.41 | −0.16 | 2.13 | 1.94 |
| | | J3 | 1.41 | −0.15 | 2.10 | 2.96 | 0.97 | 0.27 | −0.62 | 1.52 | 0.64 | 1.69 |
| | | J3 | 3.22 | −0.29 | 1.88 | 2.11 | −0.58 | −0.35 | 0.09 | 1.02 | 2.14 | 1.32 |
| Bion | −H₂O₂ | J2 | 3.76 | −0.36 | 1.31 | 2.63 | 3.21 | 1.67 | −0.75 | −1.13 | 1.28 | −0.64 |
| | | J2 | 2.77 | 0.56 | −0.27 | −0.32 | 3.65 | 4.54 | −1.00 | −1.32 | 2.24 | 2.03 |
| | | J3 | 3.56 | −0.30 | 0.49 | 1.61 | 3.26 | 2.22 | −1.18 | −0.57 | 1.36 | 0.05 |
| | | J3 | 4.65 | 0.34 | 0.89 | 0.99 | 2.50 | 4.79 | 0.00 | −0.62 | 0.69 | 0.22 |
| | +H₂O₂ | J2 | 4.75 | −1.34 | 0.97 | 2.35 | 3.50 | 2.08 | −1.78 | −1.39 | 1.60 | −0.09 |
| | | J2 | 1.76 | 0.28 | 0.06 | 0.50 | 2.74 | 3.47 | 0.31 | −0.32 | 3.40 | 2.22 |
| | | J3 | 1.72 | −1.08 | 0.94 | 1.89 | 4.09 | 1.77 | −1.71 | −1.46 | 1.78 | −0.70 |
| | | J3 | 5.67 | 0.31 | 1.27 | 3.73 | 4.15 | 7.33 | 0.16 | 0.87 | 3.01 | 1.67 |
| Rhodofix | −H₂O₂ | J2 | 3.68 | 0.09 | 0.44 | 1.68 | 2.49 | 0.38 | −0.39 | −1.04 | 0.98 | 2.03 |
| | | J3 | 6.80 | −0.10 | 0.51 | 2.97 | 3.04 | 4.50 | −0.09 | −1.54 | 2.42 | −0.13 |
| | +H₂O₂ | J2 | 4.84 | 0.15 | 0.90 | −0.18 | 2.16 | 2.19 | 0.19 | −0.60 | 2.68 | 1.42 |
| | | J3 | 5.52 | −0.26 | 1.11 | 2.66 | 1.12 | 4.09 | 0.40 | 0.20 | 4.22 | 0.89 |
| Régalis | −H₂O₂ | J2 | 2.92 | 0.63 | 0.39 | 3.00 | 2.14 | 1.84 | −0.59 | −0.14 | 0.93 | 1.52 |
| | | J2 | 2.94 | 0.63 | −0.46 | −0.30 | 1.43 | 0.52 | 0.15 | −0.10 | 1.81 | 1.56 |
| | | J3 | 1.50 | 0.82 | 0.19 | 1.63 | 3.43 | −0.99 | 0.20 | −0.66 | 0.66 | −0.44 |
| | | J3 | 5.21 | 0.78 | −0.07 | 2.72 | 1.49 | 1.08 | 0.25 | −0.38 | 1.52 | −0.17 |
| | +H₂O₂ | J2 | 4.60 | −0.54 | 0.17 | 3.65 | 1.40 | −0.35 | −1.07 | −1.78 | 1.27 | 0.68 |
| | | J2 | 2.65 | 0.68 | −0.72 | −1.86 | 0.76 | 2.12 | 0.44 | −0.64 | 2.81 | 0.91 |
| | | J3 | 2.10 | −0.31 | 0.58 | 0.44 | 2.50 | −0.96 | 0.10 | −0.27 | 0.85 | −1.09 |
| | | J3 | 1.28 | −0.04 | 0.51 | 1.12 | 0.01 | −0.02 | 0.89 | −3.59 | 3.40 | 0.66 |
| PRM12 | −H₂O₂ | J2 | 0.56 | 0.67 | 0.78 | 0.29 | 0.34 | −1.70 | −0.39 | −0.34 | 0.93 | 2.56 |
| | | J3 | 3.25 | 0.94 | 1.05 | −0.90 | −0.13 | 4.08 | 1.72 | 0.40 | 2.23 | 0.59 |
| | +H₂O₂ | J2 | 3.59 | −0.36 | 0.30 | 1.47 | −0.50 | −0.94 | −0.24 | −0.22 | 3.56 | 2.74 |
| | | J3 | 2.52 | 0.00 | 1.24 | 4.88 | −0.32 | 1.27 | 0.13 | 1.03 | 4.56 | 2.32 |
| MeJA | −H₂O₂ | J2 | 0.66 | 1.52 | 0.05 | 0.98 | 1.91 | 1.25 | 1.60 | 1.25 | 1.92 | 3.82 |
| | | J3 | 3.86 | 0.01 | 1.14 | 3.87 | 1.22 | 0.85 | 1.45 | 0.63 | 1.96 | 1.22 |
| | +H₂O₂ | J2 | 2.84 | 0.70 | 0.48 | −2.02 | −0.17 | −0.06 | 1.51 | 0.73 | 3.48 | 2.54 |
| | | J3 | 4.29 | 0.35 | 1.48 | 2.16 | 0.98 | 3.46 | 1.99 | 1.61 | 2.28 | 1.80 |
| C Deshydratation | | J2 | −0.03 | −0.89 | 0.23 | −1.95 | −0.07 | −1.80 | 1.19 | 0.30 | 0.32 | −1.87 |
| | | J4 | 0.00 | −0.87 | 0.00 | 0.00 | 0.44 | −2.58 | 1.07 | 0.00 | 0.71 | 0.00 |
| | | J7 | 1.54 | −0.48 | −0.53 | 2.56 | 0.13 | 0.63 | 1.85 | −0.46 | 0.03 | −1.23 |
| | | J10 | 2.44 | −0.43 | 0.12 | 4.46 | 0.23 | −0.39 | 2.06 | 0.04 | 1.74 | 0.91 |

TABLE 6-continued

Relative expression of the defense genes in apple tree leaves subjected to various treatments (potential NDSs, abiotic stresses, infection by E. amylovora)

| A<br>Traitements | B<br>Délaide<br>preièvement | POX | CAD | CalS | Pect | EDS1 | WRKY | LOX2 | JAR | ACCO | EIN3 |
|---|---|---|---|---|---|---|---|---|---|---|---|
| PEG | J1 | 0.00 | 0.59 | 0.00 | 0.00 | 0.24 | −1.23 | 1.51 | 0.00 | −1.96 | 0.00 |
| | J2 | −1.33 | 0.72 | 0.24 | 2.18 | 0.46 | 0.70 | 2.48 | 1.06 | 0.69 | 0.02 |
| | J2 | −1.07 | −0.52 | 0.38 | −1.23 | −0.92 | −0.10 | 2.19 | −0.46 | −0.56 | −1.82 |
| | J3 | −3.29 | −0.31 | −0.89 | −0.98 | 0.96 | 3.41 | 0.41 | −1.00 | 0.51 | −0.36 |
| | J4 | 0.81 | 0.86 | 0.43 | 2.37 | −1.62 | −1.24 | 1.36 | −1.43 | −0.33 | 0.63 |
| | J7 | 0.00 | 0.06 | 0.86 | 2.38 | −0.54 | −2.30 | 1.96 | −0.19 | −0.36 | −0.18 |
| | J10 | −2.50 | 0.58 | −0.08 | 0.56 | −2.40 | −1.11 | 1.00 | −1.66 | 1.16 | −0.07 |
| Paraquat | J1 | 0.00 | 0.04 | 0.00 | 0.00 | 0.83 | 4.01 | −0.58 | 0.00 | −1.33 | 0.00 |
| | J2 | 4.26 | 0.27 | 0.42 | 2.17 | 2.89 | 6.37 | −0.54 | −0.81 | 0.02 | 0.21 |
| | J3 | −0.53 | −0.51 | 0.01 | −2.82 | 2.28 | 2.76 | −2.37 | −2.46 | 0.41 | −0.11 |
| $H_2O_2$ | J2 | 1.07 | −1.64 | 1.67 | −0.44 | 1.42 | −0.04 | 0.18 | 1.09 | 0.89 | 1.44 |
| | J2 | 1.06 | 0.29 | 0.27 | −1.62 | −0.36 | −0.12 | −0.45 | −0.27 | 1.36 | 1.53 |
| | J3 | −0.26 | −0.72 | −0.10 | 0.71 | 0.19 | −2.26 | 0.16 | −0.56 | 0.30 | −0.26 |
| | J3 | 1.88 | −0.54 | 0.93 | 1.65 | 2.08 | 4.02 | 0.42 | 0.43 | 0.84 | 0.41 |
| E. amylovora | 6 h | 2.76 | 1.95 | 1.31 | −1.27 | 1.36 | 6.02 | −4.60 | −3.83 | 1.66 | 5.00 |
| | 6 h | 3.64 | 1.63 | 2.92 | −0.60 | 2.03 | 8.29 | −4.63 | −0.19 | 1.37 | 6.02 |
| | 24 h | −0.79 | 1.81 | 0.09 | −3.72 | 1.25 | 2.13 | −3.50 | −2.34 | 1.31 | 1.74 |
| | 24 h | 1.12 | 2.46 | −0.42 | −5.98 | 0.91 | 2.51 | −2.57 | −5.31 | 1.11 | 0.97 |

Key to Table 6
A) Treatments
B) Sampling time
C) Dehydration
[Translator's Note: Convert all commas to decimal points as concerns numerical entries.]

Test 2—Validation of the Relevance of the Genes Selected from 10 NDSs
Protocol:

The products tested are listed in Table 7. This involves 10 NDS candidates, as well as an antibiotic (Plantomycin).

TABLE 7

| Products tested | Active material | Concentration tested* | Comments |
|---|---|---|---|
| Aliette (BayerCropScience) | Fosetyl-A | 6 g/lq | Fungicide, NDS |
| Amid-Thin (Nufarm) | 1-Naphthaleneacetamide | 0.6 g/l | Analogue auxin thinner |
| Bion (Syngenta) | Acibenzolar-S-methyl | 0.4 g/l | SA NDS analogue |
| Iodus (Goëmar) | Lamanarin | 7.5 ml/l | NDS |
| Maxcel (Valent Biosciences) | 6-benzyl adenine | 7.5 ml/l | Cytokinin analogue thinner |
| PRM12 (BayerCropScience) | Ethephon | 3 ml/l | Ethylene precursor thinner |
| Régalis (BASF) | Prohexadione-Ca | 2.5 g/l | 2-oxoglutaric growth regulator analogue |
| Rhodofix (Nufarm) | α-Acetic acid napthyl | 1.5 g/l | Analogue auxin thinner |
| Stifenia (S.O.F.T.) | Extract of fenugreek seeds | 10 g/l | NDS |
| V-Plaask (Plaaskem) | SA derivatives + fertilizer | 10 ml/l | Fertilizer and NDS |
| Plantomycin | Streptomycin | 0.56 g/lq | Antibiotic |

*Concentration of formulated product

For Analyzing Defenses

The tests are conducted under semi-controlled greenhouse conditions (23° C. during the day/17° C. at night, natural lighting, complementary neon light), on apple tree seedlings (derived from seeds of the Golden Delicious variety), actively growing at the stage of 3 to 6 leaves.

At day 0, the plants are sprayed with the candidate products or water (negative control), until saturated, with a compressed-air sprayer.

Half of these plants are sprayed with hydrogen peroxide (200-fold dilution of a 30% solution) using a manual sprayer, on day 1 (day 0+1 day), in order to simulate an attack of Erwinia amylovora, a fire blight agent (this enables a defense-potentiating effect versus a direct stimulating effect to be localized for the products tested).

Samples of leaf disks (10 disks measuring 0.6 cm in diameter from 5 pooled/sampled leaves F1) are taken on Day 0 (untreated seeds-calibrator), then, on Day 1 (prior to the hydrogen peroxide treatment) and finally on Day 2 (Day 0+2) and Day 3 (Day 0+3), on the batches treated or not treated with hydrogen peroxide.

The leaf disks are immediately frozen in liquid nitrogen and preserved at 80° C. until extracting the RNAs. The latter are retrotranscribed into cDNA and the defense gene expression levels are monitored by qPCR (SYBR Green), using the tool according to the invention.

Three separate bioassays where carried out for all of the products.

The relative expression levels are calculated using the ΔΔCt method: this involves relative expressions in relation to the calibrator (J0), or in relation to the water controls at each sampling time, which are normalized by the geometric mean of the relative expressions of 3 reference genes (TuA, actin, GAPDH). These relative expressions are transformed into $\log_2$ in order to provide the same weight to the gene inductions and repressions.

For Analyzing the Protective Power

These same products were tested in the following way, for the protective power thereof against fire blight.

The tests were carried out on the same type of plant material and under greenhouse conditions identical to those above.

The products were sprayed using the same sprayer as above, 4 days or 4 hours prior to artificial inoculation with *E. amylovora* (3×10 parcels of seedlings per product and per treatment/inoculation period).

On the day of inoculation, the youngest developed leaf (F1) of each seedling (whether treated 4 days prior by the products, or ready to receive a so-called "4-hour" treatment, is wounded using a scalpel (2 parallel cuts to the lower ⅓ of the leaf, and perpendicular to the main vein).

The 4-hour treatments are then carried out.

Four hours after treatment, a bacterial suspension of the strain CFBP1430 of *E. amylovora*, which has been prepared in sterile water at $10^6$ cfu/mL, is spray-inoculated (by the pressure sprayer) over all of the plants treated 4 days or 4 hours beforehand and wounded 4 hours beforehand.

Grading the symptoms, i.e., the presence of a necrosis having developed on the stem from the wounded leaf, is carried out 3 weeks after inoculation. The percentage of plants infected is calculated in each parcel (10) of plants and related to the mean of the infection percentages obtained for the three control parcels, for the 3 "water" control parcels of the same test (relative infection). The distributions of the relative infection percentages obtained (within and outside of the experiments) are shown by Tukey box plots: the median is represented by the wide black line at the center of the box and the average by the square; the notches represent confidence intervals of the median (P=0.05).

At least two separate tests are carried out for all of the products.

Results:

Analysis of the Defenses

The averaged expression results for the 28 target genes are detailed in Tables 8 and 9 below; these results are distributed over several tables, for presentation purposes only.

The expression results for the genes derived from the tool according to the invention (Tables 8 and 9) reveal 4 products (Bion, Iodus, Régalis, Rhodofix) capable of activating defenses in a repeatable manner over the 3 separate biological repetitions.

The inductions relate to a rather close set of genes in the apple tree leaves, with, however, a few differences.

a) Bion is the product that activates most of the genes most intensely and very reproducibly (some genes are regularly expressed $2^{10}$ times more in the tissues treated with Bion than in the control tissues). The genes of the SA pathway are particularly induced, and this strong induction is correlated with a repression of the genes of the JA pathway, which is consistent with SA pathway/JA pathway antagonism described in literature.

b) Iodus, Régalis and Rhodofix significantly activate only a portion of the genes induced by Bion, or in a less constant manner. For example, PR1, PR5 or PPO are 3 genes that are highly activated by Bion, and little or not at all by said 3 products.

c) Régalis demonstrates a potentiating effect because the gene inductions are manifested above all after treatment with hydrogen peroxide (particularly visible for the PECT gene).

d) The other 3 products that claim an NDS action, namely Aliette, Stifena and V-Plaask, as well as the other 3 thinners, namely Amid Thin, Maxcel and Prm12, or else the biocide product Plantomycin, do not cause any reproducible and significant induction.

Protection Analysis

Among the 11 products tested, only three display effective protection against fire blight, when they are sprayed 4 days prior to inoculation (conditions for revealing a stimulating effect): this involves Bion, Régalis and Rhodofix, which significantly reduce the percentages of infection in the seedlings (FIG. 1A).

The products that do not induce any of the defense genes present on the tool, as well as Iodus, which is capable of inducing some defenses, are not effectively protective when applied 4 days prior to inoculation.

When sprayed a few hours prior to inoculation, Bion retains a very significant degree of effectiveness; Régalis is always effective, and likewise remains effective, although less significantly. (FIG. 1B).

These degrees of effectiveness, however, do not reach that obtained with Plantomycin, a biocide against *E. amylovora*.

No other product significantly and reproducibly reduces the percentages of infection of seedlings.

Conclusion

In light of these results, the tool according to the invention makes it possible to eliminate the majority of the candidate NDS products, which turn out to have no potential for protecting apple tree seedlings against fire blight, i.e., Aliette, Amid Thin, Maxcel, PRM12, Stifenia, V-Plaask.

Among the 4 products retained in the screening (Bion, Iodus, Régalis, Rhodofix), only Iodus ultimately shows no effective protection for seedlings against fire blight.

The tool according to the invention is therefore useful in selecting products having a protective potential (at the very least against fire blight), and which deserve to be retained for experimentation purposes.

TABLE 8

| A Traitement | B Délaide | PR1 | PR2 | PR4 | PR5 | PR8 | PR14 | PR15 | PAL | ANS | CHS | DFR | PPO | HMGR | FPPS |
|---|---|---|---|---|---|---|---|---|---|---|---|---|---|---|---|
| Aliette | J1 | −0.97 | 0.16 | 0.31 | 0.50 | −0.28 | 0.10 | 2.13 | 0.37 | −0.09 | −0.01 | −1.01 | 2.64 | 0.18 | −0.40 |
| | J2 | −2.12 | −2.17 | 0.92 | −2.16 | 0.87 | −0.20 | 0.46 | −0.25 | 0.21 | −0.03 | 0.22 | −1.07 | 0.63 | 0.12 |
| | J3 | −0.55 | 0.49 | 0.48 | 0.26 | −0.02 | −1.27 | −0.41 | −1.17 | −1.32 | −1.55 | −0.92 | 1.00 | 0.41 | −0.18 |
| | J2 + $H_2O_2$ | −0.68 | 1.05 | 3.91 | −0.94 | 3.17 | 0.81 | 0.00 | −0.95 | −0.75 | −0.70 | −0.43 | −0.09 | 0.54 | 0.00 |
| | J3 + $H_2O_2$ | 0.04 | 3.21 | 0.70 | 1.30 | 0.24 | −0.01 | 0.53 | −1.26 | −1.58 | −1.36 | −1.06 | 1.64 | 0.44 | −0.10 |
| Amid Thin | J1 | 0.81 | 0.80 | 0.86 | −0.57 | 0.39 | 1.50 | −0.39 | 0.09 | 0.23 | 0.23 | 0.45 | 1.05 | 0.52 | −0.39 |
| | J2 | −0.13 | −0.73 | 0.65 | −0.81 | 0.40 | −0.32 | 0.52 | 0.06 | 0.74 | 0.54 | 0.53 | −0.45 | −0.05 | 0.02 |
| | J3 | −0.58 | 0.44 | −0.37 | 0.21 | −0.15 | 0.33 | 0.04 | −0.23 | −0.05 | −0.56 | −0.23 | 0.95 | 0.50 | 0.59 |
| | J2 + $H_2O_2$ | 0.37 | 2.33 | 3.22 | −0.07 | 2.39 | 1.78 | 1.66 | −0.16 | −0.39 | −0.19 | −0.08 | 0.38 | −0.17 | 0.45 |
| | J3 + $H_2O_2$ | 0.16 | 2.30 | 1.21 | 0.49 | 1.06 | 1.04 | 0.01 | −1.17 | −1.52 | −1.73 | −0.64 | 0.10 | 0.42 | 0.43 |
| Bion | J1 | 1.74 | 6.30 | 5.80 | 3.73 | 2.51 | 1.06 | −0.62 | −0.17 | −1.79 | −1.64 | −1.51 | 1.19 | 2.18 | 0.93 |
| | J2 | 3.47 | 8.78 | 9.62 | 4.12 | 4.82 | 3.99 | −0.89 | 2.22 | 0.97 | 0.78 | 1.10 | 3.65 | 3.31 | 1.74 |
| | J3 | 6.18 | 11.20 | 9.96 | 4.70 | 5.29 | 7.61 | 4.24 | 1.11 | 0.09 | 0.26 | 0.30 | 5.55 | 1.64 | 1.02 |

TABLE 8-continued

| A Traitement | B Délaide | PR1 | PR2 | PR4 | PR5 | PR8 | PR14 | PR15 | PAL | ANS | CHS | DFR | PPO | HMGR | FPPS |
|---|---|---|---|---|---|---|---|---|---|---|---|---|---|---|---|
| | J2 + H$_2$O$_2$ | 3.58 | 9.23 | 9.75 | 4.07 | 5.72 | 4.19 | 1.06 | 2.06 | −0.17 | −0.16 | 0.04 | 4.74 | 3.84 | 1.42 |
| | J3 + H$_2$O$_2$ | 6.07 | 11.05 | 8.99 | 4.46 | 4.97 | 6.87 | 2.40 | 0.78 | 0.53 | 0.04 | 0.20 | 4.32 | 2.23 | 0.75 |
| Iodus | J1 | 1.67 | 6.04 | 6.91 | 1.24 | 3.37 | 4.09 | 1.90 | 0.50 | −1.37 | −1.03 | −0.62 | 2.55 | 2.20 | 1.55 |
| | J2 | 4.53 | 4.74 | 6.88 | 3.15 | 5.46 | 6.92 | 1.75 | 1.13 | 1.04 | 0.14 | 1.61 | 1.81 | 2.76 | −0.02 |
| | J3 | 3.30 | 3.22 | 4.64 | 1.56 | 2.43 | 1.26 | 0.08 | −2.39 | 0.07 | −0.42 | −0.03 | 2.48 | 0.48 | −0.25 |
| | J2 + H$_2$O$_2$ | 3.93 | 4.28 | 6.98 | 3.35 | 5.28 | 6.86 | 1.51 | 0.11 | 0.86 | −0.63 | 1.10 | 0.89 | 2.71 | 0.05 |
| | J3 + H$_2$O$_2$ | 3.54 | 3.31 | 4.74 | 2.02 | 2.65 | 1.76 | 0.44 | 0.69 | 0.53 | −0.20 | 0.54 | 2.39 | 0.75 | −0.19 |
| Maxcel | J1 | 0.45 | −0.87 | 0.99 | −0.20 | 0.10 | 0.77 | −0.01 | −0.01 | 0.20 | −0.17 | 0.59 | 0.26 | 0.11 | −0.59 |
| | J2 | −0.20 | −1.11 | 0.18 | −0.21 | 0.34 | 1.03 | 0.26 | −0.31 | 0.65 | 0.07 | 0.55 | −1.06 | 0.17 | −0.06 |
| | J3 | 0.75 | −0.27 | −0.01 | 0.08 | −0.71 | −2.12 | 1.00 | −0.47 | −1.14 | −0.75 | −0.21 | 0.61 | 0.04 | 0.43 |
| | J2 + H$_2$O$_2$ | 0.77 | 1.23 | 2.92 | −0.46 | 2.81 | 0.88 | 0.32 | −0.29 | 0.44 | −0.50 | 0.59 | −1.08 | 0.05 | −0.03 |
| | J3 + H$_2$O$_2$ | 0.64 | 2.02 | 0.30 | 0.89 | 1.15 | −0.49 | −0.14 | −0.42 | −0.85 | −0.77 | −0.10 | 0.09 | 0.67 | 0.47 |
| PRM12 | J1 | −0.79 | 0.01 | 2.58 | −0.61 | 0.92 | 1.82 | −0.97 | 1.06 | 0.92 | 0.37 | 1.13 | 0.62 | 0.98 | −0.70 |
| | J2 | 0.00 | −0.31 | 0.66 | −1.59 | 0.74 | −1.04 | −0.64 | −0.44 | 0.32 | −0.04 | 0.00 | −0.22 | 0.36 | −0.10 |
| | J3 | −0.49 | 0.10 | 0.11 | 0.20 | −0.76 | −1.25 | 1.16 | −0.60 | −0.91 | −0.80 | −0.52 | 1.15 | −0.09 | −0.09 |
| | J2 + H$_2$O$_2$ | 1.17 | 2.72 | 2.68 | −0.41 | 2.77 | 1.47 | 1.75 | −0.01 | 0.86 | 0.33 | 0.92 | 1.03 | 0.49 | 0.33 |
| | J3 + H$_2$O$_2$ | −0.35 | 2.21 | 0.64 | 0.49 | 0.68 | −1.21 | 0.17 | −1.18 | −1.36 | −1.48 | −0.70 | 0.15 | 0.19 | −0.14 |
| Regalis | J1 | −0.24 | 0.79 | 3.93 | −0.05 | 1.52 | 1.62 | 1.27 | 0.31 | 1.11 | 0.78 | 0.47 | 3.48 | 0.66 | 0.16 |
| | J2 | 0.28 | 2.27 | 4.29 | 1.65 | 2.45 | 1.75 | 1.43 | 0.01 | 1.77 | 0.82 | 1.02 | 0.32 | 0.20 | 0.41 |
| | J3 | 0.86 | 4.69 | 3.25 | 1.13 | 2.96 | 1.70 | −0.04 | 0.63 | 1.54 | 0.97 | 1.04 | 0.38 | 0.64 | 0.17 |
| | J2 + H$_2$O$_2$ | 1.19 | 5.46 | 7.22 | 2.55 | 4.21 | 4.20 | 2.33 | 0.69 | 1.43 | 0.84 | 1.23 | 2.70 | 1.44 | 0.47 |
| | J3 + H$_2$O$_2$ | 2.87 | 6.25 | 6.17 | 2.94 | 4.20 | 3.20 | 1.13 | 1.29 | 1.52 | 1.25 | 1.78 | 2.35 | 1.08 | 0.45 |
| Rhodofix | J1 | 1.46 | 4.99 | 6.65 | 0.83 | 3.69 | 6.53 | 0.88 | 0.39 | 0.00 | 0.15 | 0.64 | 2.77 | 1.89 | 0.76 |
| | J2 | 1.27 | 6.82 | 7.40 | 3.26 | 4.33 | 4.18 | −0.26 | 1.21 | 1.44 | 1.51 | 1.03 | 0.35 | 1.70 | 0.56 |
| | J3 | 0.34 | 4.00 | 2.56 | 1.51 | 0.57 | 0.42 | 0.68 | 0.09 | −0.17 | −0.11 | 0.05 | −0.12 | −0.23 | −0.08 |
| | J2 + H$_2$O$_2$ | 0.37 | 6.46 | 6.92 | 2.61 | 4.04 | 4.83 | −0.44 | −0.01 | −0.10 | 0.06 | 0.01 | 0.48 | 1.25 | 0.36 |
| | J3 + H$_2$O$_2$ | 2.19 | 4.95 | 4.82 | 2.02 | 2.71 | 1.34 | 0.06 | −0.01 | −0.24 | −0.45 | 0.82 | 0.45 | 1.45 | 0.62 |
| Stifenia | J1 | −0.80 | 0.14 | −0.99 | 0.46 | −0.54 | −0.75 | −1.84 | −1.12 | −1.13 | −1.00 | −1.59 | −0.82 | −0.40 | −0.25 |
| | J2 | 0.72 | 1.28 | 1.56 | 3.09 | 2.33 | 1.12 | 1.19 | 0.31 | 0.88 | 0.68 | 0.63 | −0.08 | 0.05 | 0.12 |
| | J3 | 0.61 | 0.24 | 0.47 | 0.11 | 1.11 | 1.84 | 1.19 | 0.39 | 0.30 | 0.64 | 1.14 | −0.50 | 0.57 | 1.29 |
| | J2 + H$_2$O$_2$ | 1.32 | 1.72 | 4.01 | 2.55 | 5.59 | 2.16 | 0.97 | 0.53 | 0.71 | 0.03 | 0.58 | 0.15 | 0.99 | −0.13 |
| | J3 + H$_2$O$_2$ | 1.31 | −0.02 | 0.00 | −0.07 | 1.19 | 0.11 | −0.26 | −0.70 | −0.13 | −0.39 | 0.23 | 0.81 | 0.58 | 0.22 |
| Plantomyc. | J1 | 1.23 | 1.05 | 1.51 | −0.19 | 0.21 | 0.35 | 0.43 | −0.48 | −1.42 | −0.99 | −1.04 | 1.91 | 0.02 | 0.01 |
| | J2 | −1.62 | −1.16 | −0.33 | −0.45 | 0.03 | 0.18 | −0.94 | −1.14 | −0.79 | −1.28 | −1.50 | −0.61 | 0.16 | −0.50 |
| | J3 | 1.39 | 2.59 | 1.35 | 1.12 | 0.27 | 0.14 | 1.93 | −0.17 | −1.00 | −0.25 | −0.96 | 1.13 | −0.27 | 0.07 |
| | J2 + H$_2$O$_2$ | 1.54 | 2.96 | 4.03 | 0.07 | 3.00 | 1.80 | 0.37 | −0.28 | −0.07 | 0.07 | 0.04 | 1.38 | 0.89 | 0.09 |
| | J3 + H$_2$O$_2$ | 2.03 | 3.31 | 2.19 | 0.60 | 1.14 | −0.06 | 0.58 | −0.88 | −0.63 | −0.44 | −0.68 | 1.75 | 0.30 | −0.34 |
| Vplaask | J1 | −0.66 | −0.20 | 0.25 | 1.60 | 0.17 | −0.05 | 0.83 | 0.24 | 0.52 | 0.35 | −0.20 | 0.88 | −1.60 | −0.43 |
| | J2 | 0.76 | −0.15 | −0.98 | 1.53 | 2.50 | 2.37 | 1.02 | −3.41 | −0.25 | −1.44 | −0.33 | −0.78 | 0.77 | −2.23 |
| | J3 | 0.40 | −0.45 | 0.38 | 0.57 | 0.16 | −1.44 | 0.23 | −0.20 | −0.61 | −1.29 | −0.78 | 0.35 | 0.28 | 0.13 |
| | J2 + H$_2$O$_2$ | 0.37 | 1.11 | 1.39 | 1.53 | 2.83 | 2.22 | 2.54 | −1.33 | 0.27 | −1.03 | 0.64 | 0.79 | 0.84 | 0.47 |
| | J3 + H$_2$O$_2$ | 1.43 | 0.48 | 0.24 | 1.25 | 0.30 | −1.88 | 1.05 | −0.79 | −1.39 | −1.61 | −1.00 | 1.26 | 0.34 | 0.57 |
| H$_2$O$_2$ | J2 + H$_2$O$_2$ | 0.85 | 3.69 | 3.89 | 0.91 | 2.12 | 1.32 | −0.26 | −0.56 | −0.63 | −0.80 | −0.65 | 1.20 | 1.05 | 0.06 |
| | J3 + H$_2$O$_2$ | 1.41 | 4.05 | 2.59 | 1.73 | 1.73 | 3.29 | 1.57 | −0.57 | −0.49 | −0.75 | −0.36 | 0.71 | 0.14 | 0.08 |

TABLE 9

| A Traitement | B Délaide | FAR | CSL | APOX | GST | POX | CAD | CalS | PECT | EDS1 | WRKY | LOX2 | JAR | ACCO | EIN3 |
|---|---|---|---|---|---|---|---|---|---|---|---|---|---|---|---|
| Aliette | J1 | −0.90 | −0.16 | −0.29 | −0.23 | 0.99 | 0.02 | −0.22 | −0.32 | 0.09 | −0.04 | 0.39 | −0.40 | −0.23 | −0.35 |
| | J2 | −1.62 | −0.21 | 0.09 | −0.06 | −0.91 | −0.12 | 0.06 | −0.89 | 0.44 | 1.18 | 0.23 | −0.25 | −0.08 | 0.07 |
| | J3 | 0.78 | −0.19 | −0.29 | 0.16 | −0.23 | −0.05 | −0.09 | −0.24 | −0.36 | −1.39 | 0.05 | −0.08 | −0.13 | 0.54 |
| | J2 + | −1.25 | 0.23 | 0.12 | 0.73 | 2.39 | 0.06 | 0.24 | 0.61 | 1.20 | 0.51 | 0.21 | −0.45 | 0.44 | 0.45 |

TABLE 9-continued

| A Traitement | B Délaide | FAR | CSL | APOX | GST | POX | CAD | CalS | PECT | EDS1 | WRKY | LOX2 | JAR | ACCO | EIN3 |
|---|---|---|---|---|---|---|---|---|---|---|---|---|---|---|---|
| | H$_2$O$_2$ | | | | | | | | | | | | | | |
| | J3 + H$_2$O$_2$ | 1.28 | 0.24 | 0.12 | 0.42 | 2.08 | 0.08 | 0.25 | 0.24 | −0.21 | −0.30 | 0.29 | 0.15 | −0.09 | 0.69 |
| Amid Thin | J1 | 0.06 | 0.17 | −0.40 | 0.51 | 0.91 | 0.31 | −0.14 | 1.21 | 0.18 | 0.02 | 0.45 | 0.11 | 0.57 | 0.71 |
| | J2 | −0.54 | 0.16 | −0.42 | 0.46 | 0.01 | 0.37 | 0.09 | 0.11 | 1.03 | −0.33 | 0.38 | −0.09 | 0.44 | 0.59 |
| | J3 | −0.30 | −0.14 | −0.14 | 0.54 | 0.37 | 0.05 | 0.18 | 0.37 | 0.32 | 0.38 | 0.19 | 0.13 | 0.36 | 0.13 |
| | J2 + H$_2$O$_2$ | 0.20 | 0.51 | 0.13 | 0.88 | 1.16 | 0.41 | 0.71 | 1.62 | 1.74 | 1.53 | −0.09 | 0.42 | 0.89 | 0.35 |
| | J3 + H$_2$O$_2$ | 0.96 | −0.39 | −0.47 | 0.44 | 0.77 | −0.15 | 0.33 | 0.03 | 0.27 | −0.45 | −0.40 | −0.28 | 0.04 | −0.27 |
| Bion | J1 | 4.20 | 1.74 | −0.06 | 2.35 | 1.66 | 0.51 | −0.04 | 0.17 | 3.21 | 2.30 | −0.67 | −1.10 | 0.89 | 0.52 |
| | J2 | 3.26 | 5.50 | 0.42 | 2.08 | 3.27 | 0.14 | −0.17 | 1.03 | 4.14 | 5.54 | −0.36 | −0.82 | 1.26 | 1.02 |
| | J3 | 2.54 | 7.15 | 0.62 | 1.86 | 3.47 | 0.38 | 0.49 | 2.26 | 4.09 | 4.99 | −1.25 | −0.84 | 1.11 | 0.30 |
| | J2 + H$_2$O$_2$ | 2.36 | 6.70 | 0.49 | 1.99 | 3.67 | 0.25 | −0.18 | 1.10 | 4.65 | 5.61 | −1.52 | −2.01 | 1.12 | 0.64 |
| | J3 + H$_2$O$_2$ | 2.02 | 6.54 | 0.60 | 1.46 | 4.19 | −0.02 | 0.16 | 2.07 | 4.22 | 5.04 | −1.34 | −1.06 | 0.98 | −0.06 |
| Iodus | J1 | 2.58 | 3.78 | 0.13 | 1.75 | 1.19 | −0.43 | −0.15 | 0.16 | 0.74 | 1.90 | −0.34 | −0.05 | 0.91 | 0.03 |
| | J2 | 2.45 | 4.08 | 0.36 | 2.07 | 0.94 | 0.65 | 0.50 | 4.70 | 3.14 | 2.68 | 0.68 | 0.49 | 2.52 | 1.14 |
| | J3 | 2.23 | 2.33 | 0.66 | 0.98 | 2.57 | 0.84 | 0.78 | 1.97 | 2.63 | 2.16 | 0.33 | 0.24 | 2.94 | 0.82 |
| | J2 + H$_2$O$_2$ | 3.05 | 3.40 | −0.08 | 1.90 | 1.46 | −0.19 | 0.71 | 4.55 | 1.33 | 2.11 | 0.34 | 1.30 | 2.10 | 0.87 |
| | J3 + H$_2$O$_2$ | 1.32 | 3.15 | −0.32 | 1.91 | 2.73 | 0.12 | 0.42 | 1.21 | 2.05 | 2.33 | −0.25 | 0.37 | 1.23 | 0.11 |
| Maxcel | J1 | −0.73 | −0.17 | −0.17 | −0.23 | −0.07 | −0.46 | −0.39 | −0.23 | 0.11 | −0.51 | −0.20 | −0.42 | −0.19 | 0.10 |
| | J2 | −0.83 | 0.66 | −0.60 | 0.56 | −0.39 | 0.45 | 0.49 | 0.14 | 1.12 | −0.11 | 0.29 | 0.00 | 0.52 | 0.93 |
| | J3 | 0.15 | −0.35 | 0.07 | −0.04 | 0.01 | −0.01 | 0.50 | −0.19 | 0.22 | −0.64 | 0.02 | 0.25 | −0.02 | −0.23 |
| | J2 + H$_2$O$_2$ | −0.26 | 1.01 | −0.07 | 0.79 | 1.34 | 0.51 | 0.11 | 0.12 | 2.25 | 1.34 | −0.01 | −0.18 | 0.54 | 0.95 |
| | J3 + H$_2$O$_2$ | 0.18 | 0.17 | 0.13 | 0.52 | 1.45 | −0.13 | 0.36 | 0.45 | 1.17 | 0.50 | 0.21 | 0.21 | 0.44 | 0.52 |
| PRM12 | J1 | 0.48 | −0.03 | −0.70 | 0.22 | −0.12 | 0.24 | −0.23 | 0.80 | 0.50 | −0.21 | 0.06 | −0.90 | 0.40 | 1.61 |
| | J2 | −1.41 | 0.27 | −0.66 | 0.47 | −0.19 | 0.39 | 0.59 | 0.78 | 0.94 | −0.36 | 0.02 | −0.50 | 0.63 | 1.41 |
| | J3 | −0.43 | 0.02 | −0.06 | 0.55 | 0.34 | −0.03 | 0.70 | 0.73 | −0.09 | 0.07 | −0.38 | −0.10 | 0.35 | −0.05 |
| | J2 + H$_2$O$_2$ | 0.42 | 1.71 | 0.39 | 0.86 | 1.42 | 0.39 | 0.65 | 2.22 | 0.81 | 1.83 | −0.03 | 0.10 | 1.11 | 1.72 |
| | J3 + H$_2$O$_2$ | 0.40 | −0.28 | −0.27 | 0.27 | 0.73 | −0.24 | 0.15 | 0.19 | 0.08 | 0.25 | 0.13 | 0.03 | 0.18 | 0.03 |
| Regalis | J1 | 1.83 | 0.89 | −0.07 | 1.26 | 0.86 | 0.40 | 0.01 | −0.44 | 0.77 | 2.10 | −0.07 | −0.40 | 0.31 | 0.31 |
| | J2 | 2.15 | 1.87 | −0.06 | 1.79 | 1.80 | 0.68 | 0.14 | 0.73 | 1.60 | 0.42 | 0.03 | −0.14 | 0.66 | 0.06 |
| | J3 | 2.06 | 1.16 | 0.24 | 1.45 | 2.91 | 0.43 | 0.10 | 0.73 | 1.99 | 1.66 | 0.13 | −0.03 | 0.53 | −0.10 |
| | J2 + H$_2$O$_2$ | 3.72 | 3.19 | −0.08 | 2.61 | 3.32 | 0.41 | 0.21 | 2.30 | 2.78 | 2.14 | −0.08 | −0.13 | 1.25 | 0.48 |
| | J3 + H$_2$O$_2$ | 2.81 | 2.81 | 0.41 | 2.12 | 4.25 | 0.75 | 0.41 | 2.58 | 2.46 | 3.33 | 0.24 | 0.02 | 1.21 | 0.62 |
| Rhodofix | J1 | 3.09 | 0.90 | −0.27 | 2.34 | −0.11 | −0.01 | 0.81 | 2.72 | 2.76 | 1.47 | 0.08 | −0.69 | 2.01 | 0.91 |
| | J2 | 3.18 | 2.97 | −0.57 | 2.02 | 0.86 | 0.73 | 1.24 | 3.50 | 4.17 | 0.84 | 0.86 | −0.31 | 1.79 | 1.59 |
| | J3 | 1.51 | 1.21 | 0.08 | 1.01 | 1.74 | 0.50 | 1.07 | 3.01 | 0.91 | −0.58 | 0.62 | 0.39 | 0.79 | 0.81 |
| | J2 + H$_2$O$_2$ | 3.16 | 2.41 | −0.55 | 1.77 | 1.14 | 0.21 | 0.73 | 2.89 | 3.61 | 0.45 | 0.09 | −0.87 | 1.32 | 0.83 |
| | J3 + H$_2$O$_2$ | 1.32 | 2.97 | −0.08 | 1.11 | 0.80 | 0.18 | 0.67 | 2.21 | 2.30 | 0.87 | 0.08 | −0.57 | 0.98 | −0.17 |
| Stifenia | J1 | 0.15 | −0.85 | −0.64 | −0.44 | −0.32 | −0.42 | −0.71 | −1.08 | −0.32 | 0.33 | −0.48 | −0.07 | −0.12 | −0.42 |
| | J2 | 0.62 | 0.95 | 0.20 | 0.78 | 0.18 | 0.15 | 0.48 | 1.82 | 1.20 | 0.69 | 0.66 | 0.54 | 1.91 | 0.69 |
| | J3 | 0.01 | 0.71 | 0.49 | 7.33 | 0.76 | 0.05 | 0.68 | 2.06 | 2.83 | 0.43 | −0.16 | 1.47 | 5.54 | 0.88 |
| | J2 + H$_2$O$_2$ | 1.45 | 1.07 | −0.71 | 0.84 | 0.65 | 0.48 | 0.31 | 3.30 | 1.94 | 1.14 | −0.03 | 0.51 | −0.33 | 1.06 |
| | J3 + H$_2$O$_2$ | 0.48 | −0.29 | 0.08 | 7.24 | 0.89 | 0.05 | 0.40 | 1.93 | 2.78 | 0.65 | −0.58 | 1.31 | 4.23 | 0.84 |
| Plantomyc. | J1 | −0.03 | −0.59 | −0.02 | −0.03 | 1.37 | −0.09 | −0.08 | 0.21 | 0.14 | 1.36 | 0.12 | 0.27 | 0.29 | 0.00 |
| | J2 | −1.10 | −0.96 | −0.68 | −0.06 | −0.72 | −0.15 | −0.07 | −0.57 | −0.02 | −1.10 | −0.24 | −0.62 | −0.15 | 0.20 |
| | J3 | 0.53 | 0.65 | 0.39 | −0.01 | 0.80 | 0.10 | 0.02 | 0.18 | −0.14 | 1.00 | −0.16 | 0.24 | 0.14 | 0.05 |
| | J2 + H$_2$O$_2$ | 0.28 | 1.46 | −0.37 | 0.65 | 3.03 | −0.04 | −0.01 | 1.06 | 0.99 | 1.47 | −0.01 | −0.27 | 0.47 | 0.55 |
| | J3 + H$_2$O$_2$ | 0.49 | 0.61 | −0.17 | 0.25 | 2.60 | 0.05 | −0.05 | 0.69 | 0.29 | 0.11 | 0.00 | −0.12 | 0.21 | 0.36 |
| Vplaask | J1 | −0.49 | 0.62 | −0.06 | −0.40 | 0.11 | −0.55 | −0.31 | −0.40 | −0.39 | −0.53 | −0.43 | −0.12 | 0.42 | −0.31 |
| | J2 | −0.42 | −0.54 | −0.18 | 1.32 | 0.32 | 0.58 | 0.54 | 3.05 | 0.81 | 1.01 | 0.03 | 0.38 | 1.60 | 1.12 |
| | J3 | 0.26 | 0.49 | −0.47 | 3.32 | 0.75 | −0.02 | 0.74 | −0.16 | 0.95 | 0.56 | −0.21 | 0.46 | 1.95 | 0.36 |
| | J2 + H$_2$O$_2$ | −0.44 | 0.66 | −0.68 | 0.92 | 0.96 | 0.37 | 0.56 | 2.96 | 0.95 | 0.43 | 0.02 | 0.29 | 1.88 | 1.04 |
| | J3 + H$_2$O$_2$ | 0.23 | 0.25 | −0.21 | 3.31 | 2.25 | 0.07 | 0.78 | 0.74 | 0.05 | 1.54 | −0.04 | 0.85 | 2.89 | 0.75 |

TABLE 9-continued

| A Traitement | B Délaide | FAR | CSL | APOX | GST | POX | CAD | CalS | PECT | EDS1 | WRKY | LOX2 | JAR | ACCO | EIN3 |
|---|---|---|---|---|---|---|---|---|---|---|---|---|---|---|---|
| H202 | J2 + $H_2O_2$ | 1.07 | 2.28 | −0.37 | 0.21 | 2.12 | −0.32 | −0.31 | 0.01 | 1.12 | 1.42 | −0.39 | −0.62 | 0.60 | −0.20 |
|  | J3 + $H_2O_2$ | 0.12 | 1.32 | 0.36 | 0.30 | 1.61 | 0.30 | 0.04 | 1.53 | 1.44 | 1.27 | −0.03 | 0.09 | 0.37 | 0.33 |

Key to Tables 8 and 9
A) Treatment
B) Time period
[Translator's Note: Convert all commas to decimal points as concerns numerical entries.]

Test 3: Verification of the Reliability of the Tool on Plants Subjected to 3 Stress Conditions: Light, Heat, Water
Protocol:
Light Stress Golden Delicious seedlings (similar to those in test 2) are moved (Day 0) from the cultivating greenhouse to various greenhouses, climate-controlled chambers or climate-controlled cabinets having qualitatively and quantitatively different lighting systems (Table 10) with a photoperiod of 16 hours per day/8 hours per night, in the case of artificial lighting, and a thermoperiod of 23° C. per day/17° C. per night.

TABLE 10

Tested lighting conditions

| Condition No. | Location | Type of lighting | Temperature control | Humidity |
|---|---|---|---|---|
| Condition 1 | Greenhouse | Natural + neon | Movable sashes | Ambient |
| Condition 2 | Chamber | HPS + MH | Air conditioner | Controlled |
| Condition 3 | Chamber | MH | Air conditioner | Ambient |
| Condition 4 | Chamber | HPIT | Air conditioner | Controlled |
| Condition 5 | Chamber | Neon | Air conditioner | Controlled |
| Condition 6 | Greenhouse | Natural + HPS | Exhaust fan | Ambient |
| Condition 7 | Greenhouse | Natural + HPS | Exhaust fan | Ambient |
| Condition 8 | Greenhouse | Natural + Neon | Exhaust fan + cooling | Ambient |
| Condition 9 | Cabinet | Neon | Air conditioner | Ambient |
| Condition 10 | Cabinet | Neon | Air conditioner | Controlled |

Said seedlings undergo a 24-hour acclimatization period and are then sprayed Bion (0.4 g/l) or water (Day 1), until saturated, using the manual sprayer.

Samplings (identical methodology to that of test 2) are taken on Day 0 prior to moving (3 repetitions of 10 disks), then on Day 1 prior to treatment (3 repetitions of 10 disks), then on Day 3 and Day 4 from the treated batches (1 repetition of 10 disks/treatment/condition).

The samples are extracted and analyzed using the tool according to the invention, in a manner identical to that of test 2. This experiment was carried out once.
Thermal Stress Golden Delicious seedlings (similar to those of test 2) are moved (Day 0) from the cultivating greenhouse to 2 climate-controlled cabinets set to the same photoperiod setting (16 hours per day/8 hours per night) but to two different thermoperiod settings (23° C. by day/17° C. by night or 35° C. by day/17° C. by night).

They undergo a 24-hour acclimatization period and are then sprayed with Bion (0.4 g/l) or water (Day 1) until saturated, using the manual sprayer.

Samplings (identical methodology to that of test 2) are taken on Day 1 prior to treatment, then on Day 4 from the treated batches (1 repetition of 10 disks/temperature treatment/condition/sampling date).

The samples are extracted and analyzed using the tool according to the invention, in a manner identical to that of test 2. Two biological repetitions are carried out.
Water Stress Golden Delicious seedlings (similar to those of test 2) are moved to an experimentation greenhouse (Day 1) and arranged in 3 batches.

One batch immediately undergoes two consecutive sprinklings with PEG6000 at 36% (submersion, drying period and then another submersion) (PEG on Day 1).

After a 24-hour acclimatization period for all of the seedlings, a $2^{nd}$ batch is likewise treated with PEG6000, in an identical manner to that above (PEG on Day 0).

All of the batches are then sprayed with the manual sprayer until saturated, with half Bion (0.4 g/l) and half water.

Samples (identical methodology to that of test 2) are taken on Day 0 from the batch not treated with PEG, and prior to the Bion and water treatment; then, on Day 2 and Day 3, from all of the batches (1 repetition of 10 disks/treatment/water condition/date of sampling).

The samples are extracted and analyzed using the tool according to the invention, in a manner identical to that of test 2. This experiment was carried out once.
Results:
Light Stress The expression results for the 28 target genes are detailed below in Tables 11 and 12; these results are distributed over several tables, for presentation purposes only.

In these tables, the lines correspond, respectively to:
"Untreated"=modulations observed 24 hours (Day 1) after movement from the cultivating greenhouse;
"Water" and "Bion"=average modulations observed in the seedling leaves sprayed with Bion and water, respectively, 48 and 72 hours after treatment, namely 3 and 4 days after being moved from the cultivating greenhouse (Day 3 and Day 4), averaged, in the seedlings sprayed with Bion and water, respectively.

Observation of the induction profiles of the seedlings after 24 hours of acclimatization under various lighting conditions (Tables 11 and 12) show a correlation between power (and spectrum) of the auxiliary lighting and induction of the genes of the phenylpropanoid pathway.

Analysis of the profiles after treatment of the seedlings with Bion, or with water, reveals that the most stressful lighting conditions do not enable a strong inductive capacity to be demonstrated with regard to Bion, in particular with regard to the PR proteins (Table 11), which is not the case for the less stressful conditions.

However, a few genes are less sensitive to the lighting conditions than those encoding certain PR proteins or enzymes of the phenylpropanoid pathway and enabling demonstration of the stimulating effect of Bion under the majority of conditions: this involves PR5, FAR and EDS1.

Thermal Stress

The averaged expression results for the 28 target genes are detailed in Tables 13 and 14; these results are distributed over several tables, for presentation purposes only.

The legend for these tables is as follows: Normal T°=23° C. by day/17° C. by night; normal and then stressful T° after treatment=23° C. by day/17° C. by night for 24 hours, then 35° C. by day/17° C. by night; Stressful and then normal T° after treatment=35° C. by day/17° C. by night for 24 hours, and then 23° C. by day/17° C. by night.

Thermal stress conditions (35° C.) are capable of strongly activating some genes of the tool according to the invention, in particular several PR proteins in the control seedlings (treated with water), when the stress is maintained over the entire experiment (4 days), or applied immediately after spraying with water (Tables 13 and 14).

This induction is correlated with a strong repression of the genes of the phenylpropanoid pathway (except for PPO).

These induction/repression effects are temporary, until the stress is interrupted, since they are no longer observed in the control seedlings stressed for 24 hours and then returned to "normal" conditions.

The induction of certain PR proteins, caused by thermal stress, applied up to the date of sampling, masks the ability of Bion to induce the PR proteins (Table 13).

However, other genes of the tool enable the effect of Bion to be revealed, even under these stressful conditions, because they are weakly induced by thermal stress alone (CSL, POX, WRKY).

Finally, temporary thermal stress applied a few hours prior to treatment with Bion does not interfere with demonstrating the inductive effect of this product.

Water Stress

The expression results for the 28 target genes are detailed in Tables 15 and 16; the results are distributed over several tables, for presentation purposes only.

In the apple tree seedlings, water stress, as applied (PEG) does not alone induce the genes of the tool (Tables 15 and 16): no clear differences are observed between the expression profiles obtained in the 3 batches of plants, which are stressed or unstressed and sprayed with water. In addition, it does not appear to interfere with the inductive effect of Bion, which is shown under the 3 conditions.

Conclusion

These experiments demonstrate the benefit of studying several groups of defense genes, or even several genes within each group, in order to reveal the stimulating effect of a candidate NDS.

As a matter of fact, slightly stressful environmental conditions (bright lighting and high temperature) can in and of themselves induce some defense genes present in the tool according to the invention and mask the effects of the NDSs.

In order to use the tool optimally, for the purpose of screening candidate products, it is however advised to conduct experiments under moderate artificial lighting conditions and under thermal conditions as controlled as possible. Within reason, of course, water stress should not interfere with the use of the tool.

TABLE 11

| | | | PR1 | PR2 | PR4 | PR5 | PR8 | PR14 | PR15 | PAL | ANS | CHS | DFR | PPO | HMGR | FPPS |
|---|---|---|---|---|---|---|---|---|---|---|---|---|---|---|---|---|
| C1 = Serre 1 d'élevage | Non traité | | 0.17 | −0.11 | −0.53 | −0.59 | 0.28 | −0.13 | −0.49 | 0.04 | 0.07 | −0.11 | −0.17 | −0.58 | 0.27 | −0.12 |
| C2 = Chambre climatique 1 | Non traité | A | −0.62 | −0.18 | −1.14 | −1.98 | 1.73 | −1.02 | −0.96 | 6.72 | 6.96 | 6.58 | 6.30 | −1.08 | −1.22 | −2.25 |
| (éclairage | Eau | B | −1.00 | −0.23 | −2.57 | 1.46 | 2.22 | −1.56 | 0.03 | 5.84 | 5.52 | 5.44 | 4.28 | 0.53 | 0.02 | −1.91 |
| HPS + MH) | Bion | C | 0.37 | 0.99 | −0.53 | 5.11 | 3.70 | −0.26 | −0.13 | 5.90 | 5.78 | 5.42 | 4.33 | 0.18 | 0.92 | −2.06 |
| C3 = Chambre climatique 2 | Non traité | | −0.20 | 0.40 | −0.90 | −0.32 | 2.30 | −0.19 | −0.24 | 5.48 | 5.27 | 5.18 | 4.75 | 0.11 | −0.66 | −0.96 |
| (éclairage MH) | Eau | | −0.44 | 3.52 | −0.39 | 3.06 | 2.68 | −1.02 | −0.11 | 4.83 | 3.94 | 4.34 | 3.39 | −0.59 | 0.19 | 0.06 |
| | Bion | | 0.38 | 1.95 | −0.44 | 5.30 | 4.83 | −1.07 | −1.09 | 4.80 | 4.33 | 4.25 | 3.56 | 0.43 | 1.06 | −0.99 |
| C4 = Chambre climatique 3 | Non traité | | −0.30 | 0.10 | −1.32 | −0.80 | 0.16 | −0.71 | −0.40 | 5.67 | 5.18 | 5.04 | 4.13 | −0.65 | −0.74 | −1.87 |
| (éclairage naturel + HPIT) | Eau | | −0.21 | −0.95 | −1.15 | 2.06 | 1.72 | −0.92 | 0.34 | 3.05 | 3.73 | 3.56 | 2.31 | 0.14 | −0.25 | −0.05 |
| | Bion | | 2.98 | 5.12 | 4.90 | 6.72 | 6.05 | 0.30 | 2.61 | 3.73 | 3.16 | 3.57 | 2.36 | 3.02 | 1.91 | 0.37 |
| C5 = Chambre climatique 4 | Non traité | | −0.47 | −0.19 | −3.56 | −0.47 | 0.96 | −0.97 | −0.20 | 3.99 | 4.55 | 4.10 | 4.04 | −0.88 | −1.14 | −1.39 |
| (éclairage neon ACTIVA172) | Eau | | −0.66 | −1.56 | −1.39 | 2.19 | 1.12 | −1.85 | −0.02 | 3.88 | 4.87 | 4.37 | 3.25 | 0.22 | −0.67 | −1.23 |
| | Bion | | −0.38 | 3.73 | 0.97 | 6.49 | 4.67 | −0.62 | 1.83 | 4.54 | 5.28 | 4.91 | 3.81 | −0.05 | 0.33 | −1.27 |
| C6 = Serre 2 (éclairage naturel + HPS) | Non traité | | 0.46 | 0.16 | −1.65 | 0.05 | 2.03 | −0.50 | 0.31 | 5.20 | 5.25 | 5.13 | 4.63 | −0.42 | −0.66 | −1.59 |
| | Eau | | 0.33 | −0.35 | −0.87 | 0.60 | 2.93 | −0.72 | 0.24 | 6.13 | 5.93 | 5.62 | 4.65 | 1.30 | −0.15 | −1.21 |
| | Bion | | 3.23 | 7.90 | 6.36 | 6.13 | 6.24 | 1.70 | −0.89 | 4.86 | 5.11 | 4.78 | 4.11 | 2.22 | 1.40 | −1.16 |
| C7 = Serre 3 (éclairage naturel + HPS) | Non traité | | −0.05 | 0.23 | −1.10 | −0.62 | 1.63 | −0.13 | 0.33 | 3.44 | 1.65 | 2.50 | 0.15 | −0.65 | −0.16 | −0.59 |
| | Eau | | −0.42 | −1.23 | −2.61 | 1.36 | 1.25 | −0.57 | 0.48 | 3.42 | 3.43 | 3.51 | 2.34 | 0.21 | −0.58 | −0.85 |
| | Bion | | 1.62 | 6.48 | 5.54 | 7.45 | 6.08 | 1.66 | 1.60 | 4.55 | 4.48 | 3.98 | 3.72 | 2.72 | 1.68 | −0.05 |
| C8 = Serre 4 (éclairage naturel + néon) | Non traité | | 0.23 | 0.50 | −0.94 | 0.19 | 1.26 | −0.30 | 0.55 | 0.89 | 0.03 | 0.22 | −0.68 | −0.01 | −0.03 | 0.44 |
| | Eau | | 0.23 | 0.38 | −0.49 | 2.31 | 2.28 | 0.04 | 0.29 | 1.37 | 1.11 | 1.28 | −0.22 | 0.08 | 0.58 | 0.75 |
| | Bion | | 2.58 | 8.28 | 8.08 | 7.30 | 7.92 | 5.60 | 1.82 | 3.44 | 1.61 | 1.84 | 0.88 | 3.93 | 3.00 | 1.60 |
| C9 = Armoire 1 (éclairage néon) | Non traité | | −1.55 | −0.64 | 0.11 | −0.55 | 1.34 | 0.24 | 0.14 | 2.66 | 3.14 | 3.04 | 3.40 | −0.39 | −0.04 | −1.15 |
| | Eau | | 0.64 | 1.16 | 1.38 | 1.73 | 3.19 | 1.24 | 1.75 | 2.79 | 3.26 | 2.88 | 3.56 | 0.81 | 1.10 | −0.59 |
| | Bion | | 2.32 | 7.42 | 8.21 | 4.16 | 5.81 | 2.07 | 1.83 | 1.91 | 1.82 | 2.29 | 3.27 | 2.41 | 0.05 | |
| C10 = Armoire 2 (éclairage néon) | Non traité | | 0.20 | −0.41 | −1.62 | −0.72 | 0.72 | 2.85 | 0.03 | 2.38 | 3.27 | 2.78 | 3.62 | −1.76 | −0.50 | −0.67 |
| | Eau | | 2.25 | 5.52 | 1.79 | 3.62 | 3.70 | 6.49 | −0.26 | 0.22 | 1.07 | 0.60 | 2.03 | −1.49 | 0.75 | −0.17 |
| | Bion | | 2.84 | 8.57 | 6.78 | 4.63 | 5.43 | 5.37 | −0.16 | 1.87 | 2.48 | 2.19 | 3.17 | 1.84 | 2.24 | −0.25 |

TABLE 12

|  |  | FAR | CSL | APOX | GST | POX | CAD | CalS | PECT | EDS1 | WRKY | LOX2 | JAR | ACCO | EIN3 |
|---|---|---|---|---|---|---|---|---|---|---|---|---|---|---|---|
| C1 = Serre 1 d'élevage | Non traité | −0.76 | −0.27 | 0.18 | −0.17 | 0.77 | 0.19 | −0.01 | −0.18 | −0.23 | −0.22 | 0.07 | −0.03 | −0.05 | 0.03 |
| C2 = Chambre climatique 1 (éclairage HPS + MH) | Non traité | −6.15 | 4.58 | 1.08 | −2.55 | 0.80 | 0.39 | −1.10 | 0.40 | −1.20 | −0.55 | 0.36 | −0.02 | −0.84 | −0.58 |
|  | Eau | −3.36 | 2.96 | 0.54 | −2.89 | 1.08 | 0.03 | −1.19 | −1.05 | 0.47 | −0.06 | −0.86 | −1.28 | −1.90 | −0.81 |
|  | Bion | −0.35 | 2.94 | 0.26 | −2.84 | 2.09 | 0.17 | −1.05 | −0.12 | 3.08 | −0.50 | −1.44 | −1.40 | −1.38 | −0.24 |
| C3 = Chambre climatique 2 (éclairage MH) | Non traité | −0.24 | 2.93 | 1.37 | −1.31 | 1.30 | 0.58 | −0.62 | 0.66 | −0.35 | −0.26 | 0.79 | 0.55 | −0.17 | 0.65 |
|  | Eau | 1.75 | 2.11 | 0.66 | −2.02 | 1.30 | 0.20 | −1.13 | −0.64 | 1.32 | 0.76 | −0.45 | 0.49 | −0.67 | 0.30 |
|  | Bion | 3.62 | 2.31 | 0.78 | −1.77 | 1.92 | 0.22 | −0.73 | 0.72 | 4.31 | −0.12 | 0.06 | 0.46 | −0.90 | 0.69 |
| C4 = Chambre climatique 3 (éclairage naturel + HPIT) | Non traité | −1.46 | 2.30 | 1.59 | −2.20 | 0.58 | 0.03 | −0.80 | −0.51 | −1.04 | −0.12 | 0.39 | −0.14 | −1.19 | −0.20 |
|  | Eau | 0.41 | 2.21 | 0.85 | −0.62 | 0.02 | 0.42 | −0.35 | −0.81 | 0.03 | −0.59 | −0.50 | −0.14 | 0.18 | 0.08 |
|  | Bion | 2.77 | 3.62 | 0.88 | −0.37 | 2.03 | 0.70 | −0.38 | 1.36 | 4.31 | 3.88 | −0.65 | −0.18 | 0.78 | 1.00 |
| C5 = Chambre climatique 4 (éclairage néon ACTIVA172) | Non traité | −1.06 | 2.44 | 1.11 | −2.03 | 1.83 | 0.29 | −0.91 | −0.60 | −1.63 | −0.53 | 0.17 | −0.05 | −0.69 | −0.72 |
|  | Eau | 0.93 | 1.88 | 0.85 | −2.64 | 1.31 | −0.07 | −1.16 | −1.74 | 0.25 | −1.08 | −0.70 | −0.39 | −0.54 | −0.59 |
|  | Bion | 3.38 | 2.84 | 1.14 | −2.67 | 2.93 | 0.21 | −0.98 | −0.38 | 3.73 | 1.17 | −0.64 | −0.10 | −0.70 | −0.06 |
| C6 = Serre 2 (éclairage naturel + HPS) | Non traité | 0.34 | 2.96 | 1.01 | −2.08 | 1.99 | 0.54 | −0.87 | −0.43 | 0.19 | 1.47 | 0.65 | 0.27 | −0.70 | −0.51 |
|  | Eau | 2.57 | 3.59 | 1.05 | −2.46 | 2.45 | 0.33 | −0.82 | −0.24 | 0.48 | −0.21 | 0.68 | 0.14 | −0.48 | 0.55 |
|  | Bion | 5.30 | 4.54 | 0.91 | −1.58 | 4.03 | 0.39 | −1.12 | 1.60 | 4.35 | 4.24 | 0.37 | −0.22 | 0.52 | 1.14 |
| C7 = Serre 3 (éclairage naturel + HPS) | Non traité | −0.44 | −0.06 | 0.75 | −1.02 | 1.26 | 0.07 | −0.38 | −0.23 | −0.10 | 0.91 | 0.86 | 0.49 | −0.57 | 0.21 |
|  | Eau | 1.78 | 1.04 | 0.88 | −2.07 | 1.54 | 0.04 | −1.08 | −1.02 | 0.36 | 0.29 | −0.45 | −0.31 | −0.33 | −0.01 |
|  | Bion | 5.67 | 4.22 | 1.42 | −0.93 | 3.37 | 0.48 | −0.54 | 1.25 | 4.44 | 1.78 | −0.11 | 0.55 | 0.31 | 0.96 |
| C8 = Serre 4 (éclairage naturel + néon) | Non traité | −1.20 | −0.37 | 0.95 | 0.04 | 0.70 | 0.23 | 0.27 | 0.33 | −0.54 | 1.27 | 0.65 | 0.80 | 0.38 | −0.32 |
|  | Eau | 0.38 | 1.52 | 0.45 | −0.40 | 0.97 | 0.30 | −0.07 | 0.12 | 0.40 | 1.45 | 0.15 | 0.34 | 0.55 | 0.28 |
|  | Bion | 4.83 | 5.99 | 0.90 | 1.52 | 5.50 | 0.63 | 0.33 | 2.42 | 5.40 | 5.02 | −0.17 | −0.13 | 2.06 | 2.01 |
| C9 = Armoire 1 (éclairage néon) | Non traité | −0.27 | 0.97 | 0.25 | −1.86 | −0.78 | 0.00 | −0.72 | −0.05 | 0.85 | −1.20 | −0.07 | −0.50 | −0.79 | 0.15 |
|  | Eau | 2.86 | 2.06 | 0.21 | −1.14 | 2.36 | −0.22 | −0.12 | 2.61 | 3.05 | 2.13 | 0.19 | −0.66 | −0.82 | 1.05 |
|  | Bion | 5.22 | 3.67 | 0.77 | 0.07 | 3.36 | 0.03 | −0.15 | 2.90 | 5.30 | 5.37 | −0.08 | −0.58 | 1.02 | 0.91 |
| C10 = Armoire 2 (éclairage néon) | Non traité | −0.14 | 1.45 | 0.12 | −0.57 | −0.55 | 0.00 | −0.96 | 1.36 | 0.32 | −0.20 | 0.10 | 0.11 | −0.05 | 0.73 |
|  | Eau | 3.59 | 0.52 | 0.13 | −0.09 | 1.75 | −0.02 | −0.31 | 3.18 | 3.27 | −1.10 | −0.24 | −0.26 | −0.17 | 0.67 |
|  | Bion | 5.00 | 2.53 | 0.32 | 0.43 | 4.22 | 0.36 | −0.64 | 4.23 | 4.88 | 3.94 | −0.16 | −0.54 | 0.73 | 1.24 |

Key to Tables 11 & 12
C1 = Cultivating greenhouse 1
C2 = Climate-controlled chamber 1 (MH lighting + HPS)
C3 = Climate-controlled chamber 2 (MH lighting)
C4 = Climate-controlled chamber 3 (natural lighting + HPIT)
C5 = Climate-controlled chamber 4 (neon lighting ACTIVA172)
C6 = Greenhouse 2 (natural lighting + HPS)
C7 = Greenhouse 3 (natural lighting + HPS)
C8 = Greenhouse 4 (natural lighting + neon)
C9 = Cabinet (neon lighting)
C10 = Cabinet (neon lighting)
A) Untreated
B) = Water
C) = Bion
[Translator's Note: Convert all commas to decimal points as concerns numerical entries.]

TABLE 13

|  | E |  | PR1 | PR2 | PR4 | PR5 | PR8 | PR14 | PR15 | PAL | ANS | CHS | DFR | PPO | HMGR | FPPS |
|---|---|---|---|---|---|---|---|---|---|---|---|---|---|---|---|---|
| A | T° normales | Eau | 0.99 | −1.03 | −0.48 | 2.02 | 0.63 | −1.46 | −0.77 | −1.05 | −1.05 | −1.03 | −1.68 | −0.4 | 0.91 | −1.39 |
|  |  | Bion | 3.79 | 6.22 | 7.77 | 4.21 | 3.67 | 1.89 | −0.57 | −2.16 | −1.35 | −1.64 | −1.77 | −0.76 | 1.63 | −1.12 |
| B | T° normales puls stressantes | Eau | 5.59 | 7.91 | 9.28 | 1.34 | 3.53 | 7.13 | −0.01 | −4.77 | −4.96 | −5.65 | −4.77 | 0.13 | 1.36 | 0.77 |
|  |  | Bion | 9.82 | 11.2 | 12.9 | 4.34 | 6.38 | 7.86 | 0.66 | −3.71 | −4.7 | −5.86 | −5.39 | 2.82 | 4.36 | 1.18 |
| C | T° stressantes | Eau | 7.02 | 7.46 | 9.57 | 2.04 | 4.78 | 4.79 | 4.62 | −3.96 | −4.6 | −5.04 | −5.27 | 1.61 | 2.43 | 0.92 |
|  |  | Bion | 9.55 | 11.3 | 14 | 3.71 | 7.96 | 9.23 | 4.65 | −3.93 | −5.29 | −6.17 | −5.36 | 5.42 | 4.77 | 1.36 |
| D | T° stressantes puls normales | Eau | 2.95 | 1.1 | −0.87 | 2.64 | 2.19 | −0.27 | −0.07 | −1.19 | −0.5 | −1.01 | −1.08 | −1.54 | 1.48 | −1.14 |
|  |  | Bion | 6.46 | 8.67 | 9.55 | 4.9 | 5.36 | 4.57 | 0.12 | −1.95 | −1.94 | −2.48 | −1.63 | 1.35 | 3.17 | 0.77 |

TABLE 14

| | | E | FAR | CSL | APOX | GST | POX | CAD | CalS | PECT | EDS1 | WRKY | LOX2 | JAR | ACCO | EIN3 |
|---|---|---|---|---|---|---|---|---|---|---|---|---|---|---|---|---|
| A | T° normales | Eau | 2.44 | −0.24 | −1.29 | −1.05 | −1.03 | −0.25 | −0.45 | 0.48 | 2.02 | 1.15 | 0.19 | −1.04 | −0.8 | 0.32 |
|   |   | Bion | 3.34 | 0.91 | −0.97 | −0.33 | 1.96 | 0.11 | −0.54 | 1.22 | 2.96 | 0.93 | 0.16 | −0.82 | −0.24 | 0.14 |
| B | T° normales | Eau | 1.16 | 0.82 | −1.45 | 2.4 | 0.97 | 0.43 | 1.12 | 3.49 | 2.56 | 1.03 | 1.35 | 1.03 | 1.69 | 1.94 |
|   | puls stressantes | Bion | 0.45 | 4.65 | −1.18 | 1.89 | 5.54 | 0.4 | 1.05 | 2.04 | 4.79 | 5.48 | −0.66 | −0.63 | 1.29 | 0.98 |
| C | T° | Eau | 1.16 | 1.26 | −1.23 | 2.28 | 1.96 | 0.66 | 0.65 | 2.77 | 2.46 | 1.51 | 0.49 | 0.45 | 1.16 | 1.29 |
|   | stressantes | Bion | −0.47 | 6.17 | −0.56 | 2.83 | 6 | 0.93 | 1.3 | 2.56 | 4.44 | 4.66 | −0.64 | −0.83 | 1.52 | 1.23 |
| D | T° | Eau | 1.88 | −0.13 | −0.86 | −0.4 | 0.79 | −0.03 | −0.29 | 1.16 | 2.45 | −0.58 | 0.39 | −0.72 | −0.61 | 0.82 |
|   | stressantes puls normales | Bion | 4 | 2.71 | −0.57 | 1.68 | 3.72 | 0.19 | 0.09 | 1.9 | 3.73 | 4.93 | −0.15 | −0.59 | 1.27 | 0.89 |

Key to Tables 13 and 14
A) Normal temperatures
B) Normal then stressful temperatures
C) stressful temperature
D) Stressful then normal temperatures
E) Water
[Translator's Note: Convert all commas to decimal points as concerns numerical entries.]

TABLE 15

| | | | | PR1 | PR2 | PR4 | PR5 | PR8 | PR14 | PR15 | PAL | ANS | CHS | DFR | PPO | HMGR | FPPS |
|---|---|---|---|---|---|---|---|---|---|---|---|---|---|---|---|---|---|
| A | Arrosage normal | B | Eau | −1.0 | 4.7 | 5.1 | 1.8 | 1.3 | 1.3 | −0.3 | 1.3 | 1.8 | 1.8 | 0.7 | −0.1 | −0.1 | 0.2 |
|   |   | C | Bion | 2.8 | 10.3 | 12.0 | 5.2 | 5.0 | 5.0 | −0.4 | 1.3 | 1.1 | 1.1 | 0.9 | 5.1 | 2.4 | 1.0 |
| D | PEG à J-1 | | Eau | 0.1 | 1.5 | 5.7 | 1.8 | 1.6 | 3.5 | 0.5 | 0.9 | 1.5 | 1.7 | 1.1 | 0.2 | 0.2 | −0.3 |
|   |   | | Bion | 7.2 | 10.8 | 11.0 | 6.2 | 4.6 | 7.3 | 0.0 | 1.3 | 1.4 | 1.6 | 1.4 | 2.7 | 1.9 | 0.5 |
| E | PEG à J0 | | Eau | 1.8 | 4.0 | 7.9 | 0.8 | 2.5 | 1.0 | −0.3 | 1.0 | 2.1 | 1.6 | 0.7 | 1.9 | 0.2 | 0.0 |
|   |   | | Bion | 7.1 | 10.6 | 11.0 | 6.1 | 4.8 | 4.5 | −1.0 | 0.9 | 1.5 | 1.3 | 1.3 | 2.6 | 1.9 | 0.1 |

TABLE 16

| | | | | FAR | CSL | APOX | GST | POX | CAD | CalS | PECT | EDS1 | WRKY | LOX2 | JAR | ACCO | EIN3 |
|---|---|---|---|---|---|---|---|---|---|---|---|---|---|---|---|---|---|
| A | Arrosage normal | Eau | B | 1.2 | 1.1 | 0.3 | 0.1 | −1.2 | −0.5 | 0.1 | −0.3 | 1.6 | −0.3 | −0.3 | −0.2 | 0.2 | −2.1 |
|   |   | Bion | C | 4.0 | 5.5 | 0.1 | 1.6 | 2.0 | −0.3 | −0.2 | 1.5 | 4.7 | 5.9 | −0.5 | −0.3 | 1.8 | −0.7 |
| D | PEG à J-1 | Eau | | 3.0 | 1.8 | 0.4 | 0.4 | −0.9 | 0.0 | 0.0 | 1.6 | 1.3 | 0.2 | 0.7 | 0.2 | 0.9 | −1.4 |
|   |   | Bion | | 5.9 | 4.7 | 0.9 | 1.1 | 1.0 | −0.1 | 0.3 | 2.7 | 4.4 | 5.1 | 1.1 | 0.5 | 2.1 | −0.4 |
| E | PEG à J0 | Eau | | 2.8 | 1.7 | 0.6 | 0.4 | −2.0 | 0.1 | 0.5 | 0.7 | 1.1 | 0.2 | 1.1 | 0.4 | 0.8 | −1.6 |
|   |   | Bion | | 5.0 | 4.7 | 0.4 | 1.0 | 2.0 | −0.2 | 0.1 | 1.5 | 4.4 | 3.7 | 0.5 | 0.0 | 1.2 | −0.9 |

Key to Tables 15 and 16
A) normal sprinkling
B) Water
C) Bion
D) PEG on Day 1
E) PEG on Day 0
[Translator's Note: Convert all commas to decimal points as concerns numerical entries.]

Test 4: Verification of the Ability of the Tool to Study Various Apple Varieties for the Response Thereof to NDSs
Method:

This experiment was carried out once on grafted young maiden trees of 4 actively growing varieties: Braeburn, Gala, Granny Smith, MM106, which are grown directly in an experimental greenhouse.

For Analysis of Defenses

The maiden trees are sprayed with Bion (0.4 g/l) or water (Day 0) until saturated, using a compressed-air sprayer.

Samples of the leaves F3 ($3^{rd}$ foliar stage, young leaves still not completely developed) are taken on Day 0 (prior to treatment) and on Day 3 from all of the treated batches (three half-blades sampled from three leaves F3 (young, not completely developed leaves) pooled/sampling).

The samples are extracted and analyzed using the tool, in a manner identical to that of test 2.

For Analysis of the Protective Power

The maiden trees are sprayed with Bion (0.4 g/l) or water (Day 0) in the same way, until saturated, using the compressed-air sprayer.

On Day 4, the 2 youngest developed leaves (F1 and F2) of each maiden tree are cut by two thirds and perpendicular to the main vein, using scissors that have been previously dipped in a bacterial suspension of *Erwinia amylovora* prepared in sterile water at $10^8$ cfu/ml. A dozen actively growing shoots were inoculated by variety and treatment.

Grading of the symptoms, i.e., the presence of a necrosis on the vein of the inoculated leaves (noted as 0.5), or having reached the petiole (noted as 1), having evolved along the stem (noted as 1+length of necrosis on stem in cm), is carried out 3 weeks after inoculation. The average length of necrosis on sprayed maiden trees ($\mu_{cau}$) is calculated, and the relative protection effectiveness of the Bion is estimated according to the formula: $100-((Lg_{Bion}\times100)/\mu_{cau})$.

Results:

Bion causes inductions in the 4 varieties according to a rather similar qualitative profile (FIG. 2A).

Quantitatively, no variety is identified that "responds" globally more strongly than another. The differences in induction levels vary in amplitude according to the genes.

As concerns the protection effectiveness of Bion on these 4 varieties, against fire blight, marked differences are observed, Granny Smith being the variety most "responsive" to Bion, and Gala being the least "responsive" one (FIG. 2B).

Conclusion

The tool fine-tuned on Golden Delicious seedlings can therefore be used on other varieties of apples. It enables the reactivity to the Bion treatment, of the other 4 varieties tested here: Braeburn, Gala, Granny Smith and MM106 to be revealed, a reactivity that is confirmed by the protection observed after artificial inoculation with E. amylovora.

The invention claimed is:

1. A device for determining or studying the natural defense stimulation state of plants or plant portions, which device includes means for determining the expression level of a combination of target genes in a sample of plants or plant portions, said determination means including:
 (a) a means of determining the expression level of the target genes PR-2 and PR-4;
 (b) a means of determining the expression level of at least one target gene chosen from PAL or CHS;
 (c) a means of determining the expression level of the target gene Far;
 (d) a means of determining the expression level of the target gene CSL;
 (e) a means of determining the expression level of the target genes GST and POX;
 (f) a means of determining the expression level of the target genes CalS and Pect;
 (g) a means of determining the expression level of the target gene EDS 1;
 (h) a means of determining the expression level of the target gene LOX2; and
 (j) a means of determining the expression level of the target gene EIN3,
 wherein said means for determining the expression level of target genes are chosen from among (i) nucleic acid fragments capable of hybridizing specifically with mRNAs expressed by said target genes or with corresponding cDNAs, or with fragments of said mRNAs or said cDNAs, and/or (ii) the antibodies bonding specifically with the expression products of said target genes, said mRNAs or said cDNAs, or fragments of said expression products, and
 wherein said nucleic acid fragments and said antibodies are immobilized on a substrate.

2. The device according to claim 1, wherein said nucleic acid fragments consist of nucleotide primers that hybridize specifically with the mRNAs, cDNAs or with fragments thereof.

3. The device according to claim 2, wherein said nucleotide primers are suitable for determining the expression level of the target genes by means of a quantitative PCR method.

4. The device according to claim 3, wherein the primers are chosen from among the following sequences: SEQ ID Nos. 32 to 87.

5. The device according to claim 1, which consists of a DNA chip.

6. The device according to claim 1, which includes the means for determining the expression level of the following combination of target genes: PR-2, PR-4, CHS, PPO, Far, CSL, GST, POX, CalS, Pect, EDS1, LOX2, and EIN3.

7. The device according to claim 1, which includes the means for determining the expression level of the following combination of target genes: PR-2, PR-4, PAL, PPO, Far, CSL, GST, POX, CalS, Pect, EDS1, LOX2, and EIN3.

* * * * *

SEQUENCE LISTING

```
<160> NUMBER OF SEQ ID NOS: 93

<210> SEQ ID NO 1
<211> LENGTH: 304
<212> TYPE: DNA
<213> ORGANISM: Malus domestica

<400> SEQUENCE: 1
tacctcaatt cccacaacgc cgctcgagca gcagtaggcg ttggtccctt gacgtgggat      60
gacaatgtag caggctatgc acaaaactac gccaaccaac atgttggcga ctgcaatctc     120
gtgcactccg gtgggccata cggtgaaaac cttgccatga gcactggtga catgtcggga     180
gcagcggctg tggacctgtg ggtggcggag aaagccgact acagttatga gtcgaactcg     240
tgtgctgctg gaaaggtgtg tgggcattat acacaggtgg tttggcgtaa ctcggctcgt     300
gtag                                                                  304

<210> SEQ ID NO 2
<211> LENGTH: 320
<212> TYPE: DNA
<213> ORGANISM: Malus domestica

<400> SEQUENCE: 2
tatgctcttt tcacagctcc gtcagtttta gtacaagatg gccaacgtgg ttatcgtaat      60
cttttcgatg ccattttgga tgctgtttac gctgcgcttg acaaggtcgg tggaggatct     120
ttggaaattg ttatatcgga gagtggttgg ccgacagctg gtgggacggc aacaacagtt     180
gataatgcga ggacatataa ctcgaatttg gttcaacatg tgaagggagg gactccaagg     240
aagcctggaa ggcccattga aacttacatc tttgccatgt ttgatgagaa tagaaagacc     300
ccagagcttg agaaacattg                                                 320

<210> SEQ ID NO 3
<211> LENGTH: 609
<212> TYPE: DNA
<213> ORGANISM: Malus domestica

<400> SEQUENCE: 3
aagccttcca agaacaacag agatattgta gattattgcc tgcttgattc ggaaaattac      60
atatcacaac atggccggga agatcacagc aagctctgtg ttgtttgttt cgatcatgat     120
ctgtggtttg gtcggcagtg cattgggaca aagtgcgacg aatgtgagag ccacatacca     180
cctctacaat ccacagcaaa acaattacga cttgcgggca gtaagtgcct actgcgcaac     240
atgggatgcc gataaatccc tcgaatggcg cagcaaatat ggatggactg ccttttgcgg     300
acctgctggc cctactgggc aagccgcatg cggaaggtgc ctcttggtga caaacactcg     360
gactggagct caagcaacgg tgagaattgt tgatcagtgc agcaacggag gattggactt     420
ggacgtgaat gtttttaacc aaattgacac cgacggcaat ggttaccaac aaggccacct     480
```

```
tatcgtcaac tacgactttg tcgactgcgg cgactaaagc ctgtaaacct taatttttc      540 aatagctata tagttctcta cttccagtat tggtaaggaa cttaactatg tattactaat      600
aaataagct                                                              609

<210> SEQ ID NO 4
<211> LENGTH: 583
<212> TYPE: DNA
<213> ORGANISM: Malus domestica

<400> SEQUENCE: 4
actacaaatt ttggtaaagc ttagctccca caatgagcct ccttaaaagc ctcttagttt       60
tctccatcct atgtgccatt ctcttctttg catcaaccaa tgcagctcga tttgacatcc      120
aaaacaactg tgcctacact gtatgggcag ctgctgtgcc aggcggtggc cgccagctcg      180
gcaaaggcca atcctgggcc ttagatgtga gtgctgtac caaagggct cgcatttggg       240 gccggacggg atgcaacttc gatggagcag acgtggcaa atgccaaacg ggtgattgtg       300
ggggtgtcct ccaatgccaa ggctatggtc aaccaccaaa caccctagct gaatatgccc      360
ttaatcaatt taacaacttg gatttcattg acatctctct tgttgatggg tttaatgtac      420
ctatggaatt tagtcccacg tctggtgggt gcactaggag gattaggtgc acggctgata      480
ttaacgggca gtgccctaac caactgaggg ctccaggagg ctgcaacaac ccttgcactg      540
tgttcaagac tgatcaatat tgttgcaatt ctggaaattg tgg                        583

<210> SEQ ID NO 5
<211> LENGTH: 1011
<212> TYPE: DNA
<213> ORGANISM: Malus domestica

<400> SEQUENCE: 5
atggcatcca aaacacaaac cctagcccta actctgtccc tcttgatcct catttcttca       60
tgcaagtcct cccaagccgc cggaatcgcg acgtattggg ccaaaacgg caacgaagga      120 accctagcag aagcttgcaa ctcgggcaac taccagtttg ttaacatagc tttcctctca      180
acttttggaa caaccaagc ccctgtccta aacctcgccg ccactgcaa ccccgctagt       240 ggtacttgca cggggcagag tgccgacatc agaacctgcc aatcaaaaaa cataaaagtc      300
ctcctctcga ttggagggc caccgaaact tactctctca cttcagctga tgaggcaagg      360
caagttgctg attacatctg gaacaacttc ctaggtggtc agtcagattc gcgcccgctt      420
ggggacgcgg ttttggacgg cgtcgatttc gacattgagt tgggtggtac gcagttctac      480
gacgagctcg ccaggtcact caaaggacac aacggacagg gaaaaacggt ctatttagcc      540
gcagctccac aatgcccgtt cccggatact cacctagacg cgctatcca aaccggttta       600 tttgactacg tttgggttca gttctacaac aaccccctag cccaatgcca gtatgcagac      660
ggtaatgccg acgctctttt gagcagttgg aaccgatggg cctcggtttc ggccacccag      720
gtgttcatgg ggtaccggc agctcctgag gccgctccga gcggcggatt tattcctgct      780
gacgctctca agtcacaagt tcttccaacg attaagaatt cgcccaagta cggaggagtt      840
atgctttgga gcaggttcta tgacaacggt tatagtgcat ccattaagga cagcatctaa      900
ttaacttctc tgcctcaatg gatgctacta cttgtaataa agtgtgttag ggatgatggc      960
gcctcattcc tttccttatg aataaaacat gcatatgtat tttttggagg c             1011

<210> SEQ ID NO 6
<211> LENGTH: 588
```

<212> TYPE: DNA
<213> ORGANISM: Malus domestica

<400> SEQUENCE: 6

```
aacaaaggca gctaaccatg gccaggtttt cggtcatcgt ggcaatagtg ttcttatttg    60
tgatagctcc ttttgtcagt aatgccacca taacttgtgg tgaagtggta gcttggctca   120
ctccatgcat acccttttgga gtgtttggag gcacagtgcc tccagattgc tgtaaaggca   180
taaaagagct gaatgctgca caaaacacca cgatggaccg gagaattgct tgtagttgca   240
ttcaggaagg agctgcagca atccccggga ttaattatga ccggattaac actcttggtg   300
atgtctgtgg ctctccttgt ccttacaaag tttaccccctc tacaaattgc tctgcggtaa   360
gctgaatcca taggaggatt ggagaatgga gaataaagct tccgagaaga ctattcctcg   420
aagccatata gctagacaga cctcttagtt gtttaaatca caatgctttt gtggaactta   480
ataatttgga agggtcgaat cgttctgtat aaggattgta cgtaatccat taccatctat   540
taataattaa atgatcccct tttatacaaa aaaaaaaaaa aaaaatgc                588
```

<210> SEQ ID NO 7
<211> LENGTH: 717
<212> TYPE: DNA
<213> ORGANISM: Malus domestica

<400> SEQUENCE: 7

```
cgaattccgt tgctgtcgca cattaataca agttttgagg catcttaagt taagtttaaa    60
ccctaattag ccatgaaagg tgctcagttc ctcgtatgca ttgttgccat cttggcattc   120
gcaacctccc ttgtctctgc ctctgacccc agtcccctcc aggacttctg cgttgcactt   180
aatgacacca aattagggtt gtttgtgaac gggaattttt gcaaggaccc aaagcttgca   240
tcagcaaatg atttcttctt ttctgggctt caaattccaa gaagcacaca aaatccgttg   300
ggttcaacgg taacacctgc taatgtggat caaatagcag gactaaacac tctcggcata   360
tccctagctc gcatagactt tgcaccaaat ggcctaaacc ctccccacac tcaccctcgc   420
ggcacggaaa tcctttttct ccaggaaggt acactctacg ttgggttcgt aacgtccaac   480
ccagataatc gtctattcac caaggtgttg aacaaggag atgtgtttgt gttcccagtt   540
ggtcttattc acttccaact gaatgtggga cataccagtg ctgtcgccat tgctggtctt   600
agcagccaga acccaggagt catcaccata gcaaatgcag tgttcggcgc caaccctccc   660
atcaatcccg atgttctagc caaggccttc caagtcgatg acaaactggt ttcatat      717
```

<210> SEQ ID NO 8
<211> LENGTH: 301
<212> TYPE: DNA
<213> ORGANISM: Malus domestica

<400> SEQUENCE: 8

```
gaggcatttg gaggagaatt gaggaacacc gtaaagaaca cggtgagcca agtcgcaaag    60
aggactttaa caactggggt aaatggggag cttcaccccct caagattctg cgagaaggat   120
ctcctcaaag ttgtcgatag ggagtatgtt tttgcctata ttgatgagcc ctgcagcgcc   180
acttatccat tgatgcaaaa actgaggcaa gtgcttgttg agcatgcttt gacaaatggc   240
gagagtgaga agaatgcaag cacttcaatc ttccaaaaaa ttggagcttt cgaggaagag   300
c                                                                   301
```

<210> SEQ ID NO 9

```
<211> LENGTH: 442
<212> TYPE: DNA
<213> ORGANISM: Malus domestica

<400> SEQUENCE: 9
atcacggcgg tgaccttccg tgggcctagt gacacccacc ttgacagtct tgtgggtcaa      60
gccttgtttg gcgacggtgc agcggccgtc atcattggtg ccgacccagt gcccgaagtc     120
gagaagccct tgcttgaatt ggtctcggcg cacaaaacca ttctcgctga cagtgatggg     180
gctatcgacg gacatctccg tgaagtaggg cttacgtttc acctttgaa ggacgttccc     240
gggcttattt caaagaacat cgaaaagagc cttaacgagg ccttcaagcc ataggcatt     300
tcggactgga actcactctt ctggattgca cacccaggtg ccctgctat tctggaccaa     360
gtagaggcca agttggcgtt gaagccggag aaattagaag cgacaaggca agtgttgtca     420
gattacggca acatgtcaag tg                                              442

<210> SEQ ID NO 10
<211> LENGTH: 290
<212> TYPE: DNA
<213> ORGANISM: Malus domestica

<400> SEQUENCE: 10
accggttgga tgtacttcgt ctcctttact ctagctgttc aagctgcatg gaaatatgcc      60
aaagaaaaca acattgattt catcaccatt atcccaactc ttgtaattgg gccatttctc     120
atgccatcca tgccaccaag cctcatcact ggactttcgc cgatttaag aaatgaatca     180
cattatggca tcatcaagca gggccagtat gttcacttgg acgacctctg cctttctcac     240
attcatctgt acaagcatcc aaaagccgag ggccgttaca tttgctcctc                 290

<210> SEQ ID NO 11
<211> LENGTH: 1074
<212> TYPE: DNA
<213> ORGANISM: Malus domestica

<400> SEQUENCE: 11
atggtgagct ctgattcagt gaattcaagg gttgagacct tggccggcag tggaatctca      60
accatcccaa aagagtacat cagacctaaa gatgagcttg taaacattgg tgacatcttc     120
gaacaagaga gaacaacga agggcctcaa gttcccacca tcgatttgaa ggagatagag     180
tctgataacg aaaaagtgag agcaaaatgc agggaggagt tgaagaaggc agctgtggac     240
tggggtgtta tgcaccttgt gaaccatggc atctctgacg agctcatgga caaggtcagg     300
aaggccggta aggccttctt tgaccttccc attgagctga aggagaagta tgccaatgac     360
caggcctctg gtaagattca aggctatgga agcaagcttg caaacaatgc atctgggcag     420
cttgagtggg aggactactt cttccactgt gtatacccag aggacaagcg tgacttgtct     480
atttggcctc aaacacctgc tgattacatt gaggcaaccg ccgagtatgc taagcaactg     540
agggagctag caaccaaggt actgaaagtt ctgtcacttg gcttgggatt ggatgaaggg     600
aggctggaga agaagttgg tggacttgaa gagctcctct tgcaaatgaa aatcaactac     660
tacccaaaat gccctcagcc ggagcttgca cttggtgttg aagctcacac tgacgtgagt     720
gcactcacct tcatcctcca aacatggtt cctggcctgc agcttttcta tgaaggaaag     780
tgggtcactg ccagtgcgt tccaaattcc atcgtcatgc acattgggga cacacttgag     840
atttgagca atgggaagta caaaagtata ctccacaggg gcatggtgaa caaggaaaag     900
gtgaggattt catgggcagt tttctgtgag ccaccaaagg agaagatcat ccttaagcca     960
```

```
ctgccggaga ccgtgtccga ggaggagccg gcaatgttcc caccacgaac ttttgctgag   1020
cacattcaac acaagttgtt caggaagagt caaggggctt gctccccaa gtga           1074
```

<210> SEQ ID NO 12
<211> LENGTH: 1993
<212> TYPE: DNA
<213> ORGANISM: Malus domestica

<400> SEQUENCE: 12

```
aaaccagaga gctaagccat gacgtctctt tcacctccgg tagtcaccac ccccaccgtt     60
cccaaccccg ccacaaaacc tctctcccc ttctctcaaa acaactccca agtttcccta    120
ctcacaaagc ccaagcgttc ctttgcacgt aaggtctcat gcaaagccac aaacaatgac   180
caaaatgatc aagcacagtc caaactagac aggagaaatg tgcttcttgg tcttggaggt   240
ctatacggcg tggcgggtat gggcacagac ccgttcgctt ttgccaagcc tatagcccca   300
ccagacgtat ctaaatgtgg tcctgcagac ttgccacagg gtgcagtgcc caccaactgc   360
tgcccgccgc cttccacaaa atcattgac tttaagctgc ctgccccgc caaactccgc     420 atcaggccac cggctcacgc cgttgaccaa gcctacaggg acaaatacta caaagcgatg   480
gagctcatga aggccctacc cgacgacgac ccacgtagct tcaagcaaca ggcagccgtg   540
cattgcgctt attgcgacgg cgcctatgac caagtcgggt tcccagaact cgagctccaa   600
atccacaact catggctctt cttcccgttc caccgttact acttgtactt tttcgagaag   660
atcctaggca aactcattaa cgacccgaca ttcgcttgc cgttctggaa ctgggactcg    720
ccagccggca tgccactgcc cgcaatttac gctgatccaa gtcccctct ctacgacaag    780 ctccgatctg ccaatcatca gccccgact ctggtcgatc tcgattacaa cgggaccgag    840
gacaatgtgt caaggaaac cacaatcaac gccaatctca aaatcatgta caggcaaatg   900
gtgtccaatt ccaagaatgc taagttgttc tttgggaacc cgtacagggc aggggacgag   960
cctgaccctg gtgcggctc catcgagggg acaccacacg cgccggttca tttatggacc   1020
ggtgacaaca cccagcccaa cttttgaggac atgggggaatt tttactccgc tggtcgggac  1080
cccatatttt ttgcacacca ttcgaatgtc gatcgaatgt ggagtatttg gaaaactctt   1140
ggaggtaaga gaactgatct tactgactcg gactggttgg actccggatt cttgttttac   1200
aacgagaaca cagagttagt ccgagtcaag gtcagggact gcttggagac caaaaatctt   1260
gggtatgtat accaagatgt ggacattcct tggctcagct ccaagccaac accgcgaagg   1320
gcgaaagttg cattgagcaa agtagcgaag aagctggagg ttgcacacgc agctgttgcg   1380
tcgtccagca aggtggtggc aggcactgag ttcccgataa gtctggggtc gaagataagc   1440
acggtggtga agagaccgaa gcagaagaag aggagcaaga aggccaagga ggatgaggag   1500
gagatattgg tgattgaggg aatcgagttt gacagggacg tggctgtgaa gtttgatgtg   1560
tatgtgaatg acgtcgatga cttgccgagt gggcctgaca agacggagtt tgccggaagc   1620
tttgtaagtg tgccgcacag ccacaagcac aagaagaaga tgaacactat tttgaggtta   1680
gggttgacag atttgttgga ggaaattgag gcggaggacg atgacagcgt ggtggtgact   1740
ttggtgccca agtcggcgc tgtcaagatt ggtggtatca agattgaatt tgcttcttag   1800
ttagttatgt caacccaggc atcaagaatc gtatgatcat catcatgctt ggatcgatca   1860
tgtgttgtaa ttcttcaatt tggtggtttt gttccttttg aatagtcaat gttcgtgtac   1920
aaaataaaca tgatgatgat gtggtatttt catcaccatg aaatatgaat taggaaatca   1980
``` catttgttc gtt 1993

<210> SEQ ID NO 13
<211> LENGTH: 1827
<212> TYPE: DNA
<213> ORGANISM: Malus domestica

<400> SEQUENCE: 13

```
atggacgtcc gaaggcgatc gacgatggat acacctgcca ccaaggccag aagtgggccg      60
atgaaggtga agtggtgga ccacgagaac gacgttggtg tcgtcggggc caaggcctcc     120
gacgccctgc cgctgccgtt gtacctgact aacgccgtct gcttcactct cttcttctcc    180
gtcgtctact tcctccttac tcgttggcgc gagaagatca agacctcgac gccgctccac    240
gtcgtgaacc tctccgagat cgtcgcgata ctcgcgttcg tcgcctcctt catctacttg    300
ctcggattct tcgggatcga tttcgtgcag tcgctcattc tccgcccag caatgacgtc     360
tgggccgccg acgatgacga ggaggagcac gagcgcttga tattgaaaga cgacgcgcgg    420
aaagtgccgt gtgggccgg actcgactgc agcccaattc cccaaattgc ctctgttgct     480
gctgccgccc caaagctgt tgcacagaag gtgtttgata agaggtagt cctctccact      540
tcctgcgatt tcaccgccca gccgttgacg gaggaagatg aggaggtggt caagtccgtg    600
gtggcgggaa ccatccctc ctactctctg gagtcaaagc tcggagattg caggagggcg     660
gcggctatca ggcgcgaggc gcttcagagg atcacaggaa agtctctggg tggtctgcca    720
ttggaggggt tcgattacga gtcaattctg ggtcagtgct gcgagatgcc agttgggtat    780
gttcagattc cagttgggat tgctgggcct cttatgctcc atggcagaga gttttccgta    840
ccaatggcca ccaccgaagg ttgcttggtt gccagcacca accgtggctt caaagctatc    900
aacttgtccg gcgagccac cagtgtgttg ctgagagatg ggatgaccag agcaccttgt    960
gtgaggttca actctgctaa gagagctgcc gagttgaagt tctacttgga agaacccaac    1020
aattatgaca ccttgtccac ggttttcaac aggtcaagca gattcggtag gcttcagaca    1080
attaagtgtg ccattgctgg gaagaacttg tacatgagat tcacctgcag caccggtgat    1140
gctatgggga tgaacatggt ctccaaaggt gtgcaaaacg tcttggattt cctccagaac    1200
gacttccctg acatggatgt gattggaatt tccggcaact actgctctga caagaagccc    1260
gctgcggtga actggattga aggccgcgga aaatcggtgg tctgtgaggc tgtgatcaag    1320
ggtgatgtgg tgcagaaggt gttgaaaacc aatgtggcgt ccctgtgcga gcttaacatg    1380
cttaagaacc ttactgggtc tgcaatggct ggagccctcg gtggattcaa cgcacatgcc    1440
agcaacatcg tctccgccat ctacatcgct accggccaag acccagctca gaatgtggag    1500
agttctcact gcattaccat gatggaaccc atcaatgatg acaggacct tcacgtgtct    1560
gtcaccatgc cttcaattga ggttggtact gttggaggtg ggacccaact tgcatctcaa    1620
tcagcttgtc tgaaccttct tggagtgaag ggtgctaaca gggaggcacc aggatcaaat    1680
gcaagattgt tggccactgt tgtggctggt tctgttcttg ctggagagct ttctctcatg    1740
tctgctatct cagctggaca gcttatgaat agtcacatga atactacag atcaagcaaa    1800
gatgtctcag ctgttgcatc cgcttaa                                       1827
```

<210> SEQ ID NO 14
<211> LENGTH: 1401
<212> TYPE: DNA
<213> ORGANISM: Malus domestica

<400> SEQUENCE: 14

```
atttttttcc ctctgtacca ttaagtcgtg tcgtctatac aaagcacatc tctctccctc    60
tctgtgagtc tgtgagtatc tggggagggc tctgagatta ccagtgtctg tgtggtggcg   120
gattagattg gcaaaactga caatggcgga tctcaagtca agtttctga aggtgtactc    180 cgttctgaaa tcggagctgt tggaagaccc tgctttcgac ttcaccaatg actctcgcca   240
atgggttgag cggatgctgg actacaatgt gcctggaggg aagcttaatc ggggattgtc   300
tgttattgac agctatcagt tgttgcaaca aggaagggaa ttaactgaag atgaaatctt   360
cctggccagc gctctcggtt ggtgcatcga atggcttcaa gcatttttc tggttcttga    420 tgacatcatg gatggctctc acacacgtcg tggtcagcct tgctggttta gattgcccaa   480
ggttggtatg attgcagtaa atgatggtgt tgtgcttcga aaccatatcc caaggattct   540
cagaaagtac ttcagagaaa agccatatta cgtggatctt cttgatttgt caatgaggt    600 ggaatttcaa actgcctcag gtcagatgat agatttgatc actactatcg aaggagaaaa   660
agatctatcc aaatactcat tgtcaattca ccgccgtatt gttcagtaca agactgccta   720
ttactcattt tacctttccg ttgcatgtgc attgcttatg tcaggtgagg aactggaaaa   780
acatattgat gtaaaaaaca ttcttgttga gatgggatc tactttcaag tacaggatga    840
ttatttggat tgctttggtg atccggaaac gattggtaag ataggaacag atattgaaga   900
tttcaagtgc tcttggttgg tggtgaaagc tttggaactc tgcaatgagg aacaaaagaa   960
agtactacat gagaattatg ggaaaccaga cccagaaaat gtggcaacag taaaggccct  1020
ctacaaagaa ctcgatattg agggtgtatt tgcggattat gagagcaaaa gctacaagaa  1080
actgacgagt tggattgaag ggcacccaag caaagcggtg caatcagtgt tgaagtcctt  1140
cttgggcaag atttacaaga ggcagaaata gaaatctcgg atctggattc agttcagccc  1200
ctcctatttg tatttggtgc atttgtaata aaacatgcag ttgcatttgg tttgcgtcag  1260
tcagagtcag gtttgcttca cttagttata agttgagtca tcagtgttga atgcagacag  1320
acaataagca tccacgttaa ttaatacaaa gtttctcagt ttccagttga gaatattaaa  1380
aaaaaaaaaa aaaaaaaaaa a                                            1401
```

<210> SEQ ID NO 15
<211> LENGTH: 562
<212> TYPE: DNA
<213> ORGANISM: Malus domestica

<400> SEQUENCE: 15

```
cagcattgca gctatcgaaa gcgacaatct cggcacaaga gacgatctct atggtactgc    60
attacacttc aagatcctca ggcagcatgg ctataaagtt tcacaagata tatttggtag   120
attcatggat gaaaagggca cattagagaa ccaccatttc gcgcatttaa aaggaatgct   180
ggaacttttc gaggcctcaa actgggtttt cgaaggtgaa gatatttag atgaggcgaa    240 agcttccttg acgctagctc tcagagatag tggtcatatt tgttatccag acagtaacct   300
ttccagggac gtagttcatt ccctggagct tccatcacac cggagagtgc agtggtttga   360
tgtcaaatgg caaatcaacg cctatgaaaa agacatttgt cgcgtgaacg ccacgttact   420
cgaattagca aagcttaatt tgaacgtaag tgaggcccca ctgcaaaaaa acttaaggga   480
agcatgcagg tggtgggcaa atctgggctt gggagacaac ttgaaatttg caagagatag   540
actgggtgaa tgttgctgat gt                                            562
```

<210> SEQ ID NO 16

<211> LENGTH: 198
<212> TYPE: DNA
<213> ORGANISM: Malus domestica

<400> SEQUENCE: 16

```
ggatacgaca ctatgaagaa tcgctgggaa aaattgacca acaccctgtc tgtttccaat      60
cgcttttctc tacagaaaat tgaaccccaa tattgcactt actttcagaa aattagagaa     120
ccctcaccag cttatgcgtg ggtgaagtgc gagagggaag aagataaaga ttgctacaaa     180
atactggaag aagcaaaa                                                   198
```

<210> SEQ ID NO 17
<211> LENGTH: 625
<212> TYPE: DNA
<213> ORGANISM: Malus domestica

<400> SEQUENCE: 17

```
ggatgccccc gtgccaccac cagaggccgt cttcctgatg ctaccaaggg taatgaccat      60
ttgagggatg tcttttgcaa gaccatgggc ctcagcgaca aggatattgt tactctctcc     120
ggtggtcaca ccctgggaag gtgccacaag gagcgatctg gatttgaagg accttggact     180
cccaaccccc ttatctttga caactcctac ttcaaggtgc ttcttggtgg agaccaggaa     240
ggtcttctaa tgcttccaac tgacaaggct cttctggatg accctgtctt ccgccctctt     300
gtggaaaaat atgctgcgga tgaagatgct ttctttgctg actatgctga atctcacatg     360
aagctctccg agcttgggtt tgctgaggcc taagcagagc tggagaacta caagggatga     420
agccgatgcc tgtgcgcctt gcttttgtat ttttggatgc ctcttggttg tgaggttgta     480
ggcagttggt gcttttcttt tttatctatc agattttagg aaagtgggac ttctagttcg     540
atttgaagaa cgaatgtttt taaactggat ggaatgctgg ttatcatcct cgttgattaa     600
ataatactgt aattttcaaa aaaaa                                           625
```

<210> SEQ ID NO 18
<211> LENGTH: 650
<212> TYPE: DNA
<213> ORGANISM: Malus domestica

<400> SEQUENCE: 18

```
ggctgccatc aaggtccacg gaaacgttat ttcgaccgct gcaatgcgag tttttgctac      60
tctctacgag aaagacatcg aattcgagct tgttccaatc gacatgagag ctggtgaaca     120
caaaaaggag cccttcatat ccctcaatcc atttggtcaa gttccagcat tcgaagacgg     180
agatcttaag ctcttttgaat caagggcgat tacacaatac attgcccacg agtatgctga     240
caagggaacc cctctagtga tccgagactc aaagaagatg gcaattatat cattgtggtc     300
ggaggtggag gcccaaaagt tcgacccggc ggccacaaaa ctgacctatg agctagctat     360
aaagcctatg tttaaaatga ccacagacgc ggcagttgtg gaggaaaatg aagccaagtt     420
ggctgtggtt cttgatgtat atgagactcg tctggctcag tcgaaatact ggcaggtga     480
aagcttcact ttggctgatc ttcaccacct ccccaccata cattacttga tgggaacaca     540
atcgaagaag ctgttcgaat cccgcccccc atgttctcgc atgggtggcg gatatcacag     600
caaggccagc ttgaacaaa agtcgttgcc cagcaaaagt gaaaacaagt              650
```

<210> SEQ ID NO 19
<211> LENGTH: 503
<212> TYPE: DNA
<213> ORGANISM: Malus domestica

<400> SEQUENCE: 19

```
cttcttcttc tctctttgct tcttagttat attggttatc agaaaccttg ttagatatta      60
gtcatgggtt catatattac tggttcatgc actcccacaa acactaaaat ctcattgtca     120
ttattattcc ttcttgttgg agtagcttct gctcaattgt cctctacttt ctatggaaca     180
tcgtgtccta atgccctgtc caccataaaa tcggcagtgg actcagcggt gtcgaaggaa     240
gctcgcatgg agcttccttt gcttcgtctt catttccatg attgctttgt taatggatgt     300
gatgcttcgg ttctgctgga tgacacagcc aatttcacag gagagaaaac agcaggtgct     360
aatgctaatt ctttgagggg atttgatgta atcgatacaa ttaaatctca attggagagt     420
ctctgcccca aagtagtctc ttgtgctgac atcttaactg ttgctgctag ggactctatt     480
gttgcattgg gtggacttac cta                                             503
```

<210> SEQ ID NO 20
<211> LENGTH: 562
<212> TYPE: DNA
<213> ORGANISM: Malus domestica
<220> FEATURE:
<221> NAME/KEY: misc_feature
<222> LOCATION: (472)..(472)
<223> OTHER INFORMATION: n is a, c, g, or t

<400> SEQUENCE: 20

```
gatattatta gctttgcgct ttttcattta ccagtatggg ctagtctatc accttaacat      60
cacaaacaac aaaagtttcc tggtatatgg tgtttcgtgg ctcgtgatca ttctagtttt     120
gtgtctgatg aaggctgtgt ctgctggaag gcgacgatta agtgcagact atcagctttt     180
gtttcgactg gttaagggat ttatatttat tacatttttta gccatcttca ttaccttaat    240
agtggtccct catatgacac ttcgggatgt tgtagtgtgc attcttgcct tcatgccaac     300
gggatgggga ttgcttttga ttgcgcaagc ttgtaagcca ctaattaaac gagcagggtt     360
ttgggaatca gttcaaacac ttgctcgcgg ttatgaaata atcattggat gcttcttttt    420
taccccggtt gcattcttgg cttggttttcc gtttgtttcc gaattccaaa cncgaatgct     480
cttcaaccaa gcattcagca gaggtttaca gatctcacgt attcttggag acaaaagaa     540
gggctctcac tcctccaaca aa                                              562
```

<210> SEQ ID NO 21
<211> LENGTH: 580
<212> TYPE: DNA
<213> ORGANISM: Malus domestica

<400> SEQUENCE: 21

```
gcttactaat caacagacat gccaaaatgg tttcaaaaac ctcaacattc ctagttctca      60
tttgcaatct ttcccaaact acgtcacgct ctcaaccaac ttgtccaaga tgcttagcaa     120
ctcactatca atacacaagg tctcaacttc ttcatcagct ctacattttta gcaaacaagt    180
tcgtggaaga cgacggcgtt tgctttcgga tgatgggttc ccagaatggg tttcagccgc     240
tgatcgaaag ctgctacaat cgataggtag cggaccaaac gctgtatatgg tagtagcaca     300
agacgggtcc gggaattaca agtcaatttc tgaagctgtg gatgctgcgt acaagctaca     360
gggtggggcg actaaaaggt ttgtcataca cgtgaaggca ggagtttaca gagaaaatat     420
cgagattaag aggacaatga agaacatcat gttcattgga gatggtatcg atgcaacgat     480
tgtcacaggg aataaaaatg cccaagatgg ttcaactaca tatcgctctg ccacatttgg     540
```

```
ggctaccgga gatggcttta ttgctcaaaa cttgaaattc                           580
```

<210> SEQ ID NO 22
<211> LENGTH: 1262
<212> TYPE: DNA
<213> ORGANISM: Malus domestica

<400> SEQUENCE: 22

```
ggcacgagga gagagatgag cagcggagca gggaaggtcg tgtgcgtcac cggtgcgtct     60
ggatacattg cttcatggct cgttaagctt cttctccagc gcggctacac cgtcaaggcc    120
tctattcgcg acccaaatga tccaactaag acagagcacc tgcatgcgct tgatggagcc    180
caagacagac ttcaactttt caaagcaaat ctgttggaag aaggttcttt tgactctgct    240
gttgagggtt gtgaaggcgt attccatact gcatctccct tttatcatga tgtcacagac    300
ccaaaggcag aactacttga acctgcggta aggggaccc ttaatgttct taattcgtgt     360
gcgaaatcac catcaatcaa acgggtggtt ttgacatctt ctatagccgc tgtagcatat    420
aatggaaagc ctcgaactcc tgatgtagta gttgatgaga cttggtttac agatccagat    480
gtttgtaagg aatcaaagct ttggtacgtg cttttcaaaga cttggctga agatgctgcg    540
tggaaatttg taaggagaa gggtattgac ttggttacaa ttaaccccgc aatggtgata    600
ggtcctctgt tacagccaac tcttaataca agtgctgcag cagttttaaa tgttattaag    660
ggagctcgaa cttttccaaa tgcaagtttt ggatggatta cgttaaaga tgttgccaat    720
gcacatattc aagcatttga gaggcctacc gctagtggca gatattgttt ggttgagaga    780
gttgcccact tctcagaagt tgtgagaatt ttacgtgagc tgtaccctac tttgcaactt    840
ccagagaagt gtgcagacga caagcctttt gtgccaacat atcaggtgtc caaggagaag    900
gcgaagagct tgggtgtcga atttattcca ctagatgtta gcctcaagga aacagttgaa    960
agtctgaagg aaaagggttt tgtcaatttc tgagtcattt cagtacggtg aagatgtttg   1020
aagtaaattc agtcgcggta aaacatatta tctgcttcca gtttgtgttt ccggttggtg   1080
acttaaactc cggtttccct ttttcggttt aagcttgct gtccagcttg ttgattccta    1140
tagatcacca ttgtgtgtgc agaataaaga agaaatgaac ctttttgaata aaatcttgga   1200
atcgtctgag taaagtgcgc tcatgcaact ttatccccat tgataaaaaa aaaaaaaaaa   1260
aa                                                                  1262
```

<210> SEQ ID NO 23
<211> LENGTH: 637
<212> TYPE: DNA
<213> ORGANISM: Malus domestica
<220> FEATURE:
<221> NAME/KEY: misc_feature
<222> LOCATION: (585)..(585)
<223> OTHER INFORMATION: n is a, c, g, or t

<400> SEQUENCE: 23

```
aaaaagggaa tgaaagcttg gagagatgct ggatatagg gaggagacta tcaagaaaag      60
ctgctctctt gccttggagg cacacaaatt cccaggtgaa ccgtttcttg tggagaactc    120
tgctgcagga tcatcagatg ttgttatcag ctttcctgca ggaacttggt ctgtggagag    180
tttgttttct ggagaaagtg attttggaga agcaaaagtc gatctcgaac tctttccttc    240
cttgaaaagt gttgggaact atgatccagc aaagccagaa gagatagact ttgcaattgc    300
aactatcaac caagcattcg ttgacaaagt taaacaaata ttggacaatt cccagctgaa    360
aatcaaggtg caagaggcca tcactgcaaa gaagagaata atatttaccg gccactctac    420
```

```
cggcggtgca attgctgcgt tgtcacaat ctggttctta gaaaattgct cgaaagaaat      480
cagtggatct ttcttctgtg tgactttcgg atctccccctt attggtgacc acattatttc   540
tcatgctctt aggagagaaa attggtctga atacttcata cattntgtca tgagatatga    600
cattgtccct cggattttgc ttgctcctct gtcatcc                              637

<210> SEQ ID NO 24
<211> LENGTH: 342
<212> TYPE: DNA
<213> ORGANISM: Malus domestica

<400> SEQUENCE: 24
caggtaactt cgttcctata tctcatgtgc tgctactgac aaatggagaa ctgcaatata     60
cattgggagc aaaagagtct tgtaaatgag ctagcacaag ggagggatct ggctaggcag    120
ctacagatcc atctcaacgt tccatcttcc tcttatggaa cccgggaatt gctggttcaa    180
aagatcatac tttcgtacga aaagcgcctt ccatgctga actctagcag ctcagcctca     240
gaaggtgagc aacaacagcc cacaggtcat gttgcaattc gaatggttga gtctccgccg    300
cattcgctaa atgaaagtcc ccggagtgaa gactccgacc gc                       342

<210> SEQ ID NO 25
<211> LENGTH: 648
<212> TYPE: DNA
<213> ORGANISM: Malus domestica

<400> SEQUENCE: 25
ggaggcttgc taaagctcat gtccttgccc acgattctgg ttatcatcag cttgttagtc     60
actggctacg aacacattgt gccacagaac cctacataat cgccacaaat cggcaactga    120
gtgtcatgca cccaatctat agattgttac atccccattt cagatacacc atggagatta    180
attctcttgc tcgtgaatca cttatcaatg ccggtggtat catcgaaacc tcattttcgc    240
ccaaaaagta ctcccttgag ctctgctctg ttgcgtatgg aaggaatgg cggtttgacc     300 aagaggcact cccagctgac cttattagaa ggggcatggc tgttgaggac ccaactgctc    360
cacatgggct aaggctaaca attgaagatt accccttttgc caatgatgga ctcctcttat   420
gggatgctat taaacaatgg gtcactgact atgtaaacca ctactaccca gactccagca    480
ttgtccagac tgatcaagag ctccaagcat ggtggacaga aatcaaaaca gttggccatg    540
ctgacaaaaa agatgagcca tggtggccag aactcaacac tccggaagac taatgggca    600 tcatcacaac aatggtttgg gtagcatctg gtcatcatgc agctgtca                 648

<210> SEQ ID NO 26
<211> LENGTH: 630
<212> TYPE: DNA
<213> ORGANISM: Malus domestica

<400> SEQUENCE: 26 ttttttttt ttagataaag ttaaacttta tttctgatcc aaactcatga ttttgacatg      60
taacttatct gatccggaag aatttaaccc tccatatccg tttgccaaat acaataatgt    120
tgctaattag catatgcagt gctgtaaacc cttttagtgg tgcataaatt gagaatgctc    180
aagagcacct tgttgctagt gcacctaggg gtcttgaatt ggctcaatgc cgatccattt    240
cctatgaaat attccaaaat tttcttgaac gttcccttct ccacaatccg aagctctaga   300
ggtccgatcg aattacttcg cctcgagaca acgtaaccat gatccacgaa agatgcatcc   360
```

```
atttctctgc aacattcacc aagaaccctc tcttcaactt ctcctttgat ctcccagtat    420
attatgtagt ggcctggttg ggtcagcaca tcagcatggc ttgtgaagtc aatcagttct    480
gctttggact tgctcaatag ttgagaccct ctctccacca ccatttgaag gtccttttca    540
gtgttttcac acaactctct gcatttctgc tctgcccacc cactaaatca cttgacacac    600
ccacaccggc aatggacctc ctcctcctgg                                     630
```

<210> SEQ ID NO 27
<211> LENGTH: 1214
<212> TYPE: DNA
<213> ORGANISM: Malus domestica
<220> FEATURE:
<221> NAME/KEY: misc_feature
<222> LOCATION: (999)..(999)
<223> OTHER INFORMATION: n is a, c, g, or t

<400> SEQUENCE: 27

```
ccaaacactt gtagagcgag agagagagag agagagagag agagagagaa aatggagaac    60
ttcccagtta tcaacttgga gagcctcaat ggtgaggaa gaaaagctac aatggaaaag    120
atcaaagatg cctgtgagaa ctggggtttt tttgagctgg tgagtcatgg gattccaact    180
gagtttctgg acacagtgga gaggctgaca aaagagcact acaagcagtg tttggagcaa    240
aggttcaagg agctggtggc cagcaaaggc cttgagggtg ttcagacaga agtcaaagat    300
atggattggg aaagcacttt ccacttgcgc catcttcctc aatcgaacat ctctgaagta    360
ccagatctca aggatgagta caggaatgtg atgaaggagt ttgcattgaa attggaaaaa    420
ttagcagagc agctgctgga cttgttgtgt gagaatcttg gactggaaca agggtacctt    480
aagaaggcat tttatggaac aaagggacca acttttggca ccaaggtgag caactaccct    540
ccatgtccca acccagacct gatcaagggt ctccgggccc acaccgatgc cggcggcctc    600
atcttgctct tccaggatga caaggtcagt ggcctccagc tcctcaagga cggagagtgg    660
gttgatgtgc ctcccatgcg ccactccatt gttatcaatc ttggtgacca acttgaggtg    720
atcaccaacg gaaagtacaa gagtgtggaa cacagggtga ttgcccaaac agatggcacc    780
agaatgtcaa tagcttccatt ctacaaccca ggcagtgatg cggtgatcta cccagcacca    840
accctagtgg agaaagaagc agaggagaag aatcaagtgt acccgaaatc cgtgttcgaa    900
gactacatga agctctatgc tggggtcaag ttcgaggcca aggaaccaag atttgaagcc    960
atgaaagcag tggaaattaa ggccagtttt ggtttgggnc agttataag tactgcttga    1020 gagtgattaa atactttac tagaagctgt tggaaaaaag ggttgtttgc ttaaaagtaa    1080
ttatgggtgt gtgaacgaaa ttttccttg aactagattt caaggtttta tttactatta    1140
atgtggaaac cgttgtagaa agtaaccaat gtgatcacta ctttattata tataatatga    1200
cttcaagatt tgtt                                                      1214
```

<210> SEQ ID NO 28
<211> LENGTH: 616
<212> TYPE: DNA
<213> ORGANISM: Malus domestica

<400> SEQUENCE: 28

```
cacttcttga gagcttggag gaagggcttg tcaaagtgaa tcttaacgga tgcttgaatt    60
tgacagatga agtcgttatg gcgttggtta ggctacatgg ggaaacttta gaagtactga    120
atcttgatgt ttgcagaaag attactgatg caagcttggc gacaatcgca aacaactgct    180
tgtttcttcg tgagctagat gtgtcgaagt gtgcgattac agattctggc cttgctgccc    240
```

```
tttcttccgc agatcagatc aacttgcaag tcctctccat ttctggctgt tctgaaatct    300
cacacaaaag cctcccttcc ctgaaaaaat tgggccagac cctggtgggg ttgaatctcc    360
aacattgtac tgcactcagc tacagatcaa ttgagctact tgtggagagc ttgtggagat    420
gcgatatctt ggcctaataa ggaatagaac aatacgcgta tatagcgaag gagagaagca    480
gatatgaagt aggggtaaga tcaagaaatc aaaagaattc gggttagatt cgtcagttcg    540
tagatgttaa gcactcacac gggtatccac gttcagcata caacatttt ggcccgttgg    600 tagtggcctt gctggt                                                   616
```

<210> SEQ ID NO 29
<211> LENGTH: 596
<212> TYPE: DNA
<213> ORGANISM: Malus domestica

<400> SEQUENCE: 29

```
tgttcaatgc tgttggtggt ggtactggtt ctggtttggg gtccttgctc ttagaacgct     60
tgtcggtgga ttatggaaag aagtcaaagc ttgggttcac catctatcct tctccgcagg    120
tttcaacagc agttgttgag ccttataata gtgttctctc tactcatgcc ctccttgaac    180
acacagatgt atctgtgctc ttggacaatg aagctatcta tgatatttgc aggagatccc    240
tagacatcga gaccaaact tacaccaatt tgaatagact gatatcacaa gtcatatcct    300
ccttgacaac atcattgaga tttgatggag ccattaatgt tgatgtgaca gagttccaga    360
caaaccttgt tccatatccc cgcatccatt tcatgctttc ctcatatgcc cctgttatct    420
cagctgctaa ggcataccat gagcagatct caatccctga gatcacaaat gcagtttttg    480
aaccctcaag catgatggcc aagtgtgatc cccggcatgg aaaatacatg gcctgctgcc    540
taatgtacag gggtgatgta gttcccaaag atgtcaatgc tgctgttgca actatc        596
```

<210> SEQ ID NO 30
<211> LENGTH: 703
<212> TYPE: DNA
<213> ORGANISM: Malus domestica

<400> SEQUENCE: 30

```
accataacaa atggcagata cagaagacat tcaacctctc gtctgtgata atggcactgg     60
aatggttaag gctggatttg ctggagatga tgctccgagg gctgttttcc ccagtattgt    120
tggtcgtcct agacacacag gtgttatggt ggggatggga cagaaggatg cctatgttgg    180
ggatgaggcc cagtcgaaaa gggtattct cacattaaaa tacccccattg aacacgggat    240 tgttagcaat tgggatgaca tggaaagat ctggcatcat actttctaca atgagcttcg    300
tgtcgctcct gaagaacatc ctgtgcttct tactgaagca cctctgaatc ctaaggccaa    360
cagggaaaag atgactcaga tcatgtttga gaccttcaat gtccctgcta tgtatgttgc    420
cattcaagca gttctctccc tctatgctag tgggcgtact acaggtattg tgcttgactc    480
tggtgatgga gtcagtcaca ctgttcccat ctacgagggt tatgcacttc acatgccat     540 cctccggctt gaccttgctg gacgagactt aacagattcc ttaatgaaga tcctgactga    600
gagagggtat acttttacta ctactgctga acggggaatt gtgcgtgaca ttaaagagaa    660
gcttgcctat gtggcccttg cttatgaaag ggaatcggaa tcg                      703
```

<210> SEQ ID NO 31
<211> LENGTH: 545
<212> TYPE: DNA

<213> ORGANISM: Malus domestica

<400> SEQUENCE: 31

```
acaggttcgg aattgttgag ggtctcatga ccacggtgca ctccatcact gccacccaaa    60
agactgttga cggtccatca atgaaggact ggagaggtgg acgtgcagct tccttcaaca   120
tcattcctag tagcactgga gctgccaagg ctgttggaaa ggtgctccca tctcttaatg   180
gaaaattgac cggaatgtcc ttccgtgtgc ccactgttga tgtttccgtt gttgacctga   240
ctgtcaagct tgagaaggct gcaacctatg aacagatcaa ggccgctatc aaggaggagt   300
ctgaaggcaa gttgaagggt atcttgggtt acaccgaaga tgatgtcgtg tccaccgact   360
tcattggtga cagcaggtca agcatctttg atgccaaggc tggaattgca ttgaatgaca   420
actttgtcaa gcttgtctca tggtacgaca cgagtgggg ttacagttcc cgtgtggtag   480
acttgatcgt gcacgtagca tcgagtctct agggttttta ggttatggtt tgggagttca   540
caata                                                              545
```

<210> SEQ ID NO 32
<211> LENGTH: 22
<212> TYPE: DNA
<213> ORGANISM: artificial sequence
<220> FEATURE:
<223> OTHER INFORMATION: primer

<400> SEQUENCE: 32
agcacacgag ttcgactcat aa                                            22

<210> SEQ ID NO 33
<211> LENGTH: 20
<212> TYPE: DNA
<213> ORGANISM: artificial sequence
<220> FEATURE:
<223> OTHER INFORMATION: primer

<400> SEQUENCE: 33
cacaaaacta cgccaaccaa                                               20

<210> SEQ ID NO 34
<211> LENGTH: 20
<212> TYPE: DNA
<213> ORGANISM: artificial sequence
<220> FEATURE:
<223> OTHER INFORMATION: primer

<400> SEQUENCE: 34
aattgttata tcggagagtg                                               20

<210> SEQ ID NO 35
<211> LENGTH: 19
<212> TYPE: DNA
<213> ORGANISM: artificial sequence
<220> FEATURE:
<223> OTHER INFORMATION: primer

<400> SEQUENCE: 35
tggcaaagat gtaagtttc                                                19

<210> SEQ ID NO 36
<211> LENGTH: 17
<212> TYPE: DNA
<213> ORGANISM: artificial sequence
<220> FEATURE:
<223> OTHER INFORMATION: primer

```
<400> SEQUENCE: 36
gaaggtgcct cttggtg                                                      17

<210> SEQ ID NO 37
<211> LENGTH: 17
<212> TYPE: DNA
<213> ORGANISM: artificial sequence
<220> FEATURE:
<223> OTHER INFORMATION: primer

<400> SEQUENCE: 37
cgtcggtgtc aatttgg                                                      17

<210> SEQ ID NO 38
<211> LENGTH: 18
<212> TYPE: DNA
<213> ORGANISM: artificial sequence
<220> FEATURE:
<223> OTHER INFORMATION: primer

<400> SEQUENCE: 38 aaagggctc gcatttgg                                                      18

<210> SEQ ID NO 39
<211> LENGTH: 19
<212> TYPE: DNA
<213> ORGANISM: artificial sequence
<220> FEATURE:
<223> OTHER INFORMATION: primer

<400> SEQUENCE: 39
cttggcattg gaggacacc                                                    19

<210> SEQ ID NO 40
<211> LENGTH: 22
<212> TYPE: DNA
<213> ORGANISM: artificial sequence
<220> FEATURE:
<223> OTHER INFORMATION: primer

<400> SEQUENCE: 40
ccaagcccct gtcctaaacc tc                                                22

<210> SEQ ID NO 41
<211> LENGTH: 22
<212> TYPE: DNA
<213> ORGANISM: artificial sequence
<220> FEATURE:
<223> OTHER INFORMATION: primer

<400> SEQUENCE: 41
caacttgcct tgcctcatca gc                                                22

<210> SEQ ID NO 42
<211> LENGTH: 21
<212> TYPE: DNA
<213> ORGANISM: artificial sequence
<220> FEATURE:
<223> OTHER INFORMATION: primer

<400> SEQUENCE: 42
agtgttctta tttgtgatag c                                                 21

<210> SEQ ID NO 43
```

```
<211> LENGTH: 19
<212> TYPE: DNA
<213> ORGANISM: artificial sequence
<220> FEATURE:
<223> OTHER INFORMATION: primer

<400> SEQUENCE: 43
caactacaag caattctcc                                                    19

<210> SEQ ID NO 44
<211> LENGTH: 21
<212> TYPE: DNA
<213> ORGANISM: artificial sequence
<220> FEATURE:
<223> OTHER INFORMATION: primer

<400> SEQUENCE: 44
gcctaaaccc tccccacact c                                                 21

<210> SEQ ID NO 45
<211> LENGTH: 24
<212> TYPE: DNA
<213> ORGANISM: artificial sequence
<220> FEATURE:
<223> OTHER INFORMATION: primer

<400> SEQUENCE: 45
catctccctt gttcaacacc ttgg                                              24

<210> SEQ ID NO 46
<211> LENGTH: 20
<212> TYPE: DNA
<213> ORGANISM: artificial sequence
<220> FEATURE:
<223> OTHER INFORMATION: primer

<400> SEQUENCE: 46
ggatctcctc aaagttgtcg                                                   20

<210> SEQ ID NO 47
<211> LENGTH: 19
<212> TYPE: DNA
<213> ORGANISM: artificial sequence
<220> FEATURE:
<223> OTHER INFORMATION: primer

<400> SEQUENCE: 47
ctcactctcg ccatttgtc                                                    19

<210> SEQ ID NO 48
<211> LENGTH: 19
<212> TYPE: DNA
<213> ORGANISM: artificial sequence
<220> FEATURE:
<223> OTHER INFORMATION: primer

<400> SEQUENCE: 48
attggtgccg acccagtgc                                                    19

<210> SEQ ID NO 49
<211> LENGTH: 25
<212> TYPE: DNA
<213> ORGANISM: artificial sequence
<220> FEATURE:
<223> OTHER INFORMATION: primer

<400> SEQUENCE: 49
```
aatccagaag agtgagttcc agtcc                                        25

<210> SEQ ID NO 50
<211> LENGTH: 17
<212> TYPE: DNA
<213> ORGANISM: artificial sequence
<220> FEATURE:
<223> OTHER INFORMATION: primer

<400> SEQUENCE: 50
cggttggatg tacttcg                                                 17

<210> SEQ ID NO 51
<211> LENGTH: 17
<212> TYPE: DNA
<213> ORGANISM: artificial sequence
<220> FEATURE:
<223> OTHER INFORMATION: primer

<400> SEQUENCE: 51
tgtgagaaag gcagagg                                                 17

<210> SEQ ID NO 52
<211> LENGTH: 20
<212> TYPE: DNA
<213> ORGANISM: artificial sequence
<220> FEATURE:
<223> OTHER INFORMATION: primer

<400> SEQUENCE: 52
gcctcaagtt cccaccatcg                                              20

<210> SEQ ID NO 53
<211> LENGTH: 22
<212> TYPE: DNA
<213> ORGANISM: artificial sequence
<220> FEATURE:
<223> OTHER INFORMATION: primer

<400> SEQUENCE: 53
gaagtagtcc tcccactcaa gc                                           22

<210> SEQ ID NO 54
<211> LENGTH: 17
<212> TYPE: DNA
<213> ORGANISM: artificial sequence
<220> FEATURE:
<223> OTHER INFORMATION: primer

<400> SEQUENCE: 54
tgcccgccgc cttccac                                                 17

<210> SEQ ID NO 55
<211> LENGTH: 25
<212> TYPE: DNA
<213> ORGANISM: artificial sequence
<220> FEATURE:
<223> OTHER INFORMATION: primer

<400> SEQUENCE: 55
gctccatcgc tttgtagtat ttgtc                                        25

<210> SEQ ID NO 56
<211> LENGTH: 18
<212> TYPE: DNA

```
<213> ORGANISM: artificial sequence
<220> FEATURE:
<223> OTHER INFORMATION: primer

<400> SEQUENCE: 56
aacaggtcaa gcagattc                                                  18

<210> SEQ ID NO 57
<211> LENGTH: 18
<212> TYPE: DNA
<213> ORGANISM: artificial sequence
<220> FEATURE:
<223> OTHER INFORMATION: primer

<400> SEQUENCE: 57
ttgtcagagc agtagttg                                                  18

<210> SEQ ID NO 58
<211> LENGTH: 19
<212> TYPE: DNA
<213> ORGANISM: artificial sequence
<220> FEATURE:
<223> OTHER INFORMATION: primer

<400> SEQUENCE: 58
tcttggttgg tggtgaaag                                                 19

<210> SEQ ID NO 59
<211> LENGTH: 20
<212> TYPE: DNA
<213> ORGANISM: artificial sequence
<220> FEATURE:
<223> OTHER INFORMATION: primer

<400> SEQUENCE: 59
ctgcctcttg taaatcttgc                                                20

<210> SEQ ID NO 60
<211> LENGTH: 23
<212> TYPE: DNA
<213> ORGANISM: artificial sequence
<220> FEATURE:
<223> OTHER INFORMATION: primer

<400> SEQUENCE: 60
gatattttag atgaggcgaa agc                                            23

<210> SEQ ID NO 61
<211> LENGTH: 20
<212> TYPE: DNA
<213> ORGANISM: artificial sequence
<220> FEATURE:
<223> OTHER INFORMATION: primer

<400> SEQUENCE: 61
gcgttgattt gccatttgac                                                20

<210> SEQ ID NO 62
<211> LENGTH: 21
<212> TYPE: DNA
<213> ORGANISM: artificial sequence
<220> FEATURE:
<223> OTHER INFORMATION: primer

<400> SEQUENCE: 62
caccctgtct gtttccaatc g                                              21
```

<210> SEQ ID NO 63
<211> LENGTH: 25
<212> TYPE: DNA
<213> ORGANISM: artificial sequence
<220> FEATURE:
<223> OTHER INFORMATION: primer

<400> SEQUENCE: 63
agcaatcttt atcttcttcc ctctc                                    25

<210> SEQ ID NO 64
<211> LENGTH: 23
<212> TYPE: DNA
<213> ORGANISM: artificial sequence
<220> FEATURE:
<223> OTHER INFORMATION: primer

<400> SEQUENCE: 64
gcttccaact gacaaggctc ttc                                      23

<210> SEQ ID NO 65
<211> LENGTH: 18
<212> TYPE: DNA
<213> ORGANISM: artificial sequence
<220> FEATURE:
<223> OTHER INFORMATION: primer

<400> SEQUENCE: 65
cgcacaggca tcggcttc                                            18

<210> SEQ ID NO 66
<211> LENGTH: 23
<212> TYPE: DNA
<213> ORGANISM: artificial sequence
<220> FEATURE:
<223> OTHER INFORMATION: primer

<400> SEQUENCE: 66
gagcccttca tatccctcaa tcc                                      23

<210> SEQ ID NO 67
<211> LENGTH: 18
<212> TYPE: DNA
<213> ORGANISM: artificial sequence
<220> FEATURE:
<223> OTHER INFORMATION: primer

<400> SEQUENCE: 67
gcctccacct ccgaccac                                            18

<210> SEQ ID NO 68
<211> LENGTH: 24
<212> TYPE: DNA
<213> ORGANISM: artificial sequence
<220> FEATURE:
<223> OTHER INFORMATION: primer

<400> SEQUENCE: 68
tgtcattatt attccttctt gttg                                     24

<210> SEQ ID NO 69
<211> LENGTH: 18
<212> TYPE: DNA
<213> ORGANISM: artificial sequence
<220> FEATURE:

<223> OTHER INFORMATION: primer

<400> SEQUENCE: 69
aaccgaagca tcacatcc                                                 18

<210> SEQ ID NO 70
<211> LENGTH: 21
<212> TYPE: DNA
<213> ORGANISM: artificial sequence
<220> FEATURE:
<223> OTHER INFORMATION: primer

<400> SEQUENCE: 70
tgccttcatg ccaacgggat g                                             21

<210> SEQ ID NO 71
<211> LENGTH: 23
<212> TYPE: DNA
<213> ORGANISM: artificial sequence
<220> FEATURE:
<223> OTHER INFORMATION: primer

<400> SEQUENCE: 71
cggaaacaaa cggaaaccaa gcc                                           23

<210> SEQ ID NO 72
<211> LENGTH: 18
<212> TYPE: DNA
<213> ORGANISM: artificial sequence
<220> FEATURE:
<223> OTHER INFORMATION: primer

<400> SEQUENCE: 72
ggagggaggg tcaactgg                                                 18

<210> SEQ ID NO 73
<211> LENGTH: 22
<212> TYPE: DNA
<213> ORGANISM: artificial sequence
<220> FEATURE:
<223> OTHER INFORMATION: primer

<400> SEQUENCE: 73
caaacaactt ctctccacaa cc                                            22

<210> SEQ ID NO 74
<211> LENGTH: 22
<212> TYPE: DNA
<213> ORGANISM: artificial sequence
<220> FEATURE:
<223> OTHER INFORMATION: primer

<400> SEQUENCE: 74
ggagcccaag acagacttca ac                                            22

<210> SEQ ID NO 75
<211> LENGTH: 21
<212> TYPE: DNA
<213> ORGANISM: artificial sequence
<220> FEATURE:
<223> OTHER INFORMATION: primer

<400> SEQUENCE: 75
cgccttcaca accctcaaca g                                             21

<210> SEQ ID NO 76
<211> LENGTH: 24
<212> TYPE: DNA
<213> ORGANISM: artificial sequence
<220> FEATURE:
<223> OTHER INFORMATION: primer

<400> SEQUENCE: 76
tggagaaagt gattttggag aagc                                            24

<210> SEQ ID NO 77
<211> LENGTH: 22
<212> TYPE: DNA
<213> ORGANISM: artificial sequence
<220> FEATURE:
<223> OTHER INFORMATION: primer

<400> SEQUENCE: 77
agaaccagat tgtgacaaac gc                                              22

<210> SEQ ID NO 78
<211> LENGTH: 25
<212> TYPE: DNA
<213> ORGANISM: artificial sequence
<220> FEATURE:
<223> OTHER INFORMATION: primer

<400> SEQUENCE: 78
aatatacatt gggagcaaaa gagtc                                           25

<210> SEQ ID NO 79
<211> LENGTH: 20
<212> TYPE: DNA
<213> ORGANISM: artificial sequence
<220> FEATURE:
<223> OTHER INFORMATION: primer

<400> SEQUENCE: 79
agagttcagc atggaaagcg                                                 20

<210> SEQ ID NO 80
<211> LENGTH: 21
<212> TYPE: DNA
<213> ORGANISM: artificial sequence
<220> FEATURE:
<223> OTHER INFORMATION: primer

<400> SEQUENCE: 80
gttgcgtatg ggaaggaatg g                                               21

<210> SEQ ID NO 81
<211> LENGTH: 26
<212> TYPE: DNA
<213> ORGANISM: artificial sequence
<220> FEATURE:
<223> OTHER INFORMATION: primer

<400> SEQUENCE: 81
ggtagtagtg gtttacatag tcagtg                                          26

<210> SEQ ID NO 82
<211> LENGTH: 20
<212> TYPE: DNA
<213> ORGANISM: artificial sequence
<220> FEATURE:
<223> OTHER INFORMATION: primer

```
<400> SEQUENCE: 82
cgttcccttc tccacaatcc                                                   20

<210> SEQ ID NO 83
<211> LENGTH: 20
<212> TYPE: DNA
<213> ORGANISM: artificial sequence
<220> FEATURE:
<223> OTHER INFORMATION: primer

<400> SEQUENCE: 83
gggttcttgg tgaatgttgc                                                   20

<210> SEQ ID NO 84
<211> LENGTH: 20
<212> TYPE: DNA
<213> ORGANISM: artificial sequence
<220> FEATURE:
<223> OTHER INFORMATION: primer

<400> SEQUENCE: 84
gttggtgctg ggtagatcac                                                   20

<210> SEQ ID NO 85
<211> LENGTH: 20
<212> TYPE: DNA
<213> ORGANISM: artificial sequence
<220> FEATURE:
<223> OTHER INFORMATION: primer

<400> SEQUENCE: 85
acggagagtg ggttgatgtg                                                   20

<210> SEQ ID NO 86
<211> LENGTH: 19
<212> TYPE: DNA
<213> ORGANISM: artificial sequence
<220> FEATURE:
<223> OTHER INFORMATION: primer

<400> SEQUENCE: 86
cgttatggcg ttggttagg                                                    19

<210> SEQ ID NO 87
<211> LENGTH: 20
<212> TYPE: DNA
<213> ORGANISM: artificial sequence
<220> FEATURE:
<223> OTHER INFORMATION: primer

<400> SEQUENCE: 87
cagaaatgga gaggacttgc                                                   20

<210> SEQ ID NO 88
<211> LENGTH: 20
<212> TYPE: DNA
<213> ORGANISM: artificial sequence
<220> FEATURE:
<223> OTHER INFORMATION: primer

<400> SEQUENCE: 88
gttcaatgct gttggtggtg                                                   20

<210> SEQ ID NO 89
<211> LENGTH: 20
```

```
<212> TYPE: DNA
<213> ORGANISM: artificial sequence
<220> FEATURE:
<223> OTHER INFORMATION: primer

<400> SEQUENCE: 89
ctgcggagaa ggatagatgg                                          20

<210> SEQ ID NO 90
<211> LENGTH: 22
<212> TYPE: DNA
<213> ORGANISM: artificial sequence
<220> FEATURE:
<223> OTHER INFORMATION: primer

<400> SEQUENCE: 90
caacctctcg tctgtgataa tg                                       22

<210> SEQ ID NO 91
<211> LENGTH: 19
<212> TYPE: DNA
<213> ORGANISM: artificial sequence
<220> FEATURE:
<223> OTHER INFORMATION: primer

<400> SEQUENCE: 91
gcatccttct gtcccatcc                                           19

<210> SEQ ID NO 92
<211> LENGTH: 19
<212> TYPE: DNA
<213> ORGANISM: artificial sequence
<220> FEATURE:
<223> OTHER INFORMATION: primer

<400> SEQUENCE: 92
gctgccaagg ctgttggaa                                           19

<210> SEQ ID NO 93
<211> LENGTH: 22
<212> TYPE: DNA
<213> ORGANISM: artificial sequence
<220> FEATURE:
<223> OTHER INFORMATION: primer

<400> SEQUENCE: 93
cagtcaggtc aacaacggaa ac                                       22
```